US009040054B2

(12) United States Patent
Wallner et al.

(10) Patent No.: US 9,040,054 B2
(45) Date of Patent: May 26, 2015

(54) HYPOALLERGENIC MOLECULES

(75) Inventors: Michael Wallner, Salzburg (AT); Barbara Bohle, Vienna (AT); Martin Himly, Villach (AT); Nicole Wopfner, Salzburg (AT); Gabriele Gadermaier, Hallwang (AT); Matthias Egger, Salzburg (AT); Peter Lackner, Salzburg (AT); Fatima Ferreira, Salzburg (AT); Michael Hauser, Zams (AT)

(73) Assignee: BIOMAY AG, Vienna (AT)

( * ) Notice: Subject to any disclaimer, the term of this patent is extended or adjusted under 35 U.S.C. 154(b) by 792 days.

(21) Appl. No.: 12/674,195

(22) PCT Filed: Jun. 30, 2008

(86) PCT No.: PCT/EP2008/005324
§ 371 (c)(1),
(2), (4) Date: Jul. 8, 2010

(87) PCT Pub. No.: WO2009/024208
PCT Pub. Date: Feb. 26, 2009

(65) Prior Publication Data
US 2011/0217334 A1 Sep. 8, 2011

(30) Foreign Application Priority Data

Aug. 21, 2007 (EP) .................................... 07450145

(51) Int. Cl.
| | | |
|---|---|---|
| A61K 36/00 | (2006.01) |
| A61K 39/00 | (2006.01) |
| A61K 39/35 | (2006.01) |
| A61K 39/36 | (2006.01) |
| C07K 1/00 | (2006.01) |
| C07K 14/00 | (2006.01) |
| C07K 16/00 | (2006.01) |
| C07K 17/00 | (2006.01) |
| C07K 14/415 | (2006.01) |

(52) U.S. Cl.
CPC .................................... C07K 14/415 (2013.01)

(58) Field of Classification Search
None
See application file for complete search history.

(56) References Cited

FOREIGN PATENT DOCUMENTS

| JP | 2002-506648 A | 3/2002 | |
|---|---|---|---|
| JP | 2009-521910 A | 6/2009 | |
| WO | WO 2004/039834 A2 * | 5/2004 | ........... C07K 14/435 |

OTHER PUBLICATIONS

Ngo et, al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 1994.491-495.*
Lebecque et al. 'Immunologic characterization of monoclonal antibodies that modulate human IgE binding to the major birch pollen allergen Bet v 1.' J. Aller. Clin. Immunol. 99(3):374-384, 1997.*
Elsayed et al. 'Purification and N-Terminal Amino Acid Sequence of Two Birch Pollen Isoallergens (Bet v I and Bet v II).' Int. Arch. Allergy Appl. Immunol. 93:378-384, 1990.*
Blumenthal et al. 'Definition of an Allergen.' Allergens and Allergen Immunotherapy. Ed. R Lockey, S. Bukantz and J. Bousquet. New York: Marcel Decker, 2004. pp. 37-50.*
Skolnick et al. 'From genes to protein structure and function: novel applications of computational approaches in the genomic era.' Trends in Biotech. 18:34-39, 2000.*
Attwood et al. 'The Babel of Bioinformatics.' Science. 290(5491):471-473, 2000.*
Kuby et al. 'Immunology.' Fourth Edition, Chapter 18: 449-465, 2000.*
Pree et al. 'Analysis of epitope-specific immune responses induced by vaccination with structurally folded and unfolded recombinant Bet v 1 allergen derivatives in man.' J. Immunol. 179(8):5309-5316, 2007.*
Swoboda et al. 'Isoforms of Bet v 1, the major birch pollen allergen, analyzed by liquid chromatography, mass spectrometry, and cDNA cloning.' J. Biol. Chem. 270(6):2607-2613, 1995.*
Akdis, et al., "Differential regulation of human T cell cytokine patterns and IgE and IgG4 responses by conformational antigen variants," Eur. J. Immunol. (1998) 28:914-925.
Altschul, et al., "Basic Local Alignment Search Tool," J. Mol. Biol. (1990) 215:403-410.
Bolhaar, et al., "A mutant of the major apple allergen, Mal d 1, demonstrating hypo-allergenicity in the target organ by double-blind placebo-controlled food challenge," Clin Exp Allergy (2005) 35:1638-1644.
Devereux, et al., "A comprehensive set of sequence analysis programs for the VAX," Nucleic Acids Research (1984) 12(1):387-395.
Ferreira, et al., "Modulation of IgE reactivity of allergens by site-directed mutagenesis: potential use of hypoallergenic variants for immunotherapy," FASEB J. (1998) 12:231-242.
Gajhede, et al., "X-ray and NMR structure of Bet v 1, the origin of birch pollen allergy," Nature Structural Biology (1996) 2(12):1040-1045.
Gribskov, et al., "Sigma factors from E. coli, B. subtilis, phage SP01, and phage T4 are homologous proteins," Nucleic Acids Research (1986) 14(16):6745-6763.

(Continued)

Primary Examiner — Nora Rooney
(74) Attorney, Agent, or Firm — Oblon, McClelland, Maier & Neustadt, L.L.P.

(57) ABSTRACT

The present invention relates to a hypoallergenic molecule consisting of Bet v Ia or an allergen having at least 40% identity to Bet v Ia comprising mutations of at least four amino acid residues in the region of amino acids 100 to 125 of Bet v Ia or its corresponding region of the allergen having at least 40% identity to Bet v 1a.

2 Claims, 24 Drawing Sheets

(56) References Cited

OTHER PUBLICATIONS

Figure 1:
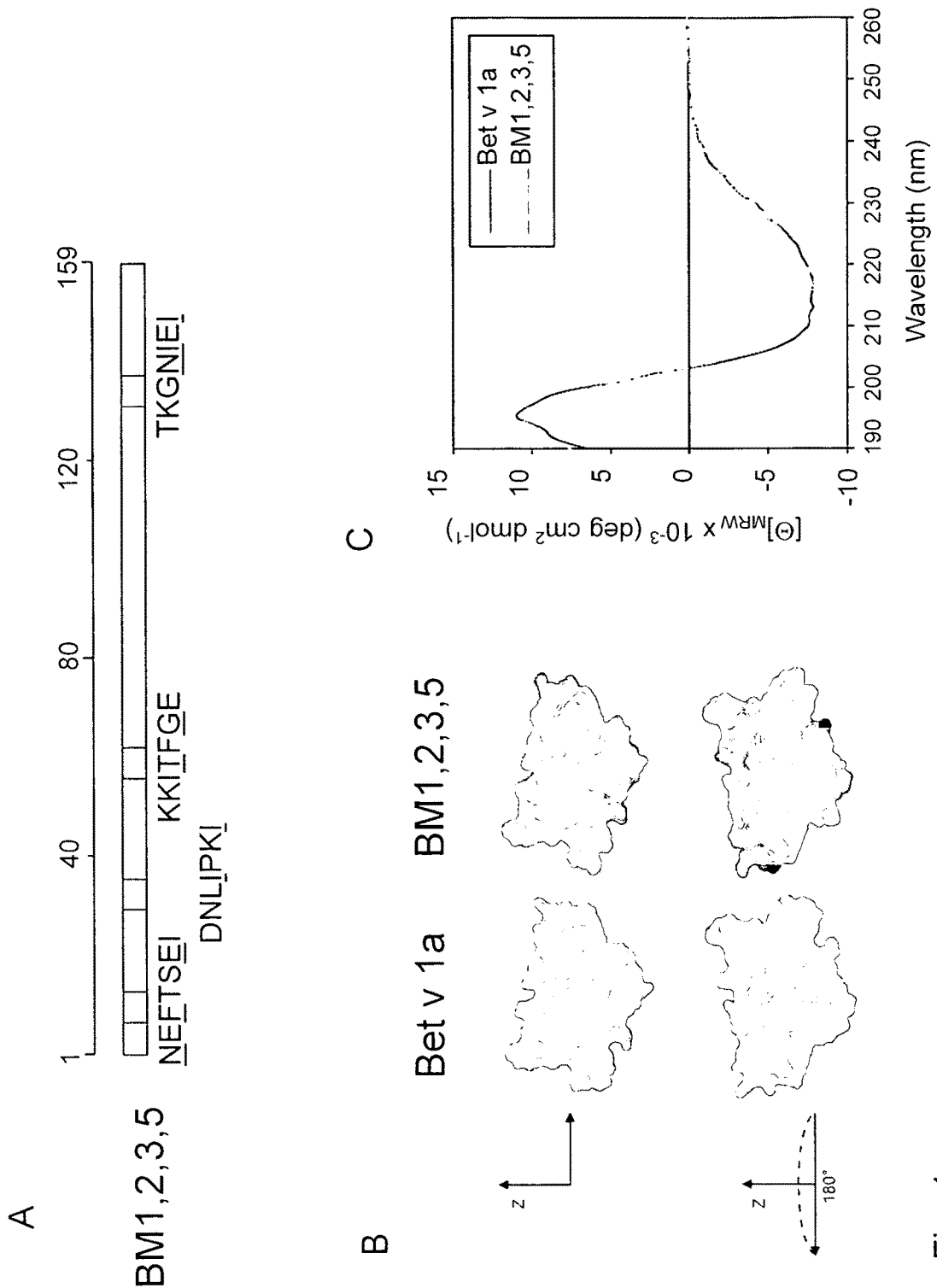

Larsen, et al., "Differences in Bet v 1 epitope specificies of individual patients IgE revealed by analysis of cross-reactivity between group 1 major allergens from birch and apple," J Allergy Clin Immunol (2002) pp. S164.

Needleman, et al., "A general method applicable to the search for similarities in the amino acid sequence of two proteins," J. Mol. Biol. (1970) 48:443-453.

Neudecker, et al., "Allergic cross-reactivity made visible," The Journal of Biological Chemistry (2001) 276 (26):22756-22763.

Pearson, et al., "Improved tools for biological sequence comparison," Proc. Natl. Acad. Sci. (1988) 85:2444-2448.

Schirmer, et al., "Crystal structure of the major celery allergen Api g 1: molecular analysis of cross-reactivity," J. Mol. Biol. (2005) 351:1101-1109.

Sippl, "Recognition of errors in three-dimensional structures of proteins," PROTEINS: Structure, Function, Genetics (1993) 17:355-362.

Sippl, et al., "Applications of knowledge based mean fields in the determination of protein structures," Statistical Mechanics, Protein Structure, and Protein Substrate Interactions (1994) pp. 297-315.

Son, et al., "Pollen-related food allergy: cloning and immunological analysis of isoforms and mutants of Mal d 1, the major apple allergen, and Bet v 1, the major birch pollen allergen," Eur J Nutr (1999) 38:201-215.

Wallner, et al., "Allergy multivaccines created by DNA shuffling of tree pollen allergens," J Allergy Clin Immunol (2007) 120:374-80.

Wallner, et al., "In vitro evolution of the Bet v 1 family by gene shuffling," J Allergy Clin Immunol (2002) pp. S164.

Wallner, Michael, et al., "Allergy multivaccines created by DNA shuffling of tree pollen allergens," J. Allergy Clin. Immunol., 2007, 120, p. 374-80.

Ferreira, Fatima, et al., "Modulation of IgE reactivity of allergens by site-directed mutagenesis: potential use of hypoallergenic variants for immunotherapy," FASEB J. 1998, 12, p. 231-42.

Scheurer, S., et al., "Cross-reactivity and epitope analysis of Pru a 1, the major cherry allergen," Mol. Immunol., 1999 Fe, 36(3), p. 155-67.

Office Action for JP 2010-51321 dated Apr. 2, 2013.

\* cited by examiner

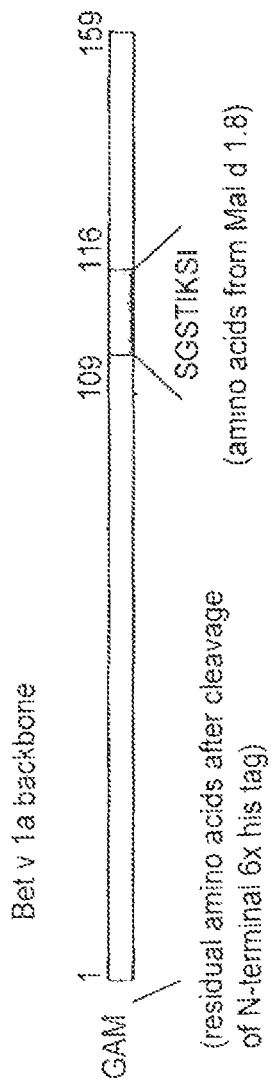

Fig. 3

| | | |
|---|---|---|
| SEQ ID NO: 3 BM4 | | GVFNYETETTSVIPAARLFKAFILDGDNLFPKVAPQAISSVENIEGNGGPGTIKKISFPE |
| SEQ ID NO: 1 Bet v 1a | | GVFNYETETTSVIPAARLFKAFILDGDNLFPKVAPQAISSVENIEGNGGPGTIKKISFPE |
| | | ************************************************************ |
| SEQ ID NO: 3 BM4 | | GFPFKYVKDRVDEVDHTNEKYNYSVIEGGPIGDTLEKISNEIKIVATPSGSTIKSISNKY |
| SEQ ID NO: 1 Bet v 1a | | GFPFKYVKDRVDEVDHTNFKYNYSVIEGGPIGDTLEKISNEIKIVATEDGGSILKISNKY |
| | | ***************************************** *********** *** |
| SEQ ID NO: 3 BM4 | | HTKGDHEVKAEQVKASKEMGETLLRAVESYLLAHSDAYN |
| SEQ ID NO: 1 Bet v 1a | | HTKGDHEVKAEQVKASKEMGETLLRAVESYLLAHSDAYN |
| | | ************************************** |

Fig. 4

| SEQ ID NO: 3 | BM4 | GVFNYETETTSVIPAARLEKAFILDGDNLFPKVARQAISSVENIEGNGGPGTIKKISFGE |
| SEQ ID NO: 2 | Mal d 1 | GVYTFENEFTSEIPPSRLFKAFVLDADNLFPKVAPQAIKQATKQAEILEGNGGPGTIKKITFGE |

| SEQ ID NO: 3 | BM4 | GFPFKYVKDRVDEVDKHTNFKYNISVIEGGPIGDTLEKISNEIKIVATPSGSTIKSISNKY |
| SEQ ID NO: 2 | Mal d 1 | GSQYGVVKHRIDSIDEASYSYSYTLIEGDALTDTIEKISYETKLVACGSGSTIKSISH-Y |
|              |         | *  *  *  *  * |

| SEQ ID NO: 3 | BM4 | HTKGDHEVKAEQVKASKEMGETLLRAVESYLLAHSDAYN |
| SEQ ID NO: 2 | Mal d 1 | HTKGNIEIKEEHVKAGKEKAHGLFKLIESYLKDHPDAYN |

Fig. 5

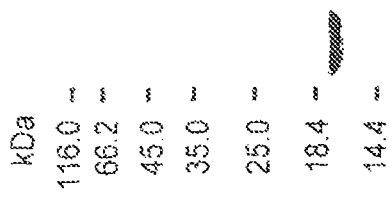

Fig. 6

```
BM4        GVFNYETETTSVIPAARLFKAFILDGDNLFPKVAPQAISSVENIEGNGGPGTIKKISFPE
Bet v 1a   GVFNYETETTSVIPAARLFKAFILDGDNLFPKVAPQAISSVENIEGNGGPGTIKKISFPE
           ************************************************************

BM4        GFPFKYVKDRVDEVDHTNFKYNYSVIEGGPIGDTLEKISNEIKIVATPSGSTIKSISNKY
Bet v 1a   GFPFKYVKDRVDEVDHTNFKYNYSVIEGGPIGDTLEKISNEIKIVATPDGG*SILKISNKY*
           ************************************************ **  *:*****

BM4        HTKGDHEVKAEQVKASKEMGETLLRAVESYLLAHSDAYN
Bet v 1a   *HTK*GDHEVKAEQVKASKEMGETLLRAVESYLLAHSDAYN
           ***************************************
```

Fig. 12

```
SEQ ID NO: 26  Dauc1.0101   E-GSPITSMTVRTDAVNKEALTYDSTVIDGDILLGFIESIETHLVVPTADGG-SITKTT  116
SEQ ID NO: 27  Dauc1.0102   E-GSPITSMTVRTDAVNKEALTYDSTVIDGDILLGFIESIETHLVVPTADGG-SITKTT  116
SEQ ID NO: 28  Dauc1.0104   E-GSPITSMTVRTDAVNKEALTYDSTVIDGDILLGFIESIETHLVVPTADGG-SITKTF  116
SEQ ID NO: 29  Dauc1.0105   E-GSPITSMTVRTDAVNKEALTYDSTVIDGDILLGFIESIETHLVVVPTADGG-SITKTF  116
SEQ ID NO: 30  Dauc1.0103   E-GSPITSMTVRTDAVNKEALTYDSTVIDGDILLEFIESIETHMVVVPTADGG-SITKTT  116
SEQ ID NO: 31  Apig1.0101   D-GGPITTMTLRIDGVNKEALTFDYSVIDGDILLGFIESIEMHVVLVPTADGG-SICKTT  116
SEQ ID NO: 32  Apig1.0201   E-ATEYTTMKQKVDVIDKAGLAYTYTTIGGDILVDVLESVVNEFVVVP-TDGG-CIVKNT  116
SEQ ID NO: 33  Dauc1.0201   E-ATEYTTMKQRVDVIDKAGLGYTYTTIGGDILVEGLESVVNQFVVVP-TDGG-CIVKNT  116
SEQ ID NO: 34  Petc1        D-ASFEKTMKQKVDAIDKATFTYSYSIIDGDILLGFIESINNHFTAVPNADGG-CTVKST  117
SEQ ID NO: 35  Cass1/1      E-ASKYKYSKHRIDALDPENCTYSFSVIEGDVLTD-IENVSTETKFVASPDGG-TIMKST  116
SEQ ID NO: 36  Cass1/3      E-ASKYKYSRHRIDALDPENCTYSFSVIEGDVLTD-IENVSTETKFVASPDGG-TIMKST  116
SEQ ID NO: 37  Cass1/2      E-ASKYKYSKHRIDALDPENCTYSFSVIEGDVLTD-IENVSTETKFVASPDGG-TIMKST  116
SEQ ID NO: 38  Quea1/7      E-ASKFKYAKHRIDALDPENCTYSFSVIEGDALTVXMESVSTEIKCVASPDGG-SIMKST  117
SEQ ID NO: 39  Quea1/8      E-GSHLKHAKHRIDVIDPSNFTYSFSVIEGDALFDKLENVSTETKIVASPDGG-SIVKST  117
SEQ ID NO: 40  Quea1/9      E-GSHLKHAKHRIDVIDPENFTYSFSVIEGDALFDKLENVSTETKIVASPDGG-SIAKST  117
SEQ ID NO: 41  Mald1.0101   E-GSQYGYVKHRIDSIDEASYSYSYTLIEGDALTDTIEKISYETKLVACGSG--STIKSI  116
SEQ ID NO: 42  Mald1.0102   E-GSQYGYVKHRIDSIDEASYSYSYTLIEGDALTDTIEKISYETKLVACGSG--STIKSI  116
SEQ ID NO: 43  Mald1.0109   E-GSQYGYVKHRIDSIDEASYSYSYTLIEGDALTDTIEKISYETKLVACGSG--STIKSI  116
SEQ ID NO: 44  Mald1.0105   E-GSQYGYVKHRIDSIDEASYSYSYTLIEGDALTDTIEKISYETKLVACGSG--STIKSI  116
SEQ ID NO: 45  Mald1.0106   E-GSQYGYVKHRIDSIDEASYSYSYTLIEGDALTDTIENISYETKLVACGSG--STIKSI  116
SEQ ID NO: 46  Mald1.0108   E-GSQYGYVKHRIDSIDEASYSYSYTLIEGDALTDTIEKISYETKLVACGSG--STIKSI  116
SEQ ID NO: 47  Mald1.0103   E-GSQYGYVKHRIDSIDEASYSYSYTLIEGDALTDTIEKISYETKLVACGSG--STIKSI  116
SEQ ID NO: 48  Mald1.0107   E-GSQYGYVKHRIDSIDEASYSYSYTLIEGDALTDTIEKISYETKLVACGSG--STIKSI  116
SEQ ID NO: 49  Mald1.0104   E-GSQYGYVKHRVDSIDEASYSYAYTLIEGDAFTDTIEKISYAAKLVASGSG--STIKSI  116
SEQ ID NO: 50  Pyrc1.0101   E-GSQYGYVKHKIDSVDEANYSYAYTLIEGDALTDTIEKVSYETKLVASGSG--SIIKSI  116
SEQ ID NO: 51  Mald1.0201   E-GSQYGYVKHKIDSVDEANYSYAYTLIEGDALTDTIEKVSYETKLVASGSG--SIIKSI  116
SEQ ID NO: 52  Mald1.0202   E-GSQYGYVKHKIDSVDEANYSYAYTLIEGDALTDTIEKVSYRTKLVASGSG--SIIKSI  116
SEQ ID NO: 53  Mald1.0203   E-GSQYGYVKHKIDSVDEANYSYAYTLIEGDALTDTIEKVSYETKLVASGSG--SIIKSI  116
SEQ ID NO: 54  Mald1.0207   E-GSQYGYVKHKIDSVDEANYSYAYTLIEGDALTDTIEKVSYETKLVASGSG--SIIKSI  116
SEQ ID NO: 55  Mald1.0205   E-GSQYGYVKHKIDSVDEANYSYAYTLIEGDALTDTIEKVSYETKLMASGSG--SIIKSI  116
SEQ ID NO: 56  Mald1.0204   E-GSQYGYVKHKIDSVDEANYSYAYTLIEGDALTDTIEKVSYETKLVASGSG--SIIKSI  116
SEQ ID NO: 57  Mald1.0206   E-GSQYGYVKHKIDSVDEANYSYAYTLIEGDALTDTIEKVSYETKLVASGSG--SIIKSI  116
SEQ ID NO: 58  Mald1.0208   E-GSQYGYVKHKIDSIDKENYSYSYTLIEGDALGDTLEKISYETKLVASPSGG-SIIKST  118
SEQ ID NO: 59  Pruav1.0101  E-GSQYGYVKHKIDSIDKENHSYSYTLIEGDALGDNLEKISYETKLVASPSGG-SIIKSF  117
SEQ ID NO: 60  Prup1        E-GSTYSVVKHRIDGVDKDNFVYKYSVIEGDAISETIEKISYETKLVAAG-SG-SVIKST  116
SEQ ID NO: 61  Mald1.0302   E-GSTYSVVKHRIDGVDKENFVYKYSVIEGDAISHTIEKISYETKLVASG-SG-SVIRST  116
SEQ ID NO: 62  Mald1.0304   E-GSTYSVVKHRIDGVDKDNFVYQYSVIEGDAISETIEKISYETKLVASG-SG-SVIKSI  116
SEQ ID NO: 63  Mald1.0303   E-GSTYSVVKHRIDGVDKENFVYKYSVIEGDAISETIEKISYETKLVASG-SG-SVIKST  116
SEQ ID NO: 64  Mald1.0301   E-GSHYSVVKHRIDGLDKDNFVYSYSLVEGDALSDKVEKISYEIKLVASADGG-SIIKST  118
SEQ ID NO: 65  Pruav1.0202  E-GSHYSVVKHRIDGLDKDNFVYSYSLVEGDALSDKVEKISYEIKLVASADGG-SIIKST  118
SEQ ID NO: 66  Pruav1.0203  E-GSHYSVVKHRIDGLDKDNFVYNYTLVEGDALSDKIEKITYEIKLVASADGG-SIIKST  118
SEQ ID NO: 67  Pruav1.0201  E-GTEHSVVKHKIDGLDKVNFVYSYSITEGDALGDKIEKISYEIKLVASG-RG-SIIKTT  108
SEQ ID NO: 68  Rubi1.0101   E-GSQYGVVKQRVNGIDKDNFTYSYSMIEGDTLSDRLEKITYETKLIASPDGG-SIIKTN  117
SEQ ID NO: 69  Mald1.0402   E-GSQYGVVKQRVNGIDKDNFTYSYSMIEGDTLSDRLEKITYETKLIASPDGG-SIIKTT  117
SEQ ID NO: 70  Mald1.0403   E-GSQYGVVKQRVNGIDKDNFTYSYSMIEGDTLSDRLEKITYETKLIASPDGG-SIIKTT  117
SEQ ID NO: 71  Mald1.0401   E-GSQYAYVKHRVDGIDKDNLSYSYTLIEGDALSDVIENIAYDIKLVASPDGG-SIVKTT  117
SEQ ID NO: 72  Pruar1.0101  E-GNEFKYMKHKVEEIDHANFKYCYSIIEGGPLGHTLEKISYEIKMAAAFHGGGSILKIT  118
SEQ ID NO: 73  Cora1.0401   E-GNEFKYMKHKVEEIDHANFKYCYSIIEGGPLGHTLEKIPYEIKMAAAFHGGGSILKIT  118
SEQ ID NO: 74  Cora1.0404   E-GSEFKYMKHKVEEIDHANFKYCYSIIEGGPLGHTLEKISYEIKMAAAFHGGGSILKIT  118
SEQ ID NO: 75  Cora1.0402
```

Fig. 13

```
SEQ ID NO 76   Coral.0403    E-GSEFKYMKHKVEEIDHANFKYCYSIIEGGPLGHTLEKISYEIKMAAAPHGGGSILKIT 118
SEQ ID NO 77   Coral.0301    E-GSPFNYIKQKVEEIDQANFSYRYSVIEGDALSDKLEKINYEIKIVASPHGG-SILKSI 117
SEQ ID NO 78   Betv1d        E-GFPFKYVKDRVDEVDHTNFKYNYSVIEGGPVGDTLEKISNEIKIVATPDGG-CVLKIS 117
SEQ ID NO 79   Betv1l        E-GFPFKYVKDRVDEVDHTNFKYNYSVIEGGPVGDTLEKISNEIKIVATPDGG-CVLKIS 117
SEQ ID NO 80   Betv1a1-6     E-GFPFKYVKDRVDEVDHTNFKYNYSVIEGGPIGDTLEKISNEIKIVATPDGG-CVLKIS 117
SEQ ID NO 81   Betv1g        E-GFPFKYVKDRVDEVDHTNFKYNYSVIEGGPVGDTLEKISNEIKIVATPDGG-CVLKIS 117
SEQ ID NO 82   Betv1a        E-GFPFKYVKDRVDEVDHTNFKYNYSVIEGGPIGDTLEKISNEIKIVATPDGG-SILKIS 117
SEQ ID NO 83   Betv1f        E-GFPFKYVKDRVDEVDHINFKYSYSVIEGGPVGDTLEKISNEIKIVATPNGG-SILKIN 117
SEQ ID NO 84   Betv1j        E-GFPFKYVKDRVDEVDHTNFKYSYSVIEGGPVGDTLEKISNEIKIVATPNGG-SILKIN 117
SEQ ID NO 85   Betv1e        E-GIPFKYVKGRVDEVDHTNFKYSYSVIEGGPVGDTLEKISNEIKIVATPNGG-SILKIN 117
SEQ ID NO 86   Betv1b        E-GSPFKYVKERVDEVDHANFKYSYSMIEGGALGDTLEKICNEIKIVATPDGG-SILKIS 117
SEQ ID NO 87   Betv1c        E-GSPFKYVKERVDEVDHANFKYSYSMIEGGALGDTLEKICNEIKIVATPDGG-SILKIS 117
SEQ ID NO 88   Alng1         E-GSPFKYVKERVDEVDRNFKYSFSVIEGGAVGDALEKVCNEIKIVAAPDGG-SILKIS 117
SEQ ID NO 89   Carb1.0301    E-GSPFKYVKERVEEVDHTNFKYSYTVIEGGPVGDKVEKICNEIKIVAAPDGG-SILKIT 117
SEQ ID NO 90   Carb1.0302    E-GSPVKYVKERVEEVDHTNFKYSYTVIEGGPVGDKVEKICNEIKIVAAPDGG-SILKIT 117
SEQ ID NO 91   Coral.0201    E-GSPFKYVKERVEEVDHTNFKYSYTVIEGGPVGDKVEKICNEIKIVAAPDGG-SILKIS 117
SEQ ID NO 92   Carb1.0103    E-GSPFKFVKERVDEVDNANFKYNYTVIEGDVLGDKLEKVSHELKIVAAPGGG-SIVKIS 117
SEQ ID NO 93   Carb1.0105    E-GSPFKFVKERVDEVDNANFKYNYTVIEGDVLGDKLEKVSHELKIVAAPGGG-SIVKIS 117
SEQ ID NO 94   Carb1.0104    E-GSPFKFVKERVDEVDNANFKYNYTVIEGDVLGDNLEKVSHELKIVAAPGGG-SIVKIS 117
SEQ ID NO 95   Carb1/3       E-GSPFKFVKERVDEVDNANFKYNYTVIEGDVLGDKLEKVSHELKIVAAPGGG-SIVKIS 117
SEQ ID NO 96   Carb1/1a      E-GIPFKFVKERVDEVDNANFKYNYTVIEGDVLGDKLEKVSHELKIVAAPGGG-SIVKIS 117
SEQ ID NO 97   Carb1.0101    E-GSPFKFVKERVDEVDNANFKYNYTVIEGDVLGDKLEKVSHELKIVAAPGGG-SIVKIS 117
SEQ ID NO 98   Carb1.0102    E-GIPFKFVKERVDEVDNANFKYNYTVIEGDVLGDKLEKVSHELKIVAAPGGG-SIVKIS 117
SEQ ID NO 99   Carb1/1b      E-GSPFKFVKERVDEVDNANFKYNYTVIEGDVLGDKLEKVSHELKIVAAPGGG-SIVKIS 117
SEQ ID NO 100  Carb1/5       E-GIPFKFVKERVDEVDNANFKYSYTVIEGDVLGDKLEKVSHELKIVAAPGGG-SIVKIS 117
SEQ ID NO 101  Carb1/2       E-GSPFKFVKERVDEVDNANFKYNYTVIEGDVLGDKLEKVSHELKIVAAPGGG-SVVKIS 117
SEQ ID NO 102  Carb1/4       E-GSPFKFVKERVDEVDNANFKYNYTVIEGDVLGDKLEKVSHELKIVAAPGGG-SIVKIS 117
SEQ ID NO 103  Carb1.0106a   E-GSPFKFVKERVDEVDNANFKYNYTVIEGDVLGDKLEKVSHELKIVAAPGGG-SIVKIS 117

SEQ ID NO 104  Carb1.0106b   E-GSPFKFVKERVDEVDNANFKYNYTVIEGDVLGDKLEKVSHELKIVAAPGGG-SIVKIS 117
SEQ ID NO 105  Carb1.0106c   E-GSPFKFVKERVDEVDNANFKYNYTVIEGDVLGDKLEKVSHELKIVAAPGGG-SIVKIS 117
SEQ ID NO 106  Carb1.0106d   E-GSPFKFVKERVDEVDNANFKYNYTVIEGDVLGDKLEKVSHELKIVAAPGGG-SIVKIS 117
SEQ ID NO 107  Carb1/1       E-GSPFKFVKERVDEVDNANFKYNYIVIEGDVLGDKLEKVSHELKIVAAPGGG-SILKIS 117
SEQ ID NO 108  Carb1.0107    E-GSPFKFVKERVDEVDNANFKFSYTVIEGDVLGDKLEKVSLELKIVAAPGGG-SILKIS 117
SEQ ID NO 109  Carb1.0108    E-GSPFKFVKERVDEVDNANFKFSYTVIEGDVLGDKLEKVSLELKIVAAPGGG-SILKIS 117
SEQ ID NO 110  Coral/5       E-GSRYKYVKERVDEVDNTNFTYSYTVIEGDVLGDKLEKVCHELKIVAAPGGG-SILKIS 117
SEQ ID NO 111  Coral/11      E-GSRYKYVKERVDEVDNTNFTYSYTVIEGDVLGDKLEKVCHELKIVAAPGGG-SILKIS 117
SEQ ID NO 112  Coral/6       E-GSRYKYVKERVDEVDNTNFKYSYTVIEGDVLGDKLEKVCSELKIVAAPGGG-SILKIS 117
SEQ ID NO 113  Coral/16      E-GSRYKYVKERVDEVDNTNFKYSYTVIEGDVLGDKLEKVCSELKIVAAPGGG-STLKIS 117
SEQ ID NO 114  Carb1/2or     E-GSPVKYVKERVEEIDHTNFKYNYTVIEGDVLGDKLEKVSHELKIVAAPGGG-SIVKIS 117
SEQ ID NO 115  Carb1.0201    G-GSPVKYVKERVEEIDHTNFKYNYTVIEGDVLGDKLEKVSHELKIVAAPGGG-SIVKIS 117
SEQ ID NO 116  Glym4.0101    E-DGETKFVLHKIESIDEANLGYSYSVVGGAALPDTAEKITFDSKLVAGPNGG-SAGKLT 116
SEQ ID NO 117  Vigr1.0101    E-DGETKFVLHKIESVDEANLGYSYSIVGGVALPDTAEKITIQTKISDGADGG-SLIKLT 116
SEQ ID NO 118  Arah8.0101    E-DGETKFILHKVESIDEANYAYNYSVVGGVALPETAEKITFETKLVEGPNGG-SIGKLT 115
SEQ ID NO 119  AspaoPR10     NPALPFSYVKERLGFVDHDKFEVKQTLVEGGGLGKMFECATTHFKFEPSSNGG-CLVKVT 118
```

Fig. 13 continuation

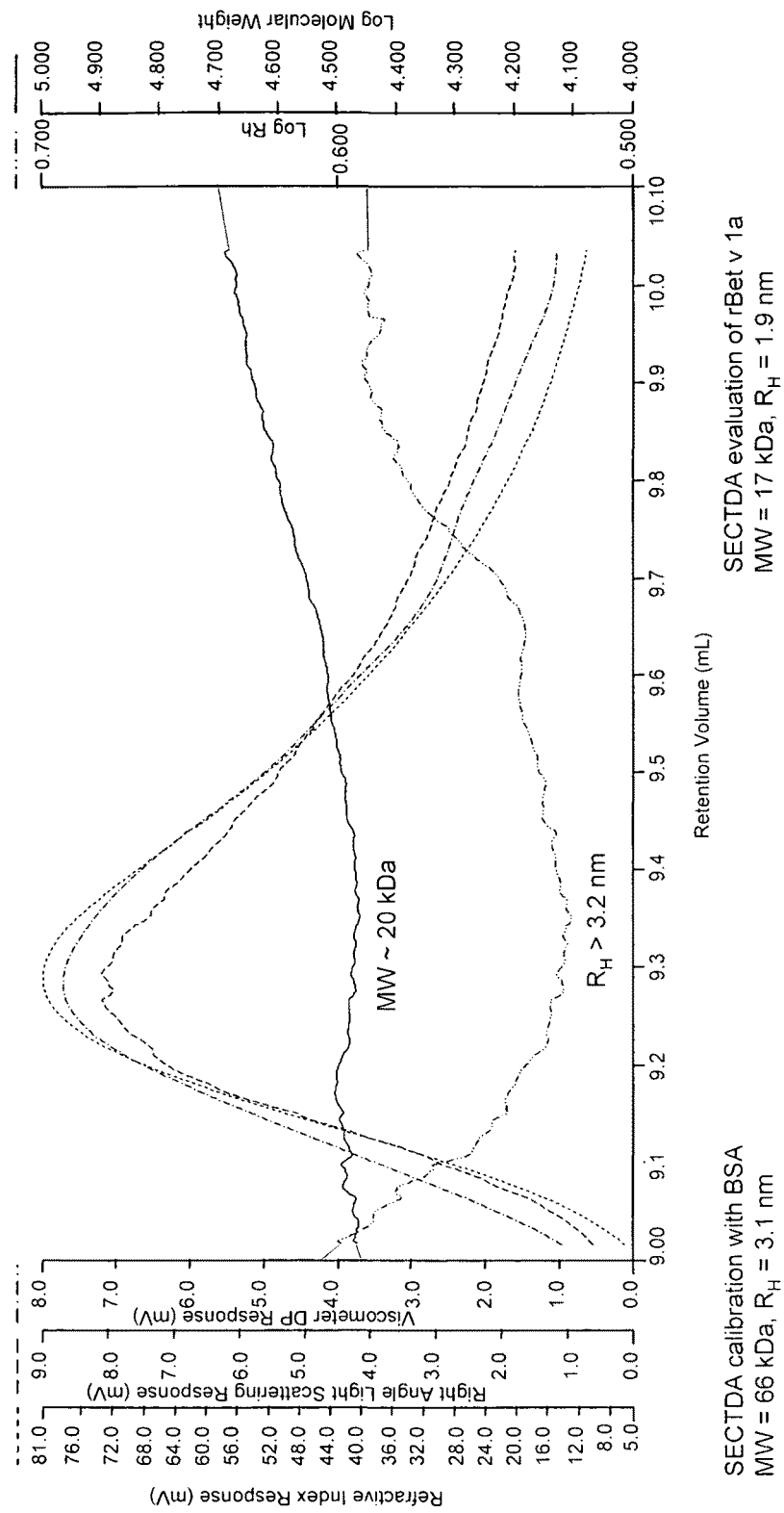
Fig. 18a Homogeneity of BM4 by SECTDA

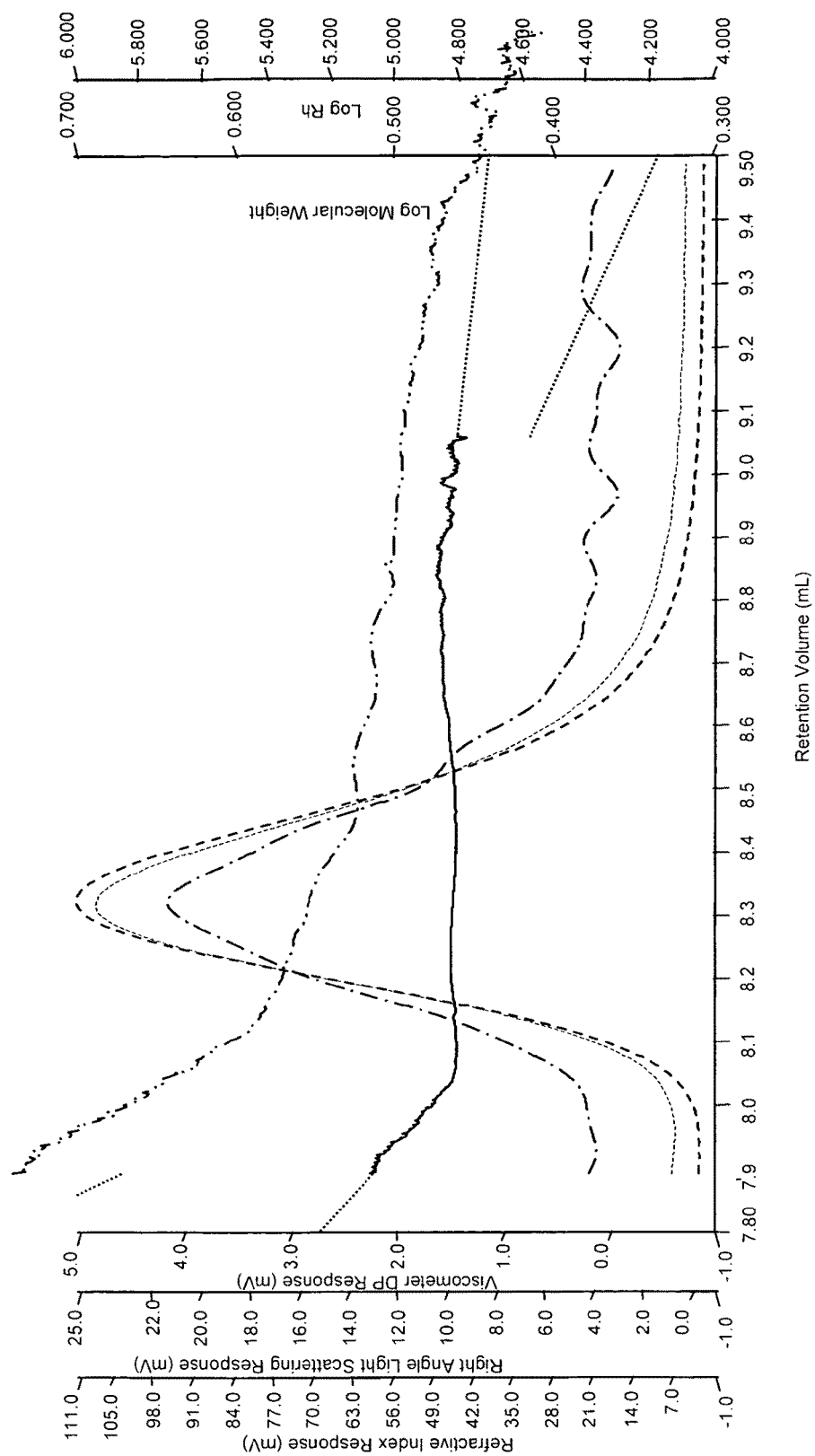
Fig. 18a continuation

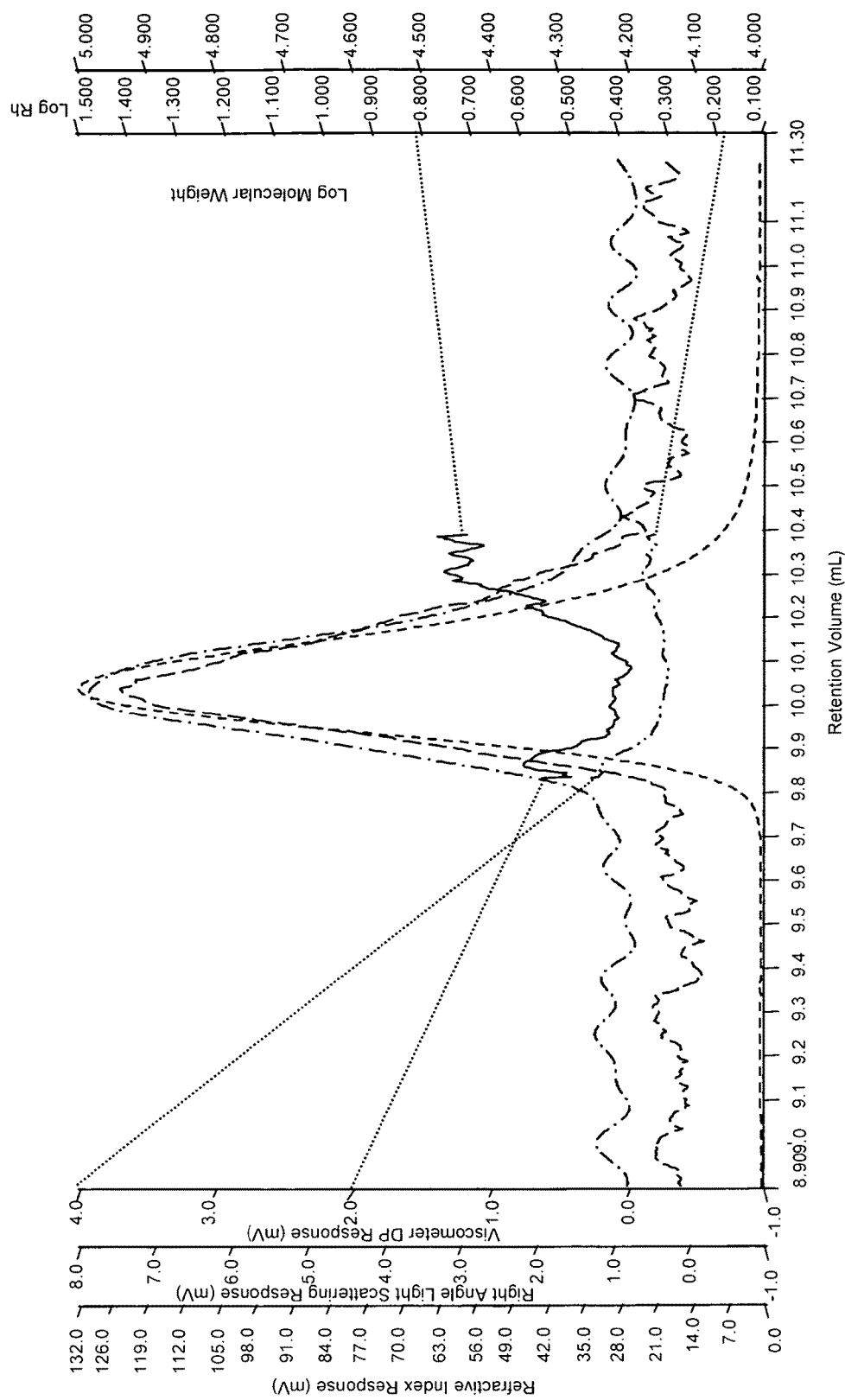
Fig. 18a continuation

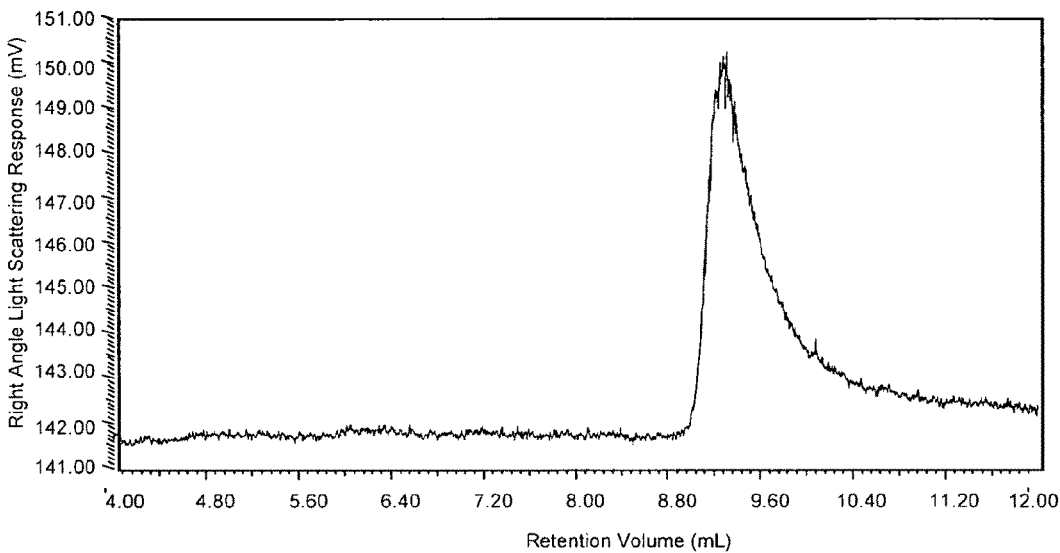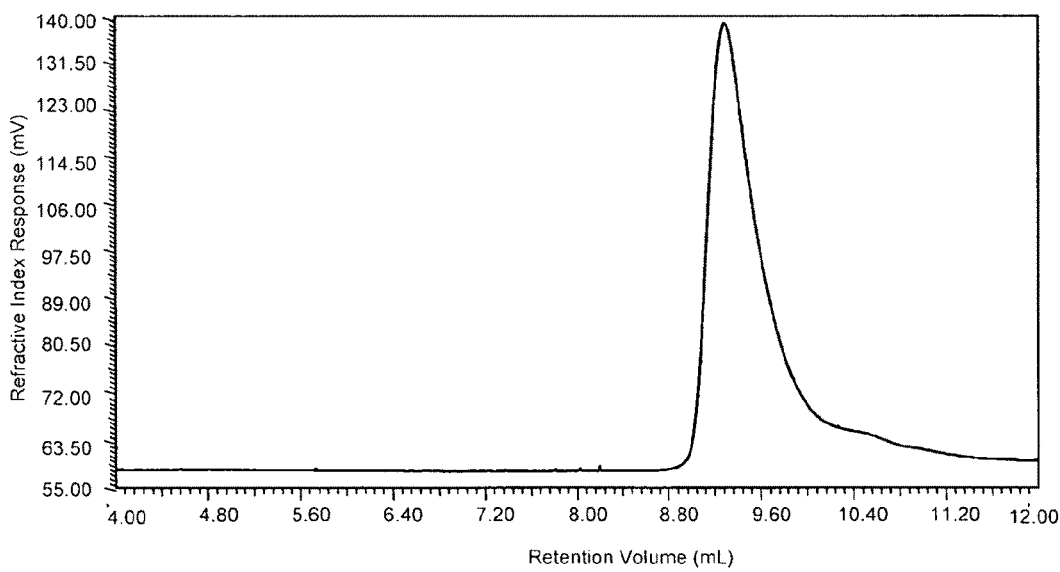
Fig. 18b Homogeneity of BM4 by SECTDA >99% - No aggregation!

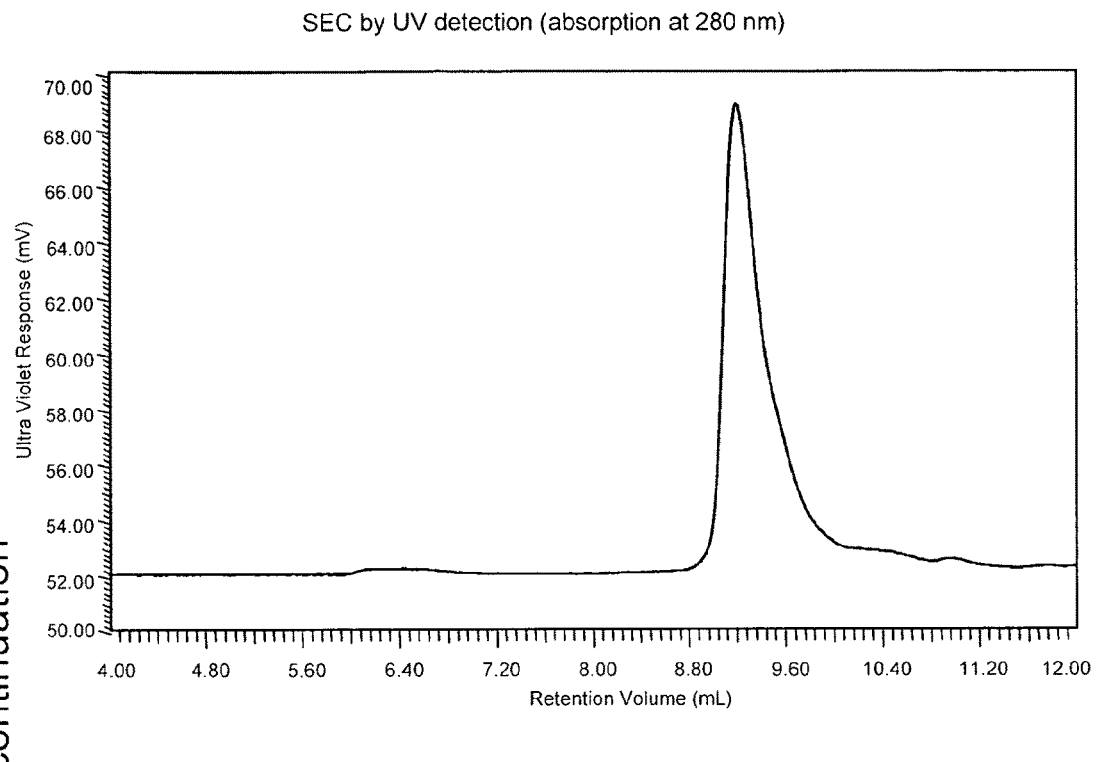
SEC by UV detection (absorption at 280 nm)
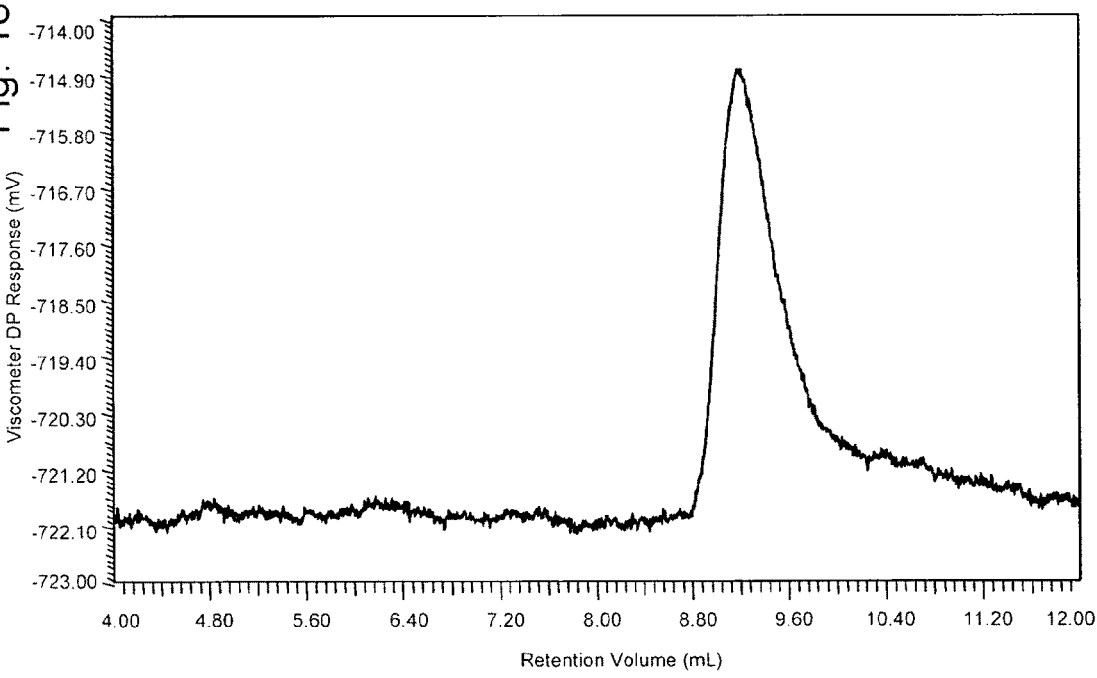
SEC by intrinsic viscosity (IV) detection
Fig. 18b continuation

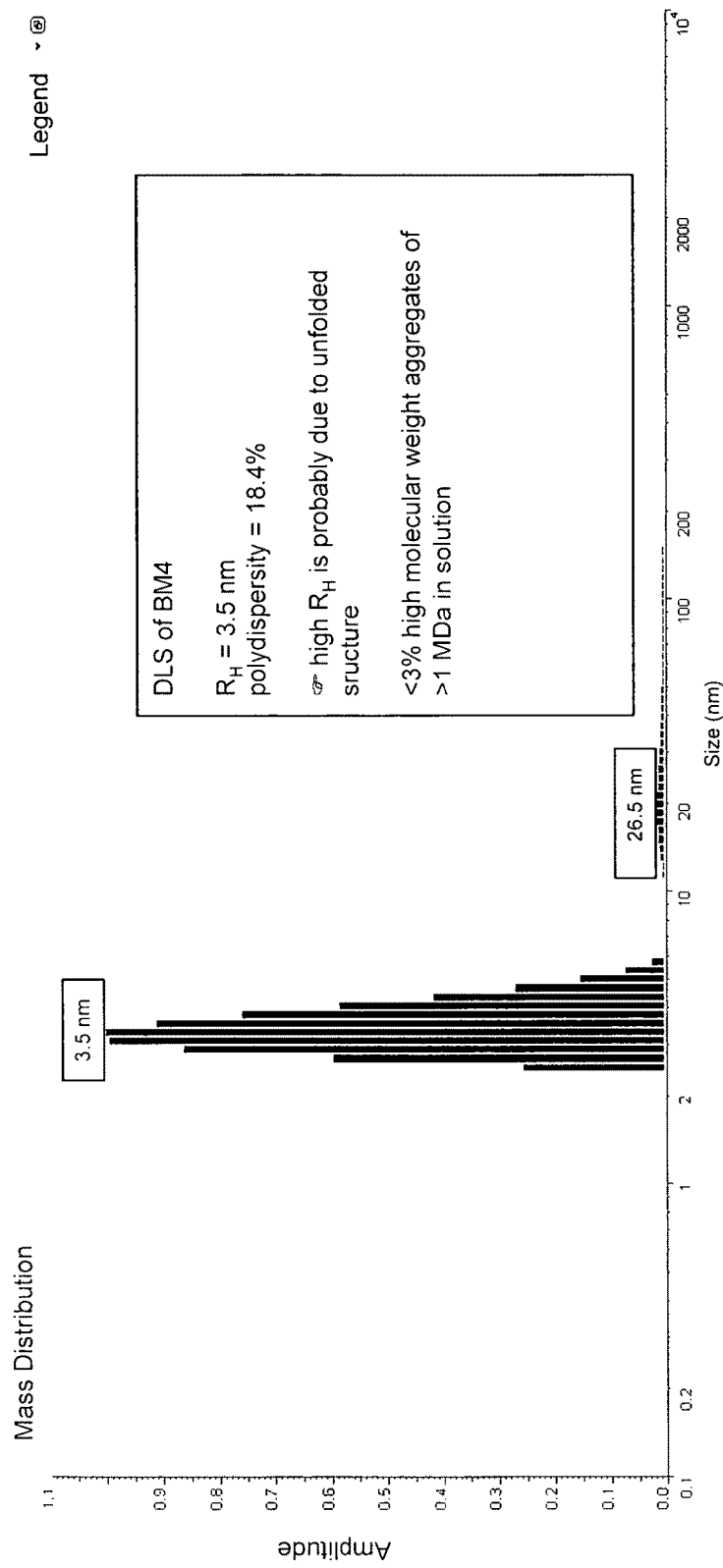
Fig. 19 Aggregation behavior of BM4 in solution by dynamic light scattering Fig. 19 continuation
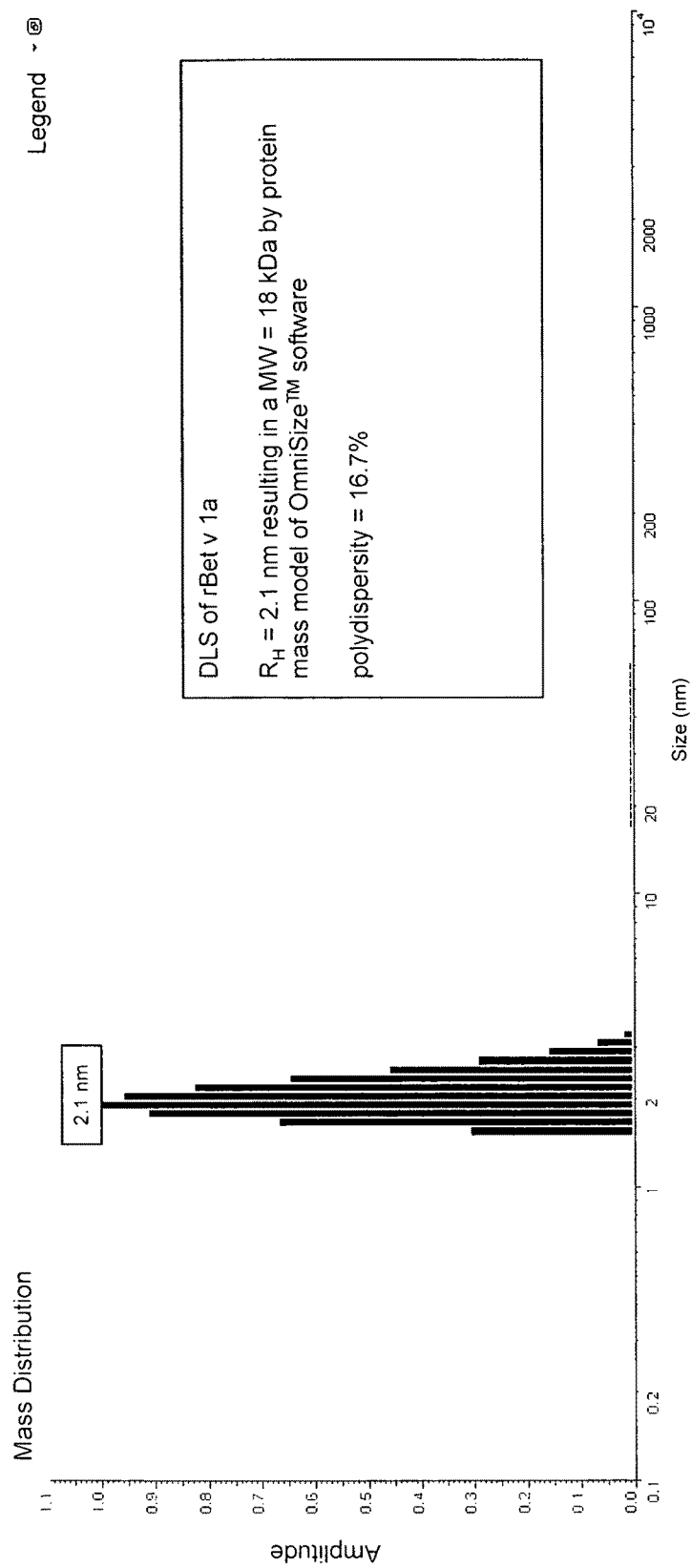

HYPOALLERGENIC MOLECULES

The present invention relates to hypoallergenic molecules.

Worldwide 10-20 million people suffer from pollen allergies and among these patients around one third exhibits allergic reactions towards tree pollen. In the temperate climate zone Bet v 1, the major birch pollen allergen, accounts for most cases of tree pollinosis. Additionally between 50 and 93% of birch pollen allergic individuals develop hypersensitivity reactions towards pollen-related food mediated by cross-reactive IgE antibodies primarily directed against Bet v 1. This type of hypersensitivity is described as pollen-food syndrome (PFS). Thereby allergen contact with the oral mucosa causes immediate adverse reactions usually restricted to the oral cavity and the pharynx. In case of birch pollen allergy one of the allergens most frequently implicated with PFS is Mal d 1, the major apple allergen. Mal d 1 shares 64% amino acid sequence identity with Bet v 1 and cross-inhibition experiments demonstrated the presence of common IgE epitopes on both molecules.

In Ferreira F et al. (FASEB (1998) 12:231-242) the modulation of the IgE reactivity of Bet v is by introducing point mutations in the wild-type Bet v 1a is described. The authors introduced mutations at position 10, 30, 57, 112, 113 and/or 125 of Bet v 1a. Bet v 1a molecules having mutations at these positions do not lead to a complete loss of the three-dimensional structure and thus to an elimination of the IgE reactivity. Mutations at these positions led to decreased IgE reactivity for some patients but not for all, reflecting the polyclonal nature of IgE responses in predisposed individuals. Therefore, such mutations could not be used as an approach to generate therapeutic molecules for the population at large.

In Wallner et al. (Allergy Clin. Immunol., 120(2) (2007): 374-380) chimeric proteins displaying low IgE reactivity and high T-cell reactivity are disclosed which have been selected from a library comprising shuffled allergens of Bet v 1 and Bet v 1 homologous allergens.

In Larsen et al. (Allergy Clin. Immunol., 109(1) (2002): 164) the cross-reactivity between Bet v 1 and Mal d 1 is discussed.

Wallner et al. (Allergy Clin. Immunol., 109(1) (2002):164) refers to in vitro evolution of the Bet v 1 family using gene shuffling methods.

In Bolhaar S T H P et al. (Clin. Exp. Allergy. 35(12) (2005):1638-1644) a hypoallergenic variant of Mal d 1 comprising 5 point mutations is disclosed.

It is an object of the present invention to provide a hypoallergenic molecule which exhibits no or a significantly reduced IgE reactivity compared to the wild-type allergen which may be used to treat pollen-food syndrome caused by Bet v 1a cross reactive allergens.

Therefore, the present invention relates to a hypoallergenic molecule consisting of Bet v 1a (SEQ ID No. 1) or an allergen having at least 40% identity to Bet v 1a comprising mutations of at least four amino acid residues in the region of amino acids 100 to 125 of Bet v 1a or its corresponding region of the allergen having at least 40% identity to Bet v 1a.

It turned out that the mutation of at least four amino residues in the region of amino acids 100 to 125 of Bet v 1a or an allergen having at least 40% identity to Bet v 1a (preferably having an identity of at least 55%, 60%, 65%, 70%, 75% or 80%) results in a hypoallergenic molecule exhibiting a substantially reduced or even complete removal of IgE reactivity due to loss of its three-dimensional structure. The IgE reactivity in the mutated allergen is—compared to the corresponding wild-type allergen reduced. In antibody (IgE)-based biologic assays (e.g. inhibition ELISA or RAST, basophil inflammatory mediator release), at least 50, preferably at least 100, more preferably at least 500, even more preferred at least 1000 fold higher concentrations of the mutated allergen is required to reach half-maximal values obtained with wild type allergen. This is in the light of Ferreira F et al. (FASEB (1998) 12:231-242) surprising because therein it was shown that the mutation of three amino acid residues in this region did not result in a hypoallergenic molecule with the properties of the molecule of the present invention.

The hypoallergenic properties of the hypoallergenic molecules of the present invention are a consequence of the destruction of the three-dimensional structure compared to the wild-type allergen. It has been demonstrated by Akdis et al. (Akdis C A et al. Eur J Immunol. 28(3)(1998):914-25) that a native folded allergen, here the bee venom allergen phospholipase A (PLA), induced a different immune response as the non-native folded version of the very same protein. Folded PLA induced IgE antibodies in B cells and stimulated T helper (TH) 2 cells, both markers of an allergic immune response, whereas non-refolded or reduced-and-alkylated PLA both induced a TH1 dominated cytokine profile leading to an IgG4 response in B cells. A TH1 driven immune response is clearly favoured for molecules, which should be used as therapeutic agents for allergic diseases. Therefore, the unfolded nature of the molecules of the present invention is crucial.

It is in particular preferred to mutate, next to three other amino acid residues, at least amino acid residue 113 or 114 of Bet v 1a or an allergen having at least 40% identity to Bet v 1a.

Another aspect of the present invention relates to a hypoallergenic molecule consisting of Bet v 1a or an allergen having at least 40% identity to Bet v 1a comprising mutations of at least one amino acid residue in the region of amino acids 100 to 125 of Bet v 1a of its corresponding region of the allergen having at least 40% identity to Bet v 1a, wherein the mutation of at least one amino acid residue comprises the mutation of amino acid residue at position 114 of Bet v 1a or the allergen having at least 40% identity to Bet v 1a.

It surprisingly turned out that the mutation of at least amino acid residue 114 may already lead to a hypoallergenic molecule having a three-dimensional structure being different to the corresponding wild-type allergen. The mutation of amino acid 114 of Bet v 1a or an allergen being at least 40% identity to Bet v 1a will lead to a hypoallergenic molecule. According to a preferred embodiment of the present invention this hypoallergenic molecule will comprise at least one (preferably at least two, three, four, five) further mutations within amino acids 100 to 125 of Bet v 1a or its corresponding region of allergen having at least 40% identity to Bet v 1a. Particularly preferred the hypoallergenic molecule comprises a mutation at amino acid residue 102 and/or 120 of Bet v 1a. In a particular preferred embodiment of the present invention amino acid residue 114 of Bet v 1a or an allergen having at least 40% identity to Bet v 1a is substituted by lysine (K), aspartic acid (D) or glutamic acid (E).

According to a preferred embodiment of the present invention the allergen having at least 40% identity to Bet v 1a is immunologically cross-reactive with Bet v 1a. Here immunologic cross-reactivity is defined by antibody binding to a certain molecule and can be determined by ELISA using affinity purified polyclonal rabbit anti Bet v 1a antibodies. Molecules having at least 40% identity to Bet v 1a and being recognized by these antibodies will be considered as immunological cross-reactive with Bet v 1a.

It is advantageous that the allergen having at least 40% identity to Bet v 1a is immunologically cross-reactive with Bet v 1a because in this case the hypoallergenic molecule of the present invention can be used to prevent or treat pollen-food syndrome (PFS), because the immune system is able to produce antibodies which are able to bind to Bet v 1a as well as to food allergens, which in many cases shows at least 40% identity to Bet v 1a.

It is even more advantageous when the allergen has at least 85%, preferably at least 90%, more preferably at least 95%, identity to Bet v 1a.

The term "identity", as used herein, indicates whether any two (or more) peptide, polypeptide or protein sequences have amino acid sequences that are "identical" to a certain degree ("% identity") to each other. This degree can be determined using known computer algorithms such as the "FASTA" program, using for example, the default parameters as in Pearson et al. (1988) PNAS USA 85: 2444 (other programs include the GCG program package (Devereux, J., et al., Nucleic Acids Research (1984) Nucleic Acids Res., 12, 387-395), BLASTP, BLASTN, FASTA (Atschul, S. F., et al., J Molec Biol 215: 403 (1990); Guide to Huge Computers, Martin J. Bishop, ed., Academic Press, San Diego, 1994, and Carillo et al, (1988) SIAM J Applied Math 48: 1073). For instance, the BLAST tool of the NCBI database can be used to determine identity. Other commercially or publicly available programs include, DNAStar "MegAlign" program (Madison, Wis.) and the University of Wisconsin Genetics Computer Group (UWG) "Gap" program (Madison, Wis.)). Percent identity of protein molecules can further be determined, for example, by comparing sequence information using a GAP computer program (e.g. Needleman et al., (1970) J. Mol. Biol. 48:443, as revised by Smith and Waterman (1981) Adv. Appl. Math. 2:482). Briefly, the GAP program defines identity as the number of aligned symbols (i.e., nucleotides or amino acids) which are identical, divided by the total number of symbols in the shorter one of the two sequences. Default parameters for the GAP program can include: (1) a unary comparison matrix (containing a value of 1 for identities and for non-identities) and the weighted comparison matrix of Gribskov et al. 14:6745, as described by Schwartz and Dayhoff, eds., ATLAS OF PROTEIN SEQUENCE AND STRUCTURE, National Biomedical Research Foundation, pp. 353-358 (1979); (2) a penalty of 3.0 for each gap and an additional 0.10 penalty for each symbol in each gap; and (3) no penalty for end gaps.

The allergen having at least 40% identity to Bet v 1a (Z80098) is preferably composed of Bet v 1 and an allergen selected from the group consisting of Dau c 1, in particular Dau c 1.0101 (U47087), Dau c 1.0102 (D88388), Dau c 1.0104 (Z81362), Dau c 1.0105 (Z84376) , Dau c 1.0201 (AF456481) or Dau c 1.0103 (Z81361) , Api g 1, in particular Api g 1.0101 (Z48967) or Api g 1.0201 (Z75662) , Pet c 1 (X12573) , Cas s 1 (AJ417550) (SEQ ID NO:120), Que a 1 (P85126), Mal d 1 (SEQ ID NO:2), in particular Mal d 1.0101 (X83672) (SEQ ID NO:187), Mal d 1.0102 (Z48969) (SEQ ID NO:188), Mal d 1.0109 (AY026910) (SEQ ID NO:195), Mal d 1.0105 (AF124830) (SEQ ID NO:191) , Mal d 1.0106 (AF124831) (SEQ ID NO:192), Mal d 1.0108 (AF126402) (SEQ ID NO:194), Mal d 1.0103 (AF124823) (SEQ ID NO:189), Mal d 1.0107 (AF124832) (SEQ ID NO:193), Mal d 1.0104 (AF124829) (SEQ ID NO:190), Mal d 1.0201 (L42952) (SEQ ID NO:196), Mal d 1.0202 (AF124822) (SEQ ID NO:197), Mal d 1.0203 (AF124824) (SEQ ID NO:198), Mal d 1.0207 (AY026911) (SEQ ID NO:202), Mal d 1.0205 (AF124835) (SEQ ID NO:200), Mal d 1.0204 (AF124825) (SEQ ID NO:199), Mal d 1.0206 (AF020542) (SEQ ID NO:201), Mal d 1.0208 (AJ488060) (SEQ ID NO:203), Mal d 1.0302 (AY026908) (SEQ ID NO:121), Mal d 1.0304 (AY186248) SEQ ID NO:122) , Mal d 1.0303 (AY026909) (SEQ ID NO:204), Mal d 1.0301 (Z72425) (SEQ ID NO:123), Mal d 1.0402 (Z72427) (SEQ ID NO:124) , Mal d 1.0403 (Z72428) (SEQ ID NO:125) or Mal d 1.0401 (Z72426) (SEQ ID NO:126) , Pyr c 1, in particular Pyr c 1.0101 (065200) , Pru av 1, in particular Pru av 1.0101 (U66076) , Pru av 1.0202 (AY540508), Pru av 1.0203 (AY540509) or Pru av 1.0201 (AY540507) , Pru p 1 (DQ251187), Rub i 1.0101 (DQ660361), Pru ar 1, in particular Pru ar 1.0101 (U93165) , Cor a 1, in particular Cor a 1.0401 (AF136945) , Cor a 1.0404 (AF323975) (SEQ ID NO:129), Cor a 1.0402 (AF323973) (SEQ ID NO:130), Cor a 1.0403 (AF323974) (SEQ ID NO:131), Cor a 1.0301 (Z72440) (SEQ ID NO:132), Cor a 1.0201 (Z72439) (SEQ ID NO:133), Cor a 1/5 (X70999) (SEQ ID NO:134), Cor a 1/11 (X70997) (SEQ ID NO:135), Cor a 1/6 (X71000) (SEQ ID NO:136) or Cor a 1/16 (X70998) (SEQ ID NO:137), Bet v 1d (X77266) (SEQ ID NO:138), Bet v 11 (X77273) (SEQ ID NO:139), Bet v 1a1-6 (Ferreira F et al. FASEB (1998) 12:231-242) , Bet v 1g (X77269) (SEQ ID NO:140), Bet v 1f (X77268) (SEQ ID NO:141), Bet v 1jj (X77271) (SEQ ID NO:142), Bet v 1e (X77267) (SEQ ID NO:143), Bet v 1b (X77200) (SEQ ID NO:144), Bet v 1c (X77265) (SEQ ID NO:145), Bet v 1.0101 (X15877) (SEQ ID NO:146), Bet v 1.0901 (X77272) (SEQ ID NO:147), Bet v 1.1101 (X77599) (SEQ ID NO:148), Bet v 1.1201 (X77600) (SEQ ID NO:149), Bet v 1.1301 (X77601) (SEQ ID NO:150) , Bet v 1.1401 (X81972) (SEQ ID NO:151), Bet v 1.1501 (Z72429) (SEQ ID NO:152), Bet v 1.1601 (Z72437) (SEQ ID NO:153), Bet v 1.1701 (Z72430) (SEQ ID NO:154), Bet v 1.1801 (Z72431) (SEQ ID NO:155), Bet v 1.1901 (Z72433) (SEQ ID NO:156), Bet v 1.2001 (Z72434) (SEQ ID NO:157), Bet v 1.2101 (Z72435) (SEQ ID NO:158), Bet v 1.2201 (Z72438) (SEQ ID NO:159), Bet v 1.2301 (Z72436) (SEQ ID NO:160), Bet v 1.2401 (Z80100) (SEQ ID NO:161), Bet v 1.2501 (Z80101) (SEQ ID NO:162), Bet v 1.2601 (Z80102) (SEQ ID NO:163), Bet v 1.2701 (Z80103) (SEQ ID NO:164), Bet v 1.2901 (Z80105) (SEQ ID NO:165), Bet v 1.3001 (Z80106) (SEQ ID NO:166), Aln g 1 (S50892) (SEQ ID NO:167), Car b 1, in particular Car b 1.0301 (Z80169) (SEQ ID NO:168), Car b 1.0302 (Z80170) (SEQ ID NO:169), Car b 1.0103 (Z80159) (SEQ ID NO:170), Car b 1.0105 (Z80161) (SEQ ID NO:171), Car b 1.0104 (Z80160) (SEQ ID NO:172), Car b 1/1a, Car b 1.0101 (X66932) (SEQ ID NO:173), Car b 1.0102 (X66918) (SEQ ID NO:174), Car b 1/1b, Car b 1/2, Car b 1.0106a (Z80162) (SEQ ID NO:175), Car b 1.0106b (Z80163) (SEQ ID NO:176), Car b 1.0106c (Z80164) (SEQ ID NO:177), Car b 1.0106d (Z80165) (SEQ ID NO:178), Car b 1.0107a (Z80166) (SEQ ID NO:179), Car b 1.0107b (Z80167) (SEQ ID NO:180), Car b 1.0201 (X66933) (SEQ ID NO:181) or Car b 1.0108 (Z80168) (SEQ ID NO:182), Gly m 4.0101 (X60043), Vig r 1.0101 (AY792956) , Ara h 8.0101 (AY328088), Asp ao PR10 (X62103) , Bet p 1a (AB046540) (SEQ ID NO:183), Bet p 1b (AB046541) (SEQ ID NO:184), Bet p 1c (AB046542) (SEQ ID NO:185), Fag s 1 (AJ130889) (SEQ ID NO:186), Cap ch 171(D a (AJ879115) , Cap ch 17kD b (AJ878871) , Fra a 1.0101 (AY679601), Tar o 18kD (AF036931).

Particularly suited is Mal d 1 (SEQ ID No. 2).

According to a preferred embodiment of the present invention the at least one mutation of at least four amino acid residues is an amino acid substitution, deletion or addition.

The mutation of the at least four amino acid residues within the allergen may be of any kind. However, it is preferred to substitute single amino acid residues or stretches of amino acid residues within the molecule, because in such a case the length of the hypoallergenic molecule is not affected at all compared to Bet v 1a.

According to a preferred embodiment of the present invention the mutated region of Bet v 1a or its corresponding region of the allergen having at least 40% identity to Bet v 1a comprises amino acids 105 to 120, preferably amino acids 108 to 118, more preferably amino acids 109 to 116, of Bet v 1a or its corresponding region of the allergen having at least 40% identity to Bet v 1a.

According to a preferred embodiment of the present invention the at least one mutation comprises the substitution of said region with the corresponding region of another allergen selected from the group consisting of Bet v 1a and an allergen having at least 40% identity to Bet v 1a.

Due to the substitutions of said regions it is possible not only to create a hypoallergenic molecule which comprises T-cell epitopes of Bet v 1a or an allergen having at least 40% identity to Bet v 1a but also molecules comprising potentially specific Bet v 1a epitopes or epitopes of the allergen having at least 40% identity to Bet v 1a. This allows administering to an individual suffering or being at risk to suffer a pollen-food allergy a vaccine comprising said hypoallergenic molecule, which is able to provoke the formation of an immune response not only against a first allergen but also against a second allergen.

According to another preferred embodiment of the present invention the molecule consists of Bet v 1 and the region of amino acids 109 to 116 of Bet v 1 is substituted with the corresponding region of Mal d 1 (resulting in SEQ ID No. 3).

According to a particular preferred embodiment of the present invention the molecule consists of Mal d 1 and the region of amino acids 109 to 116 of Mal d 1 is substituted with the corresponding region of Bet v 1.

Bet v 1a or an allergen sharing at least 40% identity with Bet v 1a may be modified by substituting at least a part of said defined region with an amino acid fragment which can be derived from another allergen, whereby said fragment is of the same region as of the region to be substituted.

Another aspect of the present invention relates to a nucleic acid molecule encoding a hypoallergenic molecule according to the present invention.

A further aspect of the present invention relates to a vector comprising a nucleic acid molecule according to the present invention.

The vector of the present invention comprises a nucleic acid fragment encoding for the hypoallergenic molecule of the present invention and vector elements which allow its reproduction in prokaryotic (e.g. bacteria) organisms. These vectors comprise functional polynucleotide sequences such as promoters, transcriptional binding sites etc. The vector may be a plasmid or viral vector.

In order to facilitate the purification of the hypoallergenic molecule, said molecule may be fused to a Tag, in particular to a histidine or gluthathione-S-transferase. Hence, suited expression vectors known in the art may be used.

Another aspect of the present invention relates to a vaccine preparation comprising a hypoallergenic molecule according to the present invention.

According to a preferred embodiment of the present invention said preparation comprises further at least one pharmaceutically acceptable excipient, diluent, adjuvant and/or carrier.

In order to provide a vaccine formulation which can be administered subcutaneously, intramuscularly, intravenously, mucosally etc. to an individual the formulation has to comprise further excipients, diluents, adjuvants and/or carriers. Preferred adjuvants used comprise KLH (keyhole-limpet hemocyanin) and alum. Suitable protocols for the production of vaccine formulations are known to the person skilled in the art and can be found e.g. in "Vaccine Protocols" (A. Robinson, M. P. Cranage, M. Hudson; Humana Press Inc., U.S.; $2^{nd}$ edition 2003).

Another aspect of the present invention relates to the use of hypoallergenic molecule according to the present invention for the manufacture of a vaccine for the prevention and/or treatment of allergies.

The hypoallergenic molecule of the present invention can be used for treating and preventing allergies, in particular allergies associated with pollen-food syndrome, where patients suffering from pollinosis also experience food allergies (these may provoke e.g. itching and pruritus around the oral cavity to generalized urticaria and even anaphylaxis). In the pollen-food syndrome, an individual is first sensitized by inhaling allergens present in pollen. Thereafter, immediate-type symptoms begin to be provoked when the individual gets in contact with any plant-derived foods containing proteins cross-reactive to the sensitizing allergen. After the completion of per-oral sensitization, allergic symptoms are provoked whenever the patient gets in contact with the same protein. Bet v 1a is a highly cross-reactive allergen which is able to cross-react with a large number of food derived allergens, in particular derived from vegetables and fruits. Therefore, an individual suffering from a pollen allergy caused by Bet v 1a may also be allergic to food derived allergies.

The present invention is further illustrated by the following figures and examples, however, without being restricted thereto.

FIG. 1 shows (A) a schematic representation of the 160 amino acids long (including initiation methionine) mutant allergen BM1,2,3,5. The protein was constructed by grafting epitopes of Mal d 1.0108 consisting of 7 consecutive amino acids on the template allergen Bet v 1a. Stretches matching amino acids of Bet v 1a are shown in white, epitopes inserted from Mal d 1.0108 in grey. Amino acids composing the exchanged epitopes are listed in one-letter code. Residues identical in both proteins are presented in black, different amino acids in grey. (B) A model of BM1,2,3,5 was calculated and the structure was compared to the 3-dimensional fold of Bet v 1. Residues identical in BM1,2,3,5 and Bet v 1a are shown in grey, epitopes derived from Mal d 1.0108 are presented in black. The lower panel shows the proteins rotated by 180° C. (C) Secondary structure of BM1,2,3,5 was compared to Bet v 1 by circular dichroism (CD). Data is presented as mean residue molar ellipticity [θ] MRW at a given wavelength and baseline-corrected.

Figure 2:
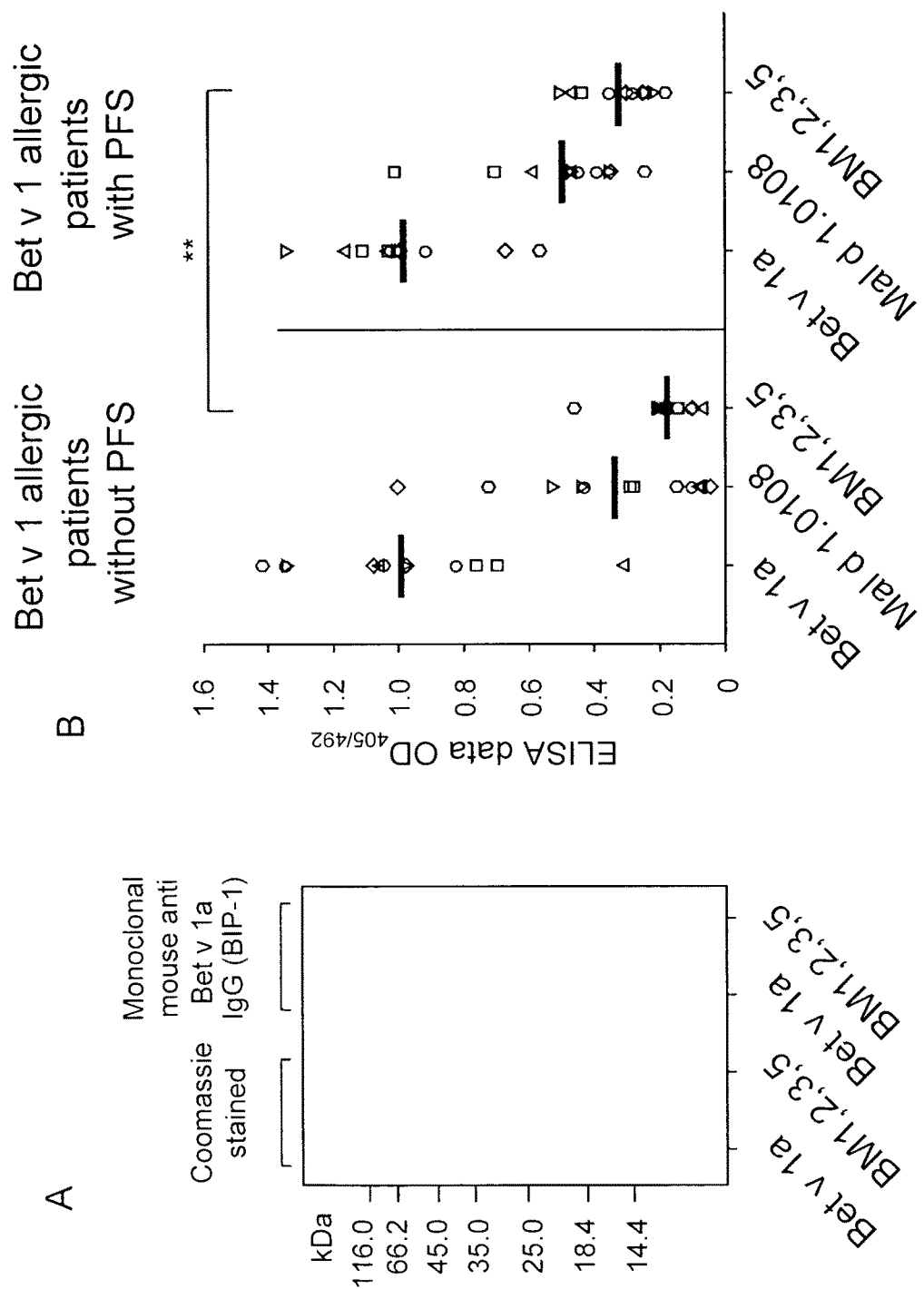

FIG. 2 shows (A) an SDS-PAGE and immunoblot analysis of affinity purified BM1,2,3,5 (each 5 µg per lane). Following SDS-PAGE proteins were visualized by Coomassie Brilliant Blue staining (left panel). For immunoblot analysis proteins were detected using a monoclonal mouse anti Bet v 1 antibody. (B) In ELISA IgE binding activity of Bet v 1a, Mal d 1.0108 and BM1,2,3,5 was assessed using sera of Bet v 1 allergic patients without clinical symptoms of PFS (n=12) or Bet v 1 allergic patients, suffering from PFS to apple and other Bet v 1-related foods (n=11). Allergens were titrated for coating and optimal antigen coating concentration was determined to be 0.5 mg/ml. No significant difference was observed for both groups of patients concerning IgE binding towards Bet v 1 (P>0.99). As expected, IgE binding towards Mal d 1 was stronger in the PFS group. Concerning the mutant BM1,2,3,5 patients with PFS showed significantly increased IgE binding (P<0.01). Symbols represent individual patients, bars means. P-values were calculated by t-test (**P<0.01).

FIG. 3 shows schematically the mutant allergen BM4 according to example 2.

FIG. 4 shows a clustal W alignment of Bet v 1a and BM4. The exchanged epitope of BM4 is underlined, the immunodominant T cell epitope of Bet v 1a is indicated in italic and bold. Amino acids in bold represent the "core" of the epitope exchange, which are amino acids found to be critical for patients' IgE binding of Bet v 1.

FIG. 5 shows a clustal W alignment of Mal d 1.0108 and BM4. The exchanged epitope of BM4 is underlined. Amino acids in bold represent the "core" of the epitope exchange, which are amino acids found to be critical for patients' IgE binding of Bet v 1.

FIG. 6 shows a SDS-Page of BM4.

Figure 7:
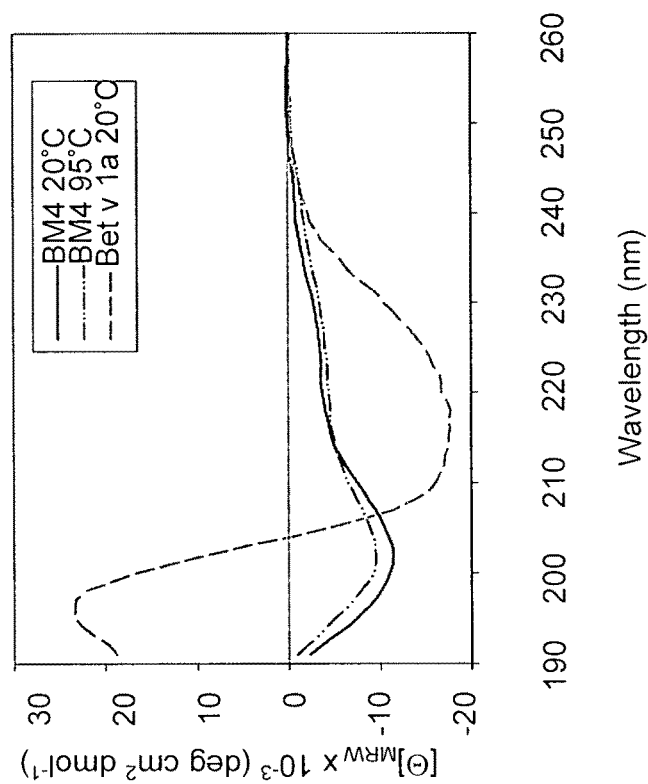

FIG. 7 shows CD spectra of Bet v 1a in comparison to BM4 at 20° C. and at 95° C. All curves are baseline corrected; data are presented as mean residue molar ellipticity. Protein concentrations were determined by amino acid analysis. BM4 shows the typical CD spectrum of random-coiled proteins at 20° C. as well as at 95° C.

Figure 8:
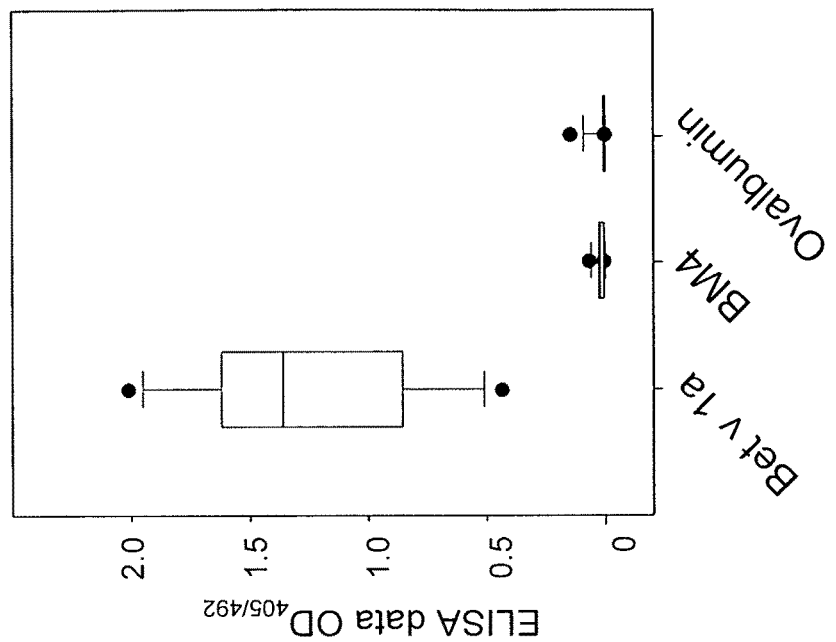

FIG. 8 shows an ELISA of Bet v 1a (Biomay), BM4 and ovalbumin. Ovalbumin was purchased from Sigma-Aldrich as irrelevant control antigen. Allergens (200 ng/well) were immobilized to the solid phase. All measurements were performed as duplicates; results are presented as mean OD values after background subtraction. Sera of 13 birch pollen allergic individuals were tested. As control NHS was uses which gave no signal to any of the proteins. BM4 shows virtually no patients' IgE binding in the ELISA.

Figure 9:
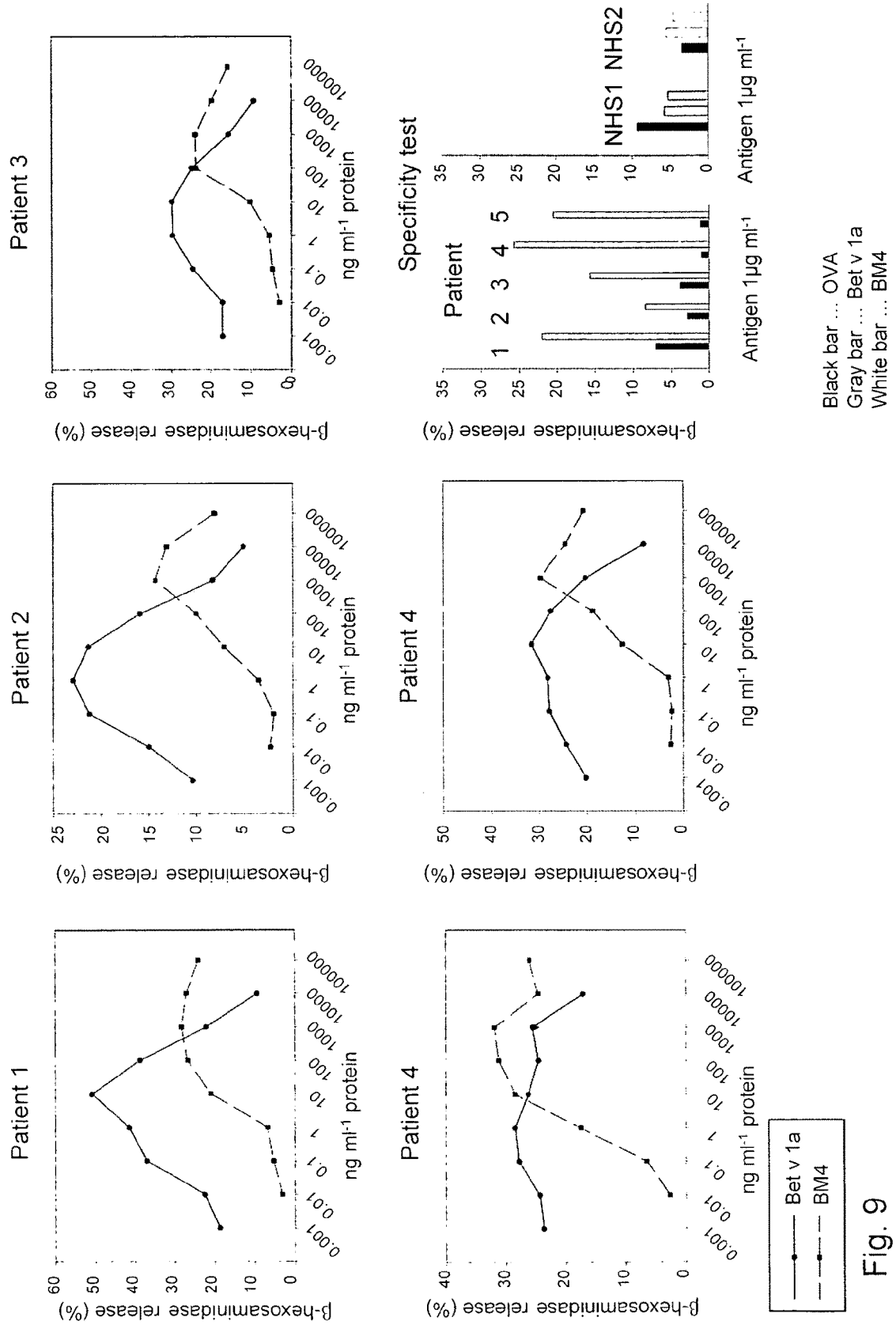

FIG. 9 shows the allergenic activity of BM4 assessed by sensitizing huFcεRI-transfected RBL-2H3 cells with serum IgE from birch pollen-allergic patients. BM4 shows a 100-1000 fold reduced anaphylactic activity as compared to Bet v 1a.

Figure 10:
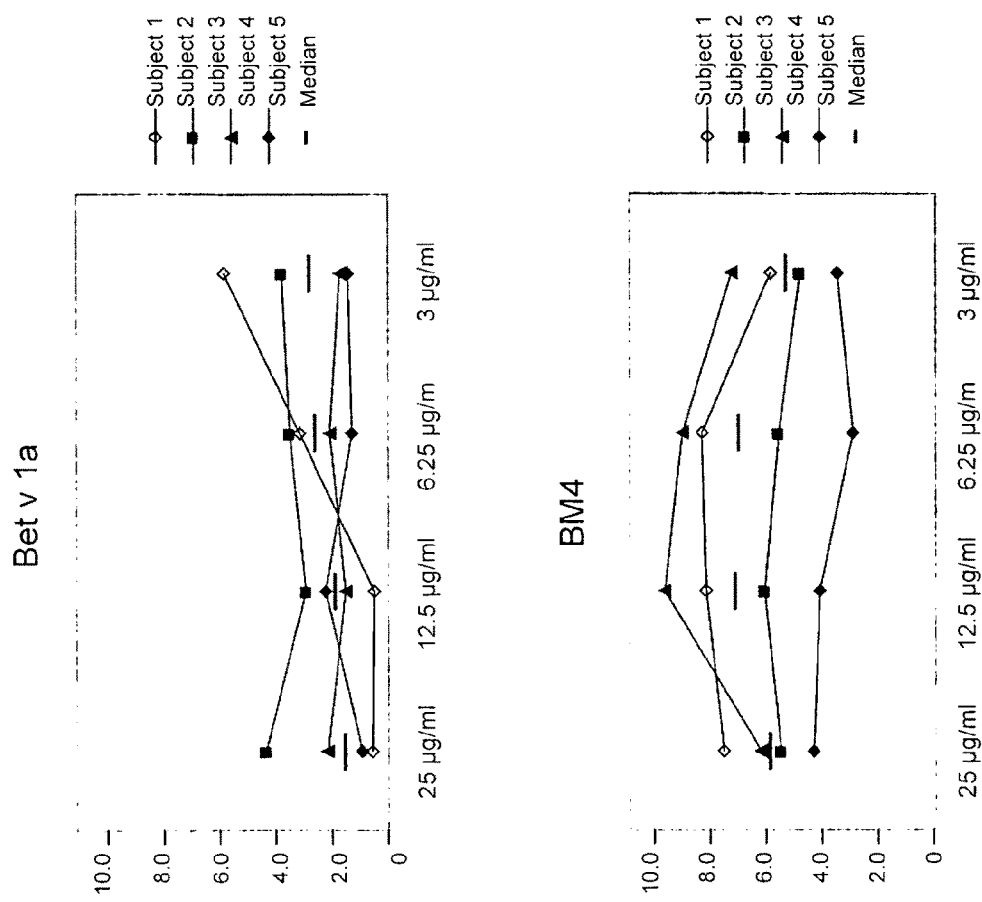

FIG. 10 shows the determination of proliferative responses of peripheral blood mononuclear cells (PBMCs) from birch pollen allergic patients stimulated with 25, 12.5, 6.25 or 3 μg/ml of 6×his tagged BM4 or Bet v 1a. Average stimulation indices (SI) of BM4 were found to be higher than of Bet v 1a. Symbols represent individual patients, bars medians.

Figure 11:
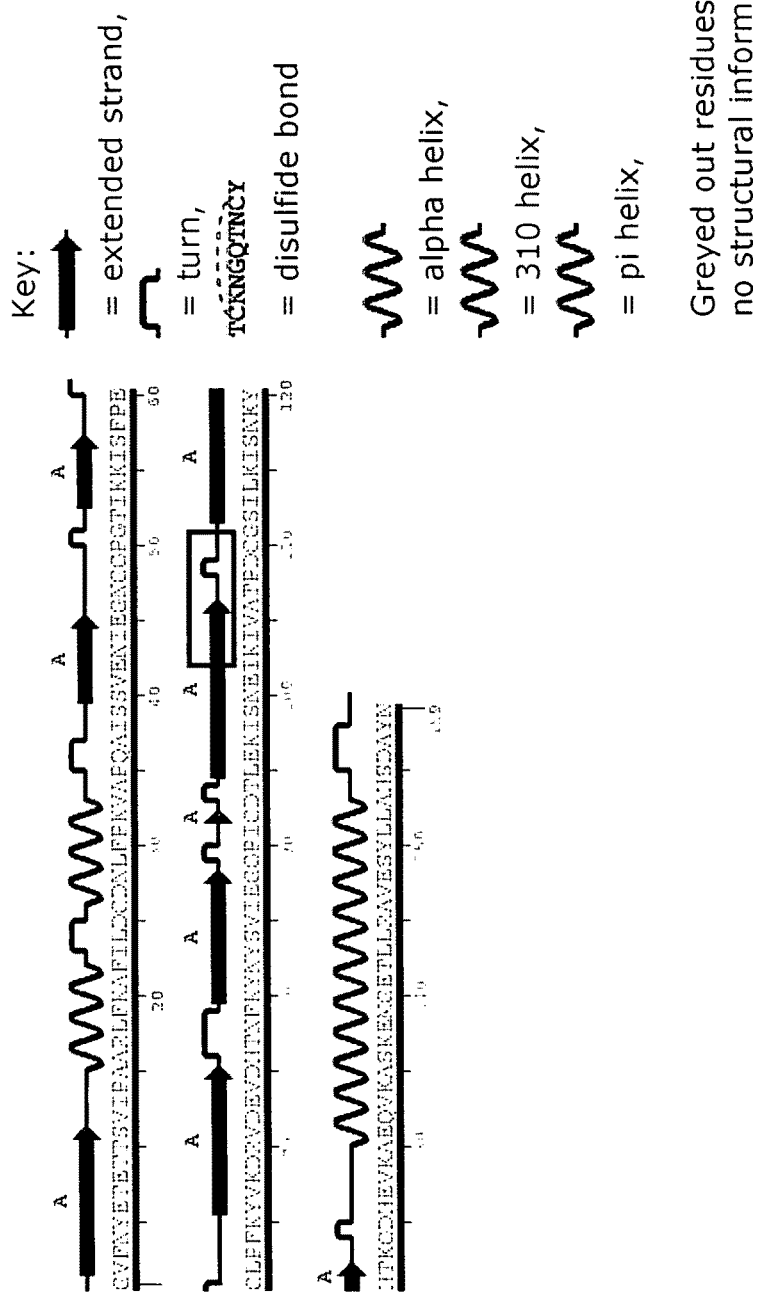

FIG. 11 shows the sequence of Bet v 1 (1bv1) obtained from the PDB protein data bank. The sequence area which has been replaced in the mutant protein BM4 is indicated by a box.

FIG. 12 shows the sequence area which has been replaced in the mutant protein BM4 (SEQ ID NO:3) and aligned with the sequence of Bet v 1a (SEQ ID NO:1). A relevant T cell epitope of Bet v 1 (SILKISNKYHTK; SEQ ID NO. 4) recognized by 41% of the patients is indicated in italic and bold. One peptide before (DGGSILKISNK; SEQ ID NO. 5) is the recognized by 6%, the peptide after (KISNKYHTKGDH; SEQ ID No. 6) by none of the patients. The PBMC data so far did not show a reduced but rather a better T cell stimulation. Therefore no problems regarding T cell stimulation properties of BM4 can be expected.

FIG. 13 shows a Clustal W multiple sequence alignment of Bet v 1 and its homologous allergens found in other pollen sources, fruits, nuts or vegetables, including isoforms. The epitope replaced in Bet v 1a was replaced by the one of Mal d 1.0108 in BM9

Figure 14:
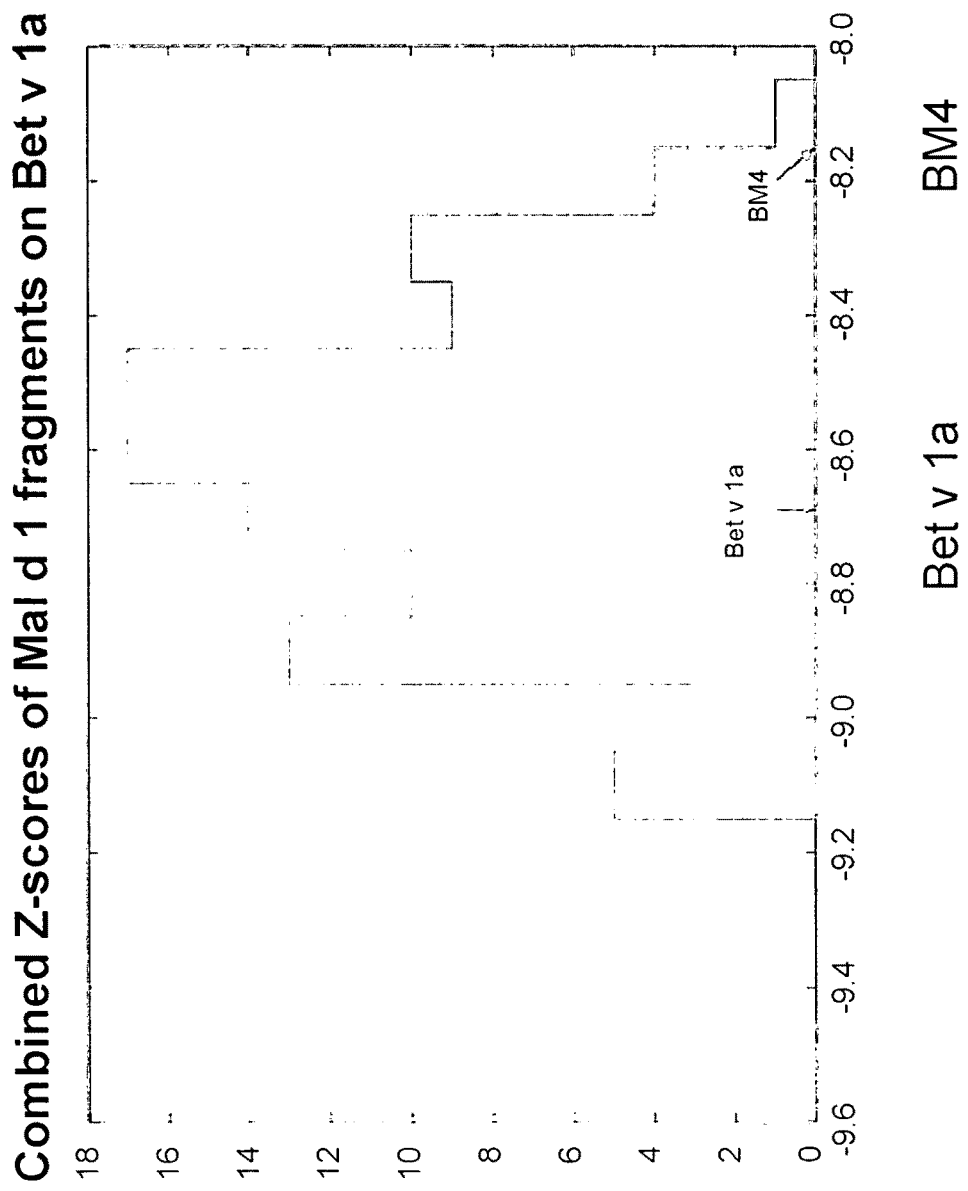

FIG. 14 shows a calculation of Z-scores of different Bet v 1a mutants with grafted epitopes of Mal d 1.0108. Therefore overlapping non-sequence identical stretches (10aa; n=103) of Mal d 1.0108 were substituted on the Bet v 1a structure and Z-scores were calculated using the software tool ProSa II. This software uses knowledge-based potentials derived from known protein structures and captures the average properties of native globular proteins in terms of atom-pair and solvent interactions to generate scores reflecting the quality of protein structures (Sippl M. J, Proteins 17:355-362, 1993). The calculations revealed that the epitopes substitution of the amino acids 109-116 (SGSTIKSI; SEQ ID No. 7) of Mal d 1.0108 on Bet v 1a is one of the most destabilizing substitutions giving a high Z-score. With regard to protein structure this explains the unfolded nature of the mutant allergen BM4.

Figure 15:
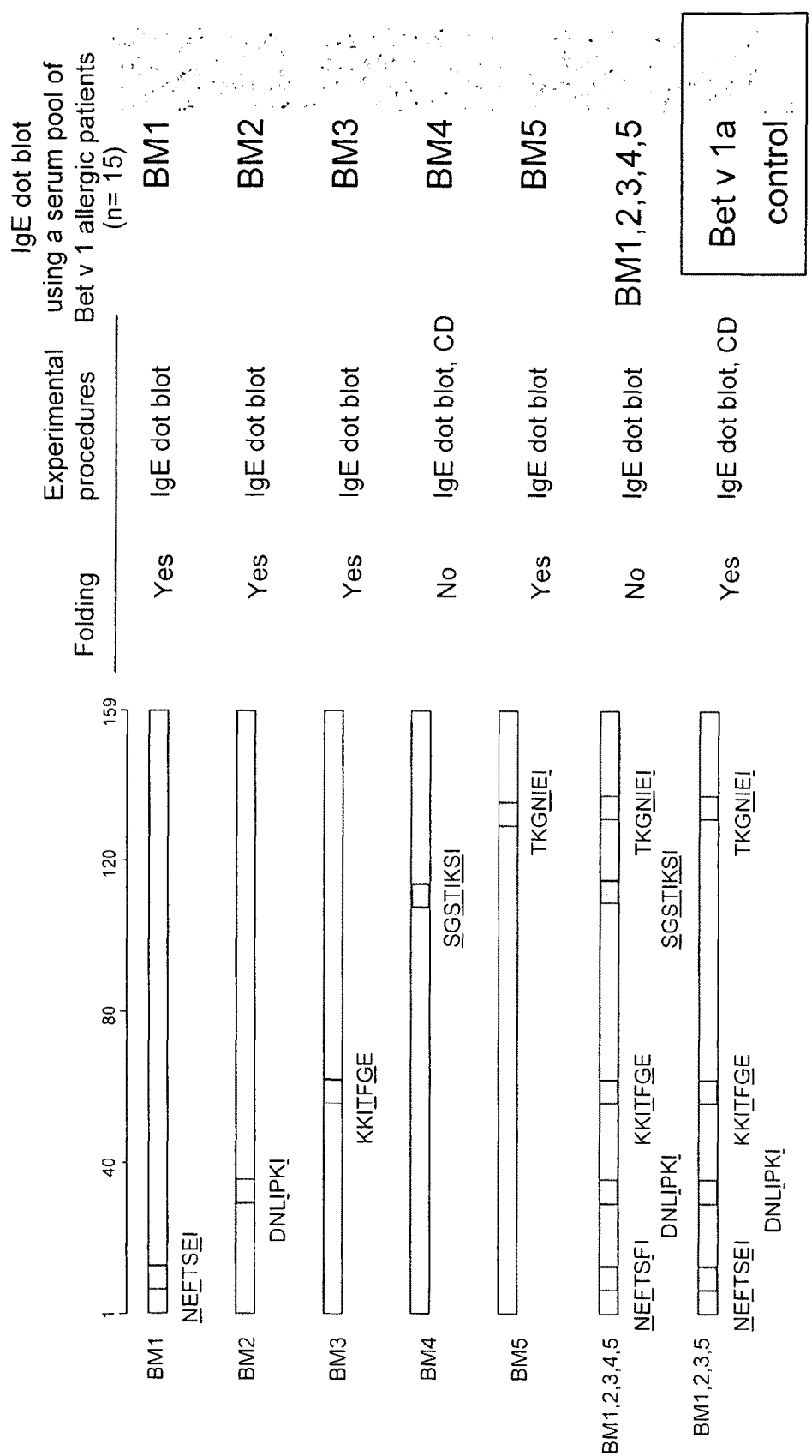

FIG. 15 shows a schematic representation of the mutant allergens BM1, BM2, BM3, BM4, BM5, BM1,2,3,4,5 and BM1,2,3,5. The allergens were produced by epitope grafting from Mal d 1.0108 to the scaffold of Bet v 1a. The grafted epitope sequences are indicated in the Figure, amino acids identical to Bet v 1a are shown in black, amino acids inserted from Mal d 1.0108 are underlined. The mutant allergens were expressed in $E.$ $coli$. Bet v 1-like folding of the different mutant allergens was either assessed by antibody binding in a dot blot or by circular dichroism spectroscopy of the purified allergens. Mutant allergens carrying the epitope 109-116 (SGSTIKSI; SEQ ID No. 7) of Mal d 1.0108 show no Bet v 1-like fold, however mutant allergen carrying other epitopes of Mal d 1.0108 were able to fold in a Bet v 1-like manner.

Figure 16:
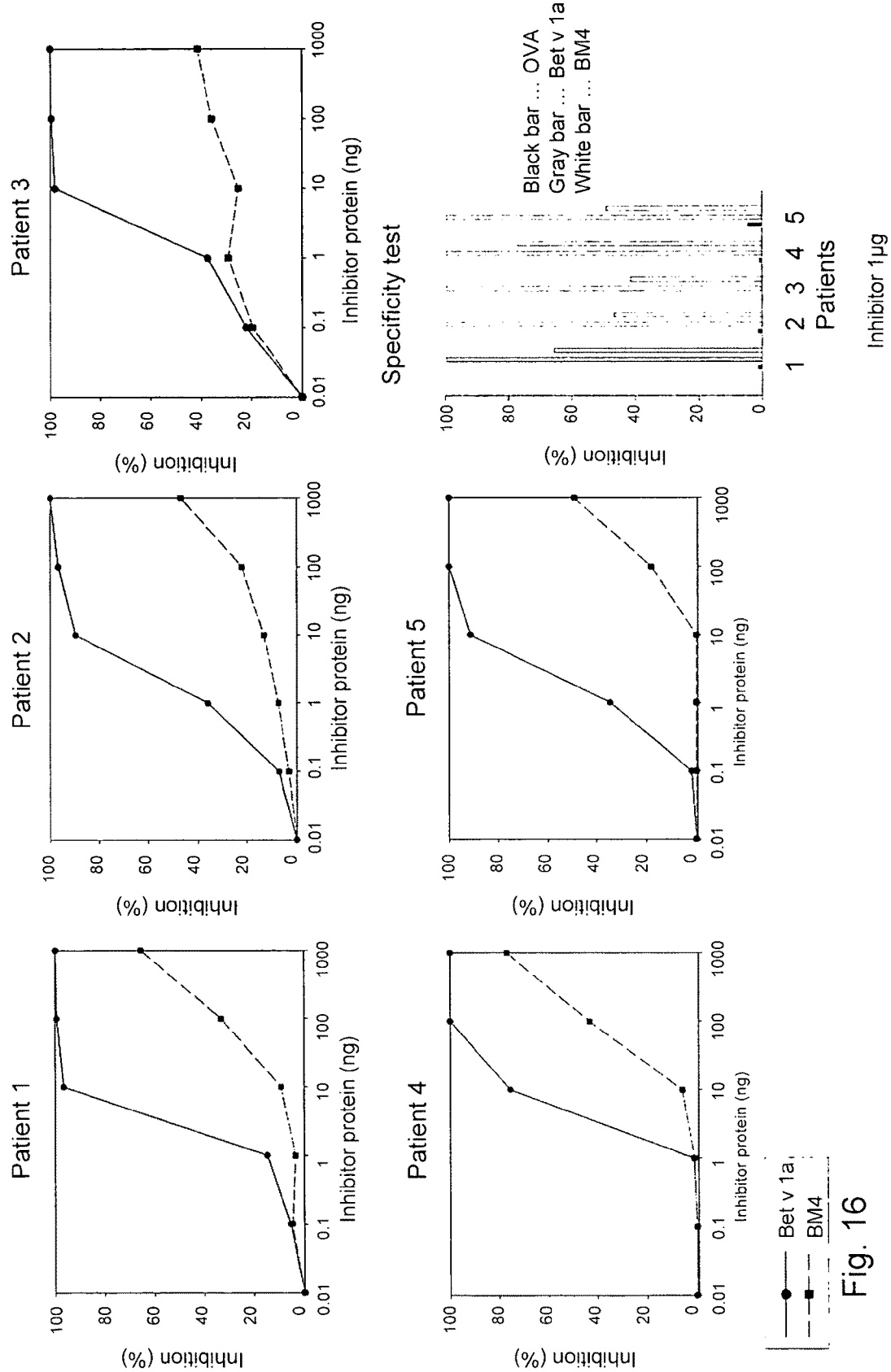

FIG. 16 demonstrates the reduced ability of BM4 to bind Bet v 1 specific patients' IgE, compared to wild-type Bet v 1a, as analyzed by ELISA inhibition. 200 ng/well of Bet v 1a were immobilized on an ELISA plate, patients' sera were incubated with serial dilutions of the respective inhibitor (e.g. Bet v 1a, BM4 or OVA as irrelevant control antigen). All measurements were performed as duplicates; results are presented as mean OD values after background subtraction. Sera of 5 birch pollen allergic individuals were tested. As control NHS was used which gave no signal to any of the proteins. Compared to Bet v 1a BM4 showed an approximately 100-1000 fold reduced patients' IgE binding capacity.

Figure 17:
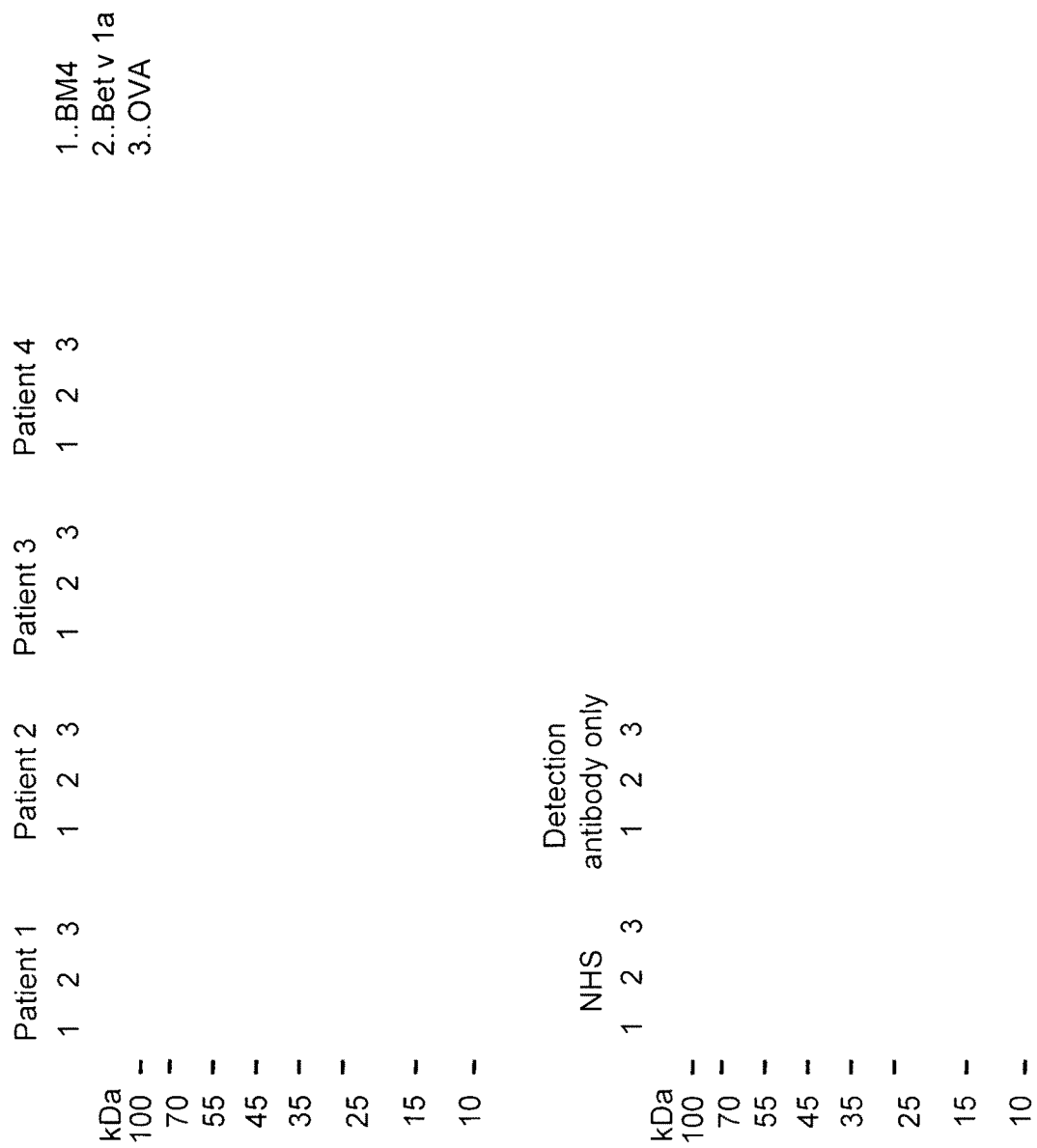

FIG. 17 shows an immunoblot of BM4, Bet v 1a and OVA used as irrelevant control antigen. Bound serum IgE was detected using $I^{125}$-labeled rabbit anti-human IgE (MedPro). BM4 shows virtually no IgE binding. As controls normal human serum or only the detection antibody were used.

FIG. 18 Homogeneity of BM4 was assessed by online-SEC light scattering using UV and triple detection array (SECTDA). BM4 appeared as single peak with a retention volume of 9.3 ml having an approximate MW of 20 kDa and a $R_H$ of >3.2 nm (a). Observed peak tailing might have been due to adsorptive effects and high $R_H$ due to extended conformation of unfolded protein. Detectors were calibrated with bovine serum albumin (BSA) having a MW of 66 kDa and a $R_H$ of 3.1 nm. System suitability was checked by rBet v 1a having a MW of 17 kDa and a $R_H$ of 1.9 nm. More than 99% homogeneity of non-aggregated BM4 was observed as no further peak was detected between void (5.7 ml) and total retention volume (12 ml) of SEC (b). HPSEC runs were performed using a 7.8×300 mm TSKgel G2000$_{SWXL}$ column (Tosoh Bioscience, Stuttgart, Germany) on a HP1100 analytical chromatography system (Hewlett-Packard, San Jose, Calif., USA) at 0.5 ml/min in PBS. Using a combination of the built-in UV detector measuring at 280 nm and a sequential refractive index (RI, short-dashed), intrinsic viscosity (IV, dash-dotted), and light scattering (RALS, long-dashed) detection system (TDA 302, Viscotek Corp., Houston, Tex., USA) the approximate molecular weight (MW, solid) and hydrodynamic radius ($R_H$, dash-double dotted) were determined.

FIG. 19 shows the aggregation behavior of BM4 in solution by dynamic light scattering (DLS). More than 97% of BM4 appeared as monomeric molecule with a hydrodynamic radius ($R_H$) of 3.5 nm and a polydispersity of 18.4% (a). As reference, rBet v 1a displayed an $R_H$ of 2.1 nm with a polydispersity of 16.7% (b). Thus, BM4 adopted a higher $R_H$, which was probably due to its unfolded state. Besides, <3% of BM4 appeared as multimer of molecular weight>1MDa. Dynamic light scattering was performed on DLS 802 (Viscotek Corp., Houston, Tex., USA) upon centrifugation for 10 min at 14,000×g in 10 mM sodium phosphate. The solvent settings for water were used. Data were accumulated for 10-20×10 sec and the correlation function was fitted into the combined data curve, from which the mass distribution was calculated by the OmniSize™ software package (Viscotek).

Figure 20:
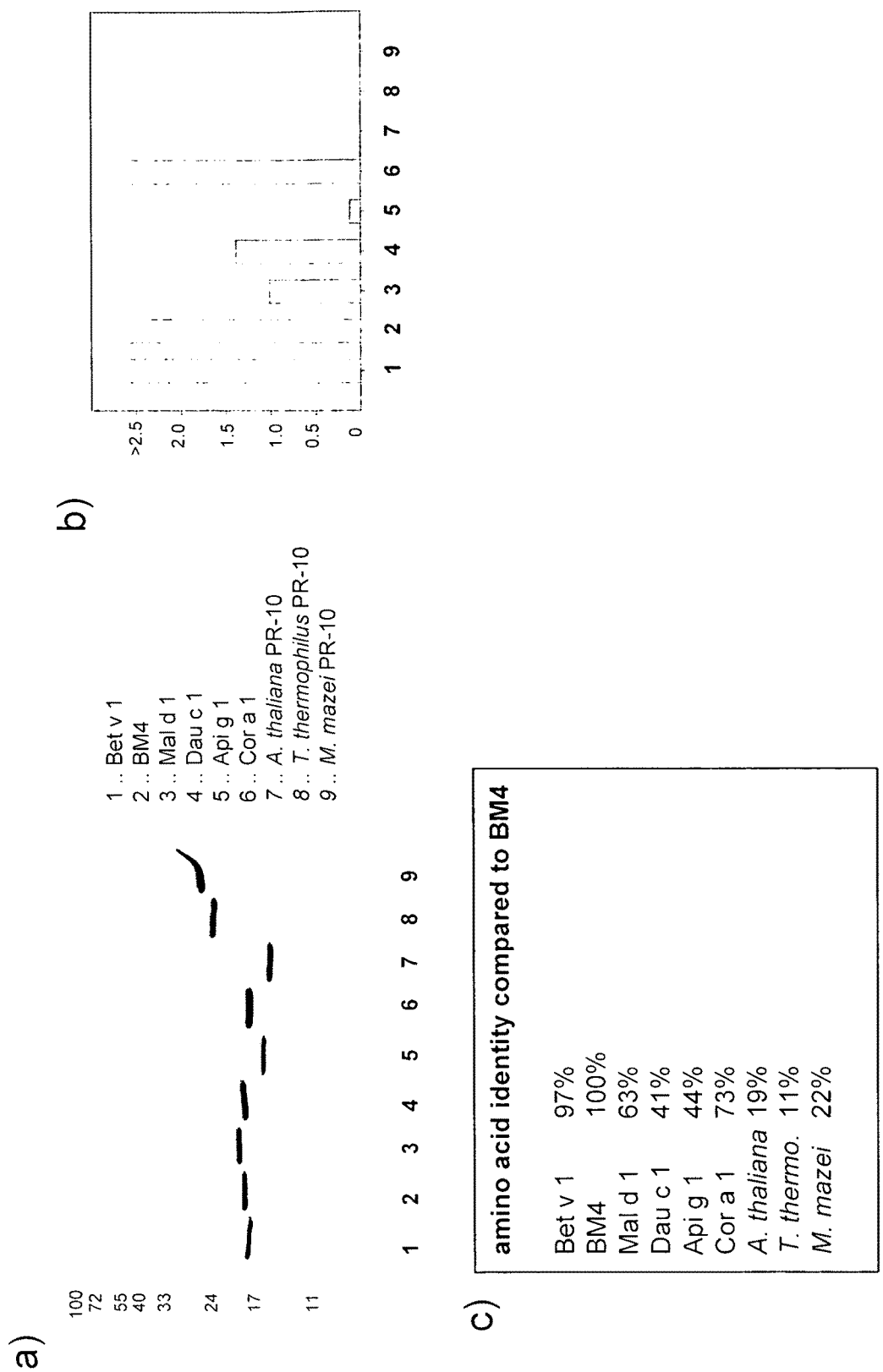

FIG. 20 Purified recombinant Bet v 1, BM4, Mal d 1, Dau c 1, Api g 1, Cor a 1, *Arabidopsis thaliana* PR-10 protein, *Thermus thermophilus* PR-10 protein, and *Methanosarcina mazei* PR-10 protein (3 μg per lane) were subjected to SDS-PAGE and stained with coomassie blue (a). ELISA using polyclonal rabbit anti Bet v 1 antibodies (1:5000) for demonstration of cross-reactivity of BM4 and homologous proteins (b). Recombinant Bet v 1, BM4 and Cor a 1 were extensively recognized by the rabbit antibody, and structural cross-reactivity could also be demonstrated for Dau c 1, Mal d 1, and Api g 1. No positive signals were obtained with purified PR-10 proteins from *Arabidopsis thaliana, Thermus thermophilus*, and *Methanosarcina mazei*. Sequence identity of abovementioned PR-10 proteins in comparison to BM4 (c). Amino acid alignment and identity plot was done with AlignX (Vector NTI, Invitrogen).

Figure 21:
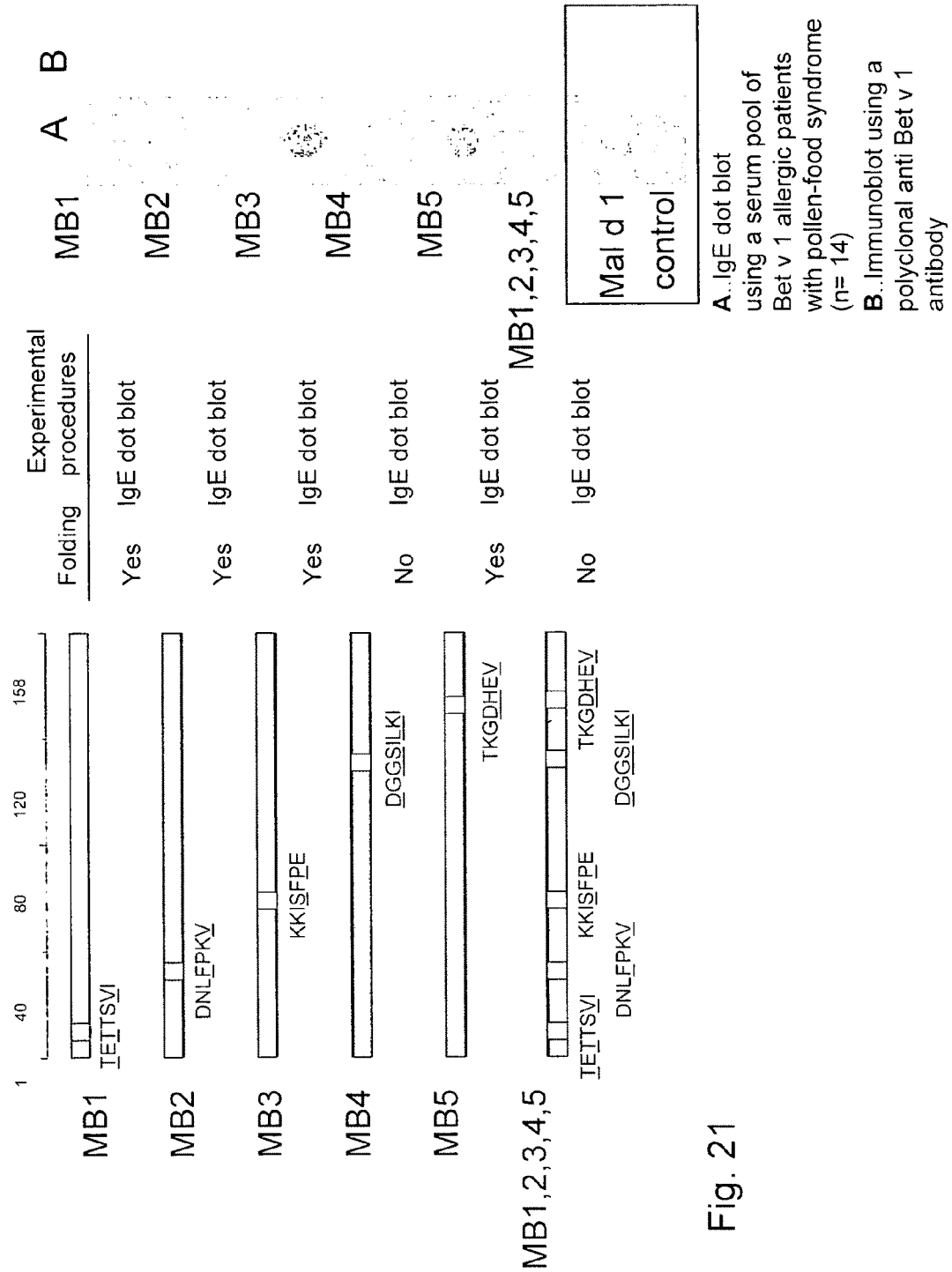

FIG. 21 shows a schematic representation of the mutant allergens MB1, MB2, MB3, MB4, MB5 and MB1,2,3,4,5. The allergens were produced by epitope grafting from Bet v 1a to the scaffold of Mal d 1.0108. The grafted epitope sequences are indicated in the Figure, amino acids identical to Mal d 1.0108 are shown in black, amino acids inserted from Bet v 1a in grey. The mutant allergens were expressed in *E. coli*. The folding of Bet v 1 and its homologues found in other pollen as well as food sources was found very similar as demonstrated by X-ray crystallographic analysis (Gajhede M, Nat Struct Biol. 1996 December; 3(12):1040-5; Neudecker P, J Biol Chem. 2001 Jun. 22; 276(25):22756-63. Epub 2001 Apr. 3; Schirmer T, J Mol Biol. 2005 Sep. 2; 351(5):1101-9).

This common fold results in good antibody cross-reactivity. Therefore the Bet v 1-like folding of the different Mal d 1.0108 mutant allergens was assessed by antibody binding in a dot blot using either serum from birch pollen allergic patients or affinity purified polyclonal rabbit anti Bet v 1 antibodies, which were shown to cross-react with Mal d 1. Based on these immunoblot results mutant allergens carrying the epitope 109-116 (DGGSILKI SEQ ID NO: 24) of Bet v 1a do not show a Bet v 1-like fold; however mutant allergens carrying other epitopes of Bet v 1a were able to fold in a Bet v 1-like manner.

EXAMPLES

Example 1

The pollen-food syndrome (PFS) is an association of food allergies to fruits, nuts, and vegetables in patients with pollen allergy. Mal d 1, the major apple allergen, is one of the most commonly associated food allergen for birch pollen-allergic patients suffering from PFS. Immunologically this is caused by cross-reactive IgE antibodies originally raised against the major birch pollen allergen, Bet v 1.

Although Bet v 1-specific IgE antibodies cross-react with Mal d 1, not every Bet v 1-allergic patient develops clinical reactions towards apple. This shows that distinct IgE epitopes present on both homologous allergens are responsible for the clinical manifestation of PFS. To test this four Mal d 1 stretches were grafted onto Bet v 1. The grafted regions were 7-amino acids long encompassing amino acids residues shown to be crucial for IgE recognition of Bet v 1.

The Bet v 1-Mal d 1 chimeric protein designated BM1,2,3,5 was expressed in *E. coli* and purified to homogeneity. BM1,2,3,5 was tested with patients' sera of i) Bet v 1-allergic patients displaying no clinical symptoms upon ingestion of apples and ii) Bet v 1-allergic patients displaying allergic symptoms upon ingestion of apples and other Bet v 1-related foods. Patients' IgE binding was assessed by ELISA.

Patients suffering from PFS reacted stronger with BM1,2,3,5 compared to solely birch allergic individuals. Thus B-cell epitopes of Bet v 1 implicated with apple allergy were successfully identified.

Methods

Patients' Sera:

Birch pollen allergic patients with and without PFS were selected based on typical case history, positive skin prick test and radioallergosorbent test (RAST) class 3. Correlation between clinical symptoms and relative IgE binding to Bet v 1 and Mal d 1 was confirmed for both groups of patients by ELISA using the respective antigens.

Cloning of BM1,2,3,5

BM1,2,3,5 was generated by PCR amplification of mutated fragments of Bet v 1a (X15877). Internal mismatch primers used for cloning were

```
Mut10F
                                          (SEQ ID No. 8)
5'CGCCATTGTTTTCAATTACGAAAaTGAGttCACCTCTGagATC3',

Mut30F
                                          (SEQ ID No. 9)
5'GATGGCGATAATCTCaTTCCAAAGaTTGCACCCCAA3',

Mut30R
                                         (SEQ ID No. 10)
5'ATGGCTTGGGGTGCAAtCTTTGGAAtGAGATTATCG3',

Mut57F
                                         (SEQ ID No. 11)
5'ATTAAGAAGATCAcCTTTggCGAAGGCTTC3',

Mut57R
                                         (SEQ ID No. 12)
5'GAAGCCTTCGccAAAGgTGATCTTCTTAAT3',

Mut125F
                                         (SEQ ID No. 13)
5'CACACCAAAGGTaACatTGAGaTcAAGGCAGAGCAG3',

Mut125R
                                         (SEQ ID No. 14)
5'CTGCTCTGCCTTgAtCTCAatGTtACCTTTGGTGTG3'.
```

Bases exchanged are indicated in lower case. Mutated fragments were gel-purified, pooled and assembled in a primerless PCR. Full length genes were amplified with the primers BetF 5'GGCCCATATGGGTGTTTTCAATTACGAA3' (SEQ ID No. 15) and BetR 5'TCGGCTCGAGGTTGTAGGCATCGGAGTG3' (SEQ ID No. 16). Restriction sites are underlined. BM1,2,3,5 was cloned into a pHis-Parallel2 vector using Nde I and Xho I restriction sites (Wallner M et al., Methods 2004, 32(3):219-26).

Expression and Purification of BM4

Expression plasmids were transformed in *E. coli* BL21 (DE3) pLysS cells (Stratagene) and grown at 37° C. to and OD600 of 0.8 in LB medium supplemented with 100 mg/L ampicillin. Cultures were cooled to 16° C. and protein expression was induced by addition of 0.3 mM isopropyl-β-D-thiogalactopyranoside (IPTG). After incubation for 18 h, cells were harvested by low speed centrifugation and resuspended in appropriate lysis buffer. BM1,2,3,5 was expressed 6×His tagged fusion protein and purified from soluble bacterial lysates by immobilized metal affinity chromatography (Wallner M et al., Methods 2004, 32(3):219-26). Recombinant proteins were dialyzed against 10 mM sodium phosphate buffer, pH 7.4 and stored at −20° C.

SDS-PAGE and Immunoblots

E. coli lysates and purified proteins were analyzed by denaturing sodium dodecyl sulfate polyacrylamide gel electrophoresis (SDS-PAGE) using 15% gels. Proteins were visualized by staining with Coomassie Brilliant Blue R-250 (Biorad).

For immunoblot analysis proteins separated by SDS-PAGE were electroblotted on nitrocellulose membrane (Schleicher & Schuell). Proteins were detected using the monoclonal anti Bet v 1 antibody BIP-1 (1:10.000) (Ferreira F et al., FASEB 1998, 12:231-242). Bound BIP-1 was detected with an AP-conjugated rabbit anti mouse IgG+IgM (Immunoresearch Laboratories Inc.).

Circular Dichroism

Circular dichroism (CD) spectra of proteins were recorded in 5 mM sodium phosphate pH 7.4 with a JASCO J-810 spectropolarimeter (Jasco) fitted with a Neslab RTE-111M temperature control system (Thermo Neslab Inc.). Obtained curves were baseline-corrected; results are presented as mean residue molar ellipticity [θ]MRW at a given wavelength. Protein concentrations for normalizing CD signals were determined at OD280.

Molecular Modelling

Modelling was performed using the comparative modelling tool MODELLER and evaluated by ProSa2003. All models are based on the PDB structure file 1bv1 (Bet v 1) and presented using PyMOL 0.98.

ELISA Experiments

For IgE ELISA experiments, Maxisorp plates (NUNC) were coated with allergen titrations in 50 µl PBS/well overnight at 4° C. Plates were blocked with TBS, pH 7.4, 0.05% (v/v) Tween, 1% (w/v) BSA and incubated with patients' sera diluted 1:5 overnight at 4° C. Bound IgE was detected with alkaline phosphatase-conjugated monoclonal anti-human IgE antibodies (BD Biosciences Pharmingen), after incubation for 1 h at 37° C. and 1 h at 4° C. Alternatively, Bet v 1 and homologous proteins were coated at 4 µg/ml in 50 µl PBS/well overnight at 4° C. Blocking was done as described above and incubated with polyclonal rabbit anti rBet v 1 antibody using different dilutions (1:5.000-1:20.000). Detection was performed with an alkaline phosphatase-conjugated goat anti rabbit antibody. 10 mM 4-Nitrophenyl phosphate (Sigma-Aldrich) was used as substrate and OD was measured at 405/492 nm. Measurements were performed as triplicates (IgE ELISA) or duplicates (rabbit anti Bet v 1 antibody); results are presented as mean OD values.

Results

The aim of the present example was the identification of cross-reactive B cell epitopes responsible for the clinical manifestation of Bet v 1-related PFS towards apple. Therefore the mutant allergen BM1,2,3,5 was designed by implanting distinct epitopes of Mal d 1.0108 at corresponding positions of the Bet v 1a sequence (FIG. 1A). The grafted regions were defined as stretches of 7 consecutive amino acids encompassing residues already described to be crucial for IgE recognition of Bet v 1 and homologues. These particular residues (Thr10, Phe30, Ser57 and Asp125 in Bet v 1a) could not only alter IgE binding to Bet v 1, also IgE recognition of Mal d 1 is highly dependent of amino acids at the corresponding positions. The introduction of distinct mutations at the described sites does not change the overall structure of the allergens as demonstrated by circular dichroismus (CD), though this can drastically influence allergenicity of the molecules. By investigating patients IgE binding towards BM1, 2,3,5 the grafted epitopes serve as indicator for cross-reactivity of Bet v 1 and Mal d 1. Since IgE epitopes of Bet v 1 are conformational an intact structure of the hybrid was essential. The 3-dimensional fold of BM1,2,3,5 was first evaluated by calculating a molecular model which was then compared to the 3-D structure of Bet v 1. The model showed the same conserved shape as the template allergen. All 4 mutated epitopes were exposed on the protein surface and therefore could influence antibody binding to BM1,2,3,5 (FIG. 1B). The calculated mutant allergen was cloned, expressed in E. coli as 6×His tagged fusion protein and purified to homogeneity. To verify in silico data on protein structure far UV CD spectra of BM1,2,3,5 and Bet v 1a were recorded and compared after normalizing the signals to [θ]MRW units. The overlay of both spectra indicated almost identical secondary structures (FIG. 1C). Further evidence of similar folding was provided by antibody binding of a monoclonal anti Bet v 1 antibody which was equivalent for both proteins a further indication of a Bet v 1-like fold of BM1,2,3,5 (FIG. 2A). To investigate IgE antibody binding of BM1,2,3,5, ELISA experiments were done with 2 groups of patients: i) Bet v 1 allergic patients without PFS and ii) Bet v 1 allergic patients showing PFS symptoms following apple ingestion. As reference the allergens Bet v 1a and Mal d 1.0108 were used. No significant difference of patients' IgE binding towards Bet v 1 ($P>0.99$) was observed in any of the two groups. IgE binding to Mal d 1.0108 was stronger for the PFS group compared to the non-PFS patients, though the latter also recognized the major apple allergen in ELISA. However IgE binding to BM1,2,3,5 was significantly reduced in the non-PFS group compared to patients with PFS ($P<0.01$) (FIG. 2B). The ELISA data demonstrate that the grafted epitopes are implicated in birch pollen PFS. IgE antibodies of Bet v 1 allergic individuals without PFS could not efficiently bind to BM1,2, 3,5 however cross-reactive antibodies of individuals with PFS could still recognize the mutated allergen.

Example 2

The mutant allergen BM4 is based on the protein backbone of Bet v 1a where an epitope of 8 amino acids has been replaced by an epitope of Mal d 1.0108. The incorporation of the Mal d 1 epitope results in a protein which cannot fold in a Bet v 1-like manner and remains unfolded; however the unfolded protein stays in solution and is stable.

BM4 was cloned with 5' Nco I, 3' Eco R I in the vector pHis Parallel 2 and produced as 6×his tagged fusion protein with an N-terminal his tag in E. coli BL21 (DE3). The protein was purified from the insoluble fraction of E. coli using a 6M Urea containing $Ni^{2+}$ buffer, loaded on a $Ni^{2+}$ column, refolded on column and eluted with imidazole. The purified his tagged protein was subsequently cleaved with rTEV protease, non-tagged BM4 was purified again by IMAC and dialyzed against 10 mM sodium phosphate buffer pH 8. The yield of a 1 L LB Amp culture was approximately 200 mg of BM4 after purification.

Protein purity was monitored by SDS-PAGE indicating a purity of over 99%, the correct mass of the intact protein was verified by ESI-Q TOF mass spectrometry (measured mass 17690; calculated average protein mass 17689 Da). Aggregation status of BM4 was determined by size exclusion chromatography. The content of higher molecular weight aggregates was below 0.5%, 99.5% of the protein was found to be monomeric. Protein secondary structure was determined by circular dichroism spectroscopy. The protein was found to be unfolded.

No IgE binding to BM4 was detected in immunoblots using a serum pool from Bet v 1 allergic patients and $I^{125}$-labeled rabbit anti-human IgE (MedPro) as detection antibody. In mediator release assays using rat basophilic leukaemia cells transfected with a human FcεRI receptor and sera of Bet v 1 allergic patients, a 100-1000 fold reduction of anaphylactic potential was observed for BM4 as compared to Bet v 1a.

T cell proliferation of BM4 was determined. Proliferative responses of human peripheral blood mononuclear cells (PBMCs) established from birch pollen-allergic patients were found to be higher for BM4 than for Bet v 1a or Mal d 1.0108.

Pre-clinical models are required to further characterize BM4. Mice were immunized with BM4 and immunologic parameters have been assessed: IgG as well as IgE titers towards Bet v 1a and BM4 were determined by ELISA. Further IgE binding was assessed by mediator release assays using rat basophilic leukaemia cells. The induction of blocking antibodies (IgG) against Bet v 1a was determined by indirect ELISA with end-point titrations of sera from immunized mice. T cell responses of mice were analyzed by ELISpot assays, T helper cells induced by immunization of BM4 were compared to those induced by immunization of mice with Bet v 1a.

An untagged BM4 construct was cloned as follows:

BM4 was inserted with 5' Nco I and 3' Eco R I in a pET 28b vector (Kan R) and transformed into E. coli BL21 Star™ (DE3) (Invitrogen) cells. The construct was sequenced and protein expression and purification tests were performed.

The products were produced as follows. Transformed cells were grown in a shaker flask in 1 L LB amp medium, protein expression was induced with 0.5 mM IPTG at OD600 of 0.8. The cells were harvested by low speed centrifugation, broken and the BM4 was recovered from the insoluble inclusion bodies with 6M UREA, 20 mM imidazole pH 7.4. The protein was refolded by dialysis against 20 mM sodium phosphate buffer. Secondary structure elements of BM4 were analysed by circular dichroism spectroscopy. BM4 produced as untagged recombinant protein in E. coli was found to be unfolded.

Example 3

In order to show that the mutation of amino acid residues 102, 114 and 120 of Bet v 1a results in a hypoallergenic molecule several Bet v 1a variants have been constructed. All of these molecules exhibit a reduced IgE reactivity compared to wild-type Bet v 1a.

TABLE 1

Z-Score of Bet v 1a and variants therof. The Z-score can be used to determine the 3D structure of the protein

|  | Description of mutant protein | Number of residues | Z-combined | Z-pair wise | Z-surface |
|---|---|---|---|---|---|
| wild type Bet v 1a | 1bv1_I102I_L114L_Y120Y | 159 | −9.18 | −6.45 | −7.01 |
|  | 1bv1_I102K_L114D_Y120Q | 159 | −7.60 | −5.74 | −5.79 |
|  | 1bv1_I102K_L114K_Y120R | 159 | −7.60 | −5.77 | −5.76 |
|  | 1bv1_I102D_L114K_Y120K | 159 | −7.59 | −5.87 | −5.72 |
|  | 1bv1_I102E_L114D_Y120K | 159 | −7.59 | −5.74 | −5.80 |
|  | 1bv1_I102E_L114K_Y120D | 159 | −7.59 | −5.92 | −5.68 |
|  | 1bv1_I102K_L114E_Y120Q | 159 | −7.59 | −5.81 | −5.76 |
|  | 1bv1_I102K_L114N_Y120E | 159 | −7.59 | −5.76 | −5.77 |
|  | 1bv1_I102D_L114D_Y120E | 159 | −7.58 | −5.66 | −5.83 |
|  | 1bv1_I102E_L114E_Y120K | 159 | −7.58 | −5.81 | −5.77 |
|  | 1bv1_I102K_L114D_Y120D | 159 | −7.58 | −5.82 | −5.72 |
|  | 1bv1_I102D_L114E_Y120E | 159 | −7.57 | −5.73 | −5.79 |
|  | 1bv1_I102K_L114E_Y120D | 159 | −7.57 | −5.90 | −5.68 |
|  | 1bv1_I102K_L114K_Y120S | 159 | −7.57 | −5.90 | −5.65 |
|  | 1bv1_I102K_L114Q_Y120E | 159 | −7.57 | −5.73 | −5.78 |
|  | 1bv1_I102Q_L114K_Y120E | 159 | −7.57 | −5.71 | −5.78 |
|  | 1bv1_I102K_L114K_Y120N | 159 | −7.56 | −5.87 | −5.66 |
|  | 1bv1_I102K_I114K_Y120P | 159 | −7.55 | −5.82 | −5.64 |
|  | 1bv1_I102D_L114K_Y120E | 159 | −7.54 | −5.79 | −5.70 |
|  | 1bv1_I102E_L114D_Y120E | 159 | −7.54 | −5.65 | −5.79 |
|  | 1bv1_I102E_L114K_Y120K | 159 | −7.54 | −5.86 | −5.68 |
|  | 1bv1_I102K_L114K_Y120G | 159 | −7.54 | −5.86 | −5.65 |
|  | 1bv1_I102E_L114E_Y120E | 159 | −7.53 | −5.72 | −5.75 |
|  | 1bv1_I102K_L114D_Y120K | 159 | −7.53 | −5.76 | −5.72 |
|  | 1bv1_I102K_L114E_Y120K | 159 | −7.52 | −5.83 | −5.68 |
|  | 1bv1_I102K_L114K_Y120Q | 159 | −7.51 | −5.77 | −5.67 |
|  | 1bv1_I102E_L114K_Y120E | 159 | −7.49 | −5.77 | −5.67 |
|  | 1bv1_I102K_L114D_Y120E | 159 | −7.48 | −5.67 | −5.70 |
|  | 1bv1_I102K_L114K_Y120D | 159 | −7.48 | −5.85 | −5.60 |
|  | 1bv1_I102K_L114E_Y120E | 159 | −7.47 | −5.74 | −5.66 |
|  | 1bv1_I102K_L114K_Y120K | 159 | −7.44 | −5.79 | −5.59 |
|  | 1bv1_I102K_L114K_Y120E | 159 | −7.38 | −5.70 | −5.58 |

Sippl, M. J. et al. Stat.mechanics, protein struct & protein-.substrate interactions; 0, pp. 297-315, (1994)

The description of mutant proteins indicates the pbd file of the template protein, which has been used to as scaffold for the mutations, in this context Bet v 1 (pdb entry 1bv1). Further the positions which have been mutated are listed (e.g I120K meaning I at position 102 has been replaced by K).

The invention claimed is:

1. A mutant polypeptide, comprising SEQ ID NO:3.
2. A composition, comprising the mutant polypeptide of claim 1 and at least one pharmaceutically acceptable excipient, diluent, adjuvant and/or carrier.

* * * * *

SEQUENCE LISTING

<160> NUMBER OF SEQ ID NOS: 204

<210> SEQ ID NO 1
<211> LENGTH: 159
<212> TYPE: PRT
<213> ORGANISM: Betula pendula

<400> SEQUENCE: 1

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Ile Gly Asp Thr Leu Glu
                85                  90                  95

Lys Ile Ser Asn Glu Ile Lys Ile Val Ala Thr Pro Asp Gly Gly Ser
            100                 105                 110

Ile Leu Lys Ile Ser Asn Lys Tyr His Thr Lys Gly Asp His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155

<210> SEQ ID NO 2
<211> LENGTH: 158
<212> TYPE: PRT
<213> ORGANISM: Malus domestica

<400> SEQUENCE: 2

Gly Val Tyr Thr Phe Glu Asn Glu Phe Thr Ser Glu Ile Pro Pro Ser
1               5                   10                  15

Arg Leu Phe Lys Ala Phe Val Leu Asp Ala Asp Asn Leu Ile Pro Lys
            20                  25                  30

Ile Ala Pro Gln Ala Ile Lys Gln Ala Glu Ile Leu Glu Gly Asn Gly
        35                  40                  45

Gly Pro Gly Thr Ile Lys Lys Ile Thr Phe Gly Glu Gly Ser Gln Tyr
    50                  55                  60

Gly Tyr Val Lys His Arg Ile Asp Ser Ile Asp Glu Ala Ser Tyr Ser
65                  70                  75                  80

Tyr Ser Tyr Thr Leu Ile Glu Gly Asp Ala Leu Thr Asp Thr Ile Glu
                85                  90                  95

Lys Ile Ser Tyr Glu Thr Lys Leu Val Ala Cys Gly Ser Gly Ser Thr
            100                 105                 110

Ile Lys Ser Ile Ser His Tyr His Thr Lys Gly Asn Ile Glu Ile Lys
        115                 120                 125

Glu Glu His Val Lys Ala Gly Lys Glu Lys Ala His Gly Leu Phe Lys
    130                 135                 140

Leu Ile Glu Ser Tyr Leu Lys Asp His Pro Asp Ala Tyr Asn
145                 150                 155

```
<210> SEQ ID NO 3
<211> LENGTH: 159
<212> TYPE: PRT
<213> ORGANISM: Artificial
<220> FEATURE:
<223> OTHER INFORMATION: Bet v 1 - Mal d 1 hybrid

<400> SEQUENCE: 3

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Ile Gly Asp Thr Leu Glu
                85                  90                  95

Lys Ile Ser Asn Glu Ile Lys Ile Val Ala Thr Pro Ser Gly Ser Thr
            100                 105                 110

Ile Lys Ser Ile Ser Asn Lys Tyr His Thr Lys Gly Asp His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155

<210> SEQ ID NO 4
<211> LENGTH: 12
<212> TYPE: PRT
<213> ORGANISM: Artificial
<220> FEATURE:
<223> OTHER INFORMATION: Bet v 1 fragment

<400> SEQUENCE: 4

Ser Ile Leu L

```
<210> SEQ ID NO 7
<211> LENGTH: 8
<212> TYPE: PRT
<213> ORGANISM: Artificial
<220> FEATURE:
<223> OTHER INFORMATION: Mal d 1 fragment

<400> SEQUENCE: 7

Ser Gly Ser Thr Ile Lys Ser Ile
1               5

<210> SEQ ID NO 8
<211> LENGTH: 43
<212> TYPE: DNA
<213> ORGANISM: Artificial
<220> FEATURE:
<223> OTHER INFORMATION: Primer

<400> SEQUENCE: 8
cgccattgtt ttcaattacg aaaatgagtt cacctctgag atc                    43

<210> SEQ ID NO 9
<211> LENGTH: 36
<212> TYPE: DNA
<213> ORGANISM: Artificial
<220> FEATURE:
<223> OTHER INFORMATION: Primer

<400> SEQUENCE: 9
gatggcgata atctcattcc aaagattgca ccccaa                            36

<210> SEQ ID NO 10
<211> LENGTH: 36
<212> TYPE: DNA
<213> ORGANISM: Artificial
<220> FEATURE:
<223> OTHER INFORMATION: Primer

<400> SEQUENCE: 10
atggcttggg gtgcaatctt tggaatgaga ttatcg                            36

<210> SEQ ID NO 11
<211> LENGTH: 30
<212> TYPE: DNA
<213> ORGANISM: Artificial
<220> FEATURE:
<223> OTHER INFORMATION: Primer

<400> SEQUENCE: 11
attaagaaga tcacctttgg cgaaggcttc                                   30

<210> SEQ ID NO 12
<211> LENGTH: 30
<212> TYPE: DNA
<213> ORGANISM: Artificial
<220> FEATURE:
<223> OTHER INFORMATION: Primer

<400> SEQUENCE: 12
gaagccttcg ccaaaggtga tcttcttaat                                   30

<210> SEQ ID NO 13
<211> LENGTH: 36
<212> TYPE: DNA
<213> ORGANISM: Artificial
<220> FEATURE:
<223> OTHER INFORMATION: Primer
```

```
<400> SEQUENCE: 13
cacaccaaag gtaacattga gatcaaggca gagcag                                36

<210> SEQ ID NO 14
<211> LENGTH: 36
<212> TYPE: DNA
<213> ORGANISM: Artificial
<220> FEATURE:
<223> OTHER INFORMATION: Primer

<400> SEQUENCE: 14
ctgctctgcc ttgatctcaa tgttaccttt ggtgtg                                36

<210> SEQ ID NO 15
<211> LENGTH: 28
<212> TYPE: DNA
<213> ORGANISM: Artificial
<220> FEATURE:
<223> OTHER INFORMATION: Primer

<400> SEQUENCE: 15
ggcccatatg ggtgttttca attacgaa                                        28

<210> SEQ ID NO 16
<211> LENGTH: 28
<212> TYPE: DNA
<213> ORGANISM: Artificial
<220> FEATURE:
<223> OTHER INFORMATION: Primer

<400> SEQUENCE: 16
tcggctcgag gttgtaggca tcggagtg                                        28

<210> SEQ ID NO 17
<211> LENGTH: 7
<212> TYPE: PRT
<213> ORGANISM: Artificial
<220> FEATURE:
<223> OTHER INFORMATION: Mal d 1 fragment

<400> SEQUENCE: 17

Asn Glu Phe Thr Ser Glu Ile
1               5

<210> SEQ ID NO 18
<211> LENGTH: 7
<212> TYPE: PRT
<213> ORGANISM: Artificial
<220> FEATURE:
<223> OTHER INFORMATION: Mal d 1 fragment

<400> SEQUENCE: 18

Asp Asn Leu Ile Pro Lys Ile
1               5

<210> SEQ ID NO 19
<211> LENGTH: 7
<212> TYPE: PRT
<213> ORGANISM: Artificial
<220> FEATURE:
<223> OTHER INFORMATION: Mal d 1 fragment

<400> SEQUENCE: 19

Lys Lys Ile Thr Phe Gly Glu
1               5
```

```
<210> SEQ ID NO 20
<211> LENGTH: 7
<212> TYPE: PRT
<213> ORGANISM: Artificial
<220> FEATURE:
<223> OTHER INFORMATION: Mal d 1 fragment

<400> SEQUENCE: 20

Thr Lys Gly Asn Ile Glu Ile
1               5

<210> SEQ ID NO 21
<211> LENGTH: 7
<212> TYPE: PRT
<213> ORGANISM: Artificial
<220> FEATURE:
<223> OTHER INFORMATION: Bet v 1a fragment

<400> SEQUENCE: 21

Thr Glu Thr Thr Ser Val Ile
1               5

<210> SEQ ID NO 22
<211> LENGTH: 7
<212> TYPE: PRT
<213> ORGANISM: Artificial
<220> FEATURE:
<223> OTHER INFORMATION: Bet v 1a fragment

<400> SEQUENCE: 22

Asp Asn Leu Phe Pro Lys Val
1               5

<210> SEQ ID NO 23
<211> LENGTH: 7
<212> TYPE: PRT
<213> ORGANISM: Artificial
<220> FEATURE:
<223> OTHER INFORMATION: Bet v 1a fragment

<400> SEQUENCE: 23

Lys Lys Ile Ser Phe Pro Glu
1               5

<210> SEQ ID NO 24
<211> LENGTH: 8
<212> TYPE: PRT
<213> ORGANISM: Artificial
<220> FEATURE:
<223> OTHER INFORMATION: Bet v 1a fragment

<400> SEQUENCE: 24

Asp Gly Gly Ser Ile Leu Lys Ile
1               5

<210> SEQ ID NO 25
<211> LENGTH: 7
<212> TYPE: PRT
<213> ORGANISM: Artificial
<220> FEATURE:
<223> OTHER INFORMATION: Bet v 1a fragment

<400> SEQUENCE: 25

Thr Lys Gly Asp His Glu Val
1               5
```

<210> SEQ ID NO 26
<211> LENGTH: 58
<212> TYPE: PRT
<213> ORGANISM: Artificial
<220> FEATURE:
<223> OTHER INFORMATION: Dauc1.0101 fragment

<400> SEQUENCE: 26

Glu Gly Ser Pro Ile Thr Ser Met Thr Val Arg Thr Asp Ala Val Asn
1               5                   10                  15

Lys Glu Ala Leu Thr Tyr Asp Ser Thr Val Ile Asp Gly Asp Ile Leu
            20                  25                  30

Leu Gly Phe Ile Glu Ser Ile Glu Thr His Leu Val Val Val Pro Thr
        35                  40                  45

Ala Asp Gly Gly Ser Ile Thr Lys Thr Thr
    50                  55

<210> SEQ ID NO 27
<211> LENGTH: 58
<212> TYPE: PRT
<213> ORGANISM: Artificial
<220> FEATURE:
<223> OTHER INFORMATION: Dauc1.0102 fragment

<400> SEQUENCE: 27

Glu Gly Ser Pro Ile Thr Ser Met Thr Val Arg Thr Asp Ala Val Asn
1               5                   10                  15

Lys Glu Ala Leu Thr Tyr Asp Ser Thr Val Ile Asp Gly Asp Ile Leu
            20                  25                  30

Leu Gly Phe Ile Glu Ser Ile Glu Thr His Leu Val Val Val Pro Thr
        35                  40                  45

Ala Asp Gly Gly Ser Ile Thr Lys Thr Thr
    50                  55

<210> SEQ ID NO 28
<211> LENGTH: 58
<212> TYPE: PRT
<213> ORGANISM: Artificial
<220> FEATURE:
<223> OTHER INFORMATION: Dauc1.0104 fragment

<400> SEQUENCE: 28

Glu Gly Ser Pro Ile Thr Ser Met Thr Val Arg Thr Asp Ala Val Asn
1               5                   10                  15

Lys Glu Ala Leu Thr Tyr Asp Ser Thr Val Ile Asp Gly Asp Ile Leu
            20                  25                  30

Leu Gly Phe Ile Glu Ser Ile Glu Thr His Leu Val Val Val Pro Thr
        35                  40                  45

Ala Asp Gly Gly Ser Ile Thr Lys Thr Thr
    50                  55

<210> SEQ ID NO 29
<211> LENGTH: 58
<212> TYPE: PRT
<213> ORGANISM: Artificial
<220> FEATURE:
<223> OTHER INFORMATION: Dauc1.0105 fragment

<400> SEQUENCE: 29

Glu Gly Ser Pro Ile Thr Ser Met Thr Val Arg Thr Asp Ala Val Asn
1               5                   10                  15

```
Lys Glu Ala Leu Thr Tyr Asp Ser Thr Val Ile Asp Gly Asp Ile Leu
            20                  25                  30

Leu Gly Phe Ile Glu Ser Ile Glu Thr His Leu Val Val Val Pro Thr
        35                  40                  45

Ala Asp Gly Gly Ser Ile Thr Lys Thr Thr
    50                  55

<210> SEQ ID NO 30
<211> LENGTH: 58
<212> TYPE: PRT
<213> ORGANISM: Artificial
<220> FEATURE:
<223> OTHER INFORMATION: Dauc1.0103 fragment

<400> SEQUENCE: 30

Glu Gly Ser Pro Ile Thr Ser Met Thr Val Arg Thr Asp Ala Val Asn
1               5                   10                  15

Lys Glu Ala Leu Thr Tyr Asp Ser Thr Val Ile Asp Gly Asp Ile Leu
            20                  25                  30

Leu Glu Phe Ile Glu Ser Ile Glu Thr His Met Val Val Val Pro Thr
        35                  40                  45

Ala Asp Gly Gly Ser Ile Thr Lys Thr Thr
    50                  55

<210> SEQ ID NO 31
<211> LENGTH: 58
<212> TYPE: PRT
<213> ORGANISM: Artificial
<220> FEATURE:
<223> OTHER INFORMATION: Apig1.0101 fragment

<400> SEQUENCE: 31

Asp Gly Gly Pro Ile Thr Thr Met Thr Leu Arg Ile Asp Gly Val Asn
1               5                   10                  15

Lys Glu Ala Leu Thr Phe Asp Tyr Ser Val Ile Asp Gly Asp Ile Leu
            20                  25                  30

Leu Gly Phe Ile Glu Ser Ile Glu Asn His Val Val Leu Val Pro Thr
        35                  40                  45

Ala Asp Gly Gly Ser Ile Cys Lys Thr Thr
    50                  55

<210> SEQ ID NO 32
<211> LENGTH: 57
<212> TYPE: PRT
<213> ORGANISM: Artificial
<220> FEATURE:
<223> OTHER INFORMATION: Apig1.0201 fragment

<400> SEQUENCE: 32

Glu Ala Thr Glu Tyr Thr Thr Met Lys Gln Lys Val Asp Val Ile Asp
1               5                   10                  15

Lys Ala Gly Leu Ala Tyr Thr Tyr Thr Ile Gly Gly Asp Ile Leu
            20                  25                  30

Val Asp Val Leu Glu Ser Val Val Asn Glu Phe Val Val Pro Thr
        35                  40                  45

Asp Gly Gly Cys Ile Val Lys Asn Thr
    50                  55

<210> SEQ ID NO 33
<211> LENGTH: 57
<212> TYPE: PRT
```

```
<213> ORGANISM: Artificial
<220> FEATURE:
<223> OTHER INFORMATION: Dauc1.02.01 fragment

<400> SEQUENCE: 33

Glu Ala Thr Glu Tyr Thr Thr Met Lys Gln Lys Val Asp Val Ile Asp
1               5                   10                  15

Lys Ala Gly Leu Gly Tyr Thr Tyr Thr Ile Gly Gly Asp Ile Leu
            20                  25                  30

Val Glu Gly Leu Glu Ser Val Val Asn Gln Phe Val Val Pro Thr
        35                  40                  45

Asp Gly Gly Cys Ile Val Lys Asn Thr
    50                  55

<210> SEQ ID NO 34
<211> LENGTH: 58
<212> TYPE: PRT
<213> ORGANISM: Artificial
<220> FEATURE:
<223> OTHER INFORMATION: Petc1 fragment

<400> SEQUENCE: 34

Asp Ala Ser Pro Phe Lys Thr Met Lys Gln Lys Val Asp Ala Ile Asp
1               5                   10                  15

Lys Ala Thr Phe Thr Tyr Ser Tyr Ser Ile Ile Asp Gly Asp Ile Leu
            20                  25                  30

Leu Gly Phe Ile Glu Ser Ile Asn Asn His Phe Thr Ala Val Pro Asn
        35                  40                  45

Ala Asp Gly Gly Cys Thr Val Lys Ser Thr
    50                  55

<210> SEQ ID NO 35
<211> LENGTH: 57
<212> TYPE: PRT
<213> ORGANISM: Artificial
<220> FEATURE:
<223> OTHER INFORMATION: Cass1/1 fragment

<400> SEQUENCE: 35

Glu Ala Ser Lys Tyr Lys Tyr Ser Lys His Arg Ile Asp Ala Leu Asp
1               5                   10                  15

Pro Glu Asn Cys Thr Tyr Ser Phe Ser Val Ile Glu Gly Asp Val Leu
            20                  25                  30

Thr Asp Ile Glu Asn Val Ser Thr Glu Thr Lys Phe Val Ala Ser Pro
        35                  40                  45

Asp Gly Gly Thr Ile Met Lys Ser Thr
    50                  55

<210> SEQ ID NO 36
<211> LENGTH: 57
<212> TYPE: PRT
<213> ORGANISM: Artificial
<220> FEATURE:
<223> OTHER INFORMATION: Cass1/3 fragment

<400> SEQUENCE: 36

Glu Ala Ser Lys Tyr Lys Tyr Ser Arg His Arg Ile Asp Ala Leu Asp
1               5                   10                  15

Pro Glu Asn Cys Thr Tyr Ser Phe Ser Val Ile Glu Gly Asp Val Leu
            20                  25                  30

Thr Asp Ile Glu Asn Val Ser Thr Glu Thr Lys Phe Val Ala Ser Pro
```

```
                 35                  40                  45

Asp Gly Gly Thr Ile Met Lys Ser Thr
    50                  55

<210> SEQ ID NO 37
<211> LENGTH: 57
<212> TYPE: PRT
<213> ORGANISM: Artificial
<220> FEATURE:
<223> OTHER INFORMATION: Cass1/2 fragment

<400> SEQUENCE: 37

Glu Ala Ser Lys Tyr Lys Tyr Ser Lys His Arg Ile Asp Ala Leu Asp
1               5                   10                  15

Pro Glu Asn Cys Thr Tyr Ser Phe Ser Val Ile Glu Gly Asp Val Leu
                20                  25                  30

Thr Asp Ile Glu Asn Val Ser Thr Glu Thr Lys Phe Val Ala Ser Pro
            35                  40                  45

Asp Gly Gly Thr Ile Met Lys Ser Thr
    50                  55

<210> SEQ ID NO 38
<211> LENGTH: 58
<212> TYPE: PRT
<213> ORGANISM: Artificial
<220> FEATURE:
<223> OTHER INFORMATION: Ques1/7 fragment
<220> FEATURE:
<221> NAME/KEY: misc_feature
<222> LOCATION: (35)..(35)
<223> OTHER INFORMATION: Xaa can be any naturally occurring amino acid

<400> SEQUENCE: 38

Glu Ala Ser Lys Phe Lys Tyr Ala Lys His Arg Ile Asp Ala Leu Asp
1               5                   10                  15

Pro Glu Asn Cys Thr Tyr Ser Phe Ser Val Ile Glu Gly Asp Ala Leu
                20                  25                  30

Thr Val Xaa Met Glu Ser Val Ser Thr Glu Ile Lys Cys Val Ala Ser
            35                  40                  45

Pro Asp Gly Gly Ser Ile Met Lys Ser Thr
    50                  55

<210> SEQ ID NO 39
<211> LENGTH: 58
<212> TYPE: PRT
<213> ORGANISM: Artificial
<220> FEATURE:
<223> OTHER INFORMATION: Ques1/8 fragment

<400> SEQUENCE: 39

Glu Gly Ser His Leu Lys His Ala Lys His Arg Ile Asp Val Ile Asp
1               5                   10                  15

Pro Glu Asn Phe Thr Tyr Ser Phe Ser Val Ile Glu Gly Asp Ala Leu
                20                  25                  30

Phe Asp Lys Leu Glu Asn Val Ser Thr Glu Thr Lys Ile Val Ala Ser
            35                  40                  45

Pro Asp Gly Gly Ser Ile Val Lys Ser Thr
    50                  55

<210> SEQ ID NO 40
<211> LENGTH: 58
<212> TYPE: PRT
```

```
<213> ORGANISM: Artificial
<220> FEATURE:
<223> OTHER INFORMATION: Ques1/9 fragment

<400> SEQUENCE: 40

Glu Gly Ser His Leu Lys His Ala Lys His Arg Ile Asp Val Ile Asp
1               5                   10                  15

Pro Glu Asn Phe Thr Tyr Ser Phe Ser Val Ile Glu Gly Asp Ala Leu
            20                  25                  30

Phe Asp Lys Leu Glu Asn Val Ser Thr Glu Thr Lys Ile Val Ala Ser
        35                  40                  45

Pro Asp Gly Gly Ser Ile Ala Lys Ser Thr
    50                  55

<210> SEQ ID NO 41
<211> LENGTH: 57
<212> TYPE: PRT
<213> ORGANISM: Artificial
<220> FEATURE:
<223> OTHER INFORMATION: Mald1.0101 fragment

<400> SEQUENCE: 41

Glu Gly Ser Gln Tyr Gly Tyr Val Lys His Arg Ile Asp Ser Ile Asp
1               5                   10                  15

Glu Ala Ser Tyr Ser Tyr Ser Tyr Thr Leu Ile Glu Gly Asp Ala Leu
            20                  25                  30

Thr Asp Thr Ile Glu Lys Ile Ser Tyr Glu Thr Lys Leu Val Ala Cys
        35                  40                  45

Gly Ser Gly Ser Thr Ile Lys Ser Ile
    50                  55

<210> SEQ ID NO 42
<211> LENGTH: 57
<212> TYPE: PRT
<213> ORGANISM: Artificial
<220> FEATURE:
<223> OTHER INFORMATION: Mald1.0102 fragment

<400> SEQUENCE: 42

Glu Gly Ser Gln Tyr Gly Tyr Val Lys His Arg Ile Asp Ser Ile Asp
1               5                   10                  15

Glu Ala Ser Tyr Ser Tyr Ser Tyr Thr Leu Ile Glu Gly Asp Ala Leu
            20                  25                  30

Thr Asp Thr Ile Glu Lys Ile Ser Tyr Glu Thr Lys Leu Val Ala Cys
        35                  40                  45

Gly Ser Gly Ser Thr Ile Lys Ser Ile
    50                  55

<210> SEQ ID NO 43
<211> LENGTH: 57
<212> TYPE: PRT
<213> ORGANISM: Artificial
<220> FEATURE:
<223> OTHER INFORMATION: Mald1.0109 fragment

<400> SEQUENCE: 43

Glu Gly Ser Gln Tyr Gly Tyr Val Lys His Arg Ile Asp Ser Ile Asp
1               5                   10                  15

Glu Ala Ser Tyr Ser Tyr Ser Tyr Thr Leu Ile Glu Gly Asp Ala Leu
            20                  25                  30

Thr Asp Thr Ile Glu Lys Ile Ser Tyr Glu Thr Lys Leu Val Ala Cys
```

-continued

```
                35                  40                  45

Gly Ser Gly Ser Thr Ile Lys Ser Ile
    50                  55

<210> SEQ ID NO 44
<211> LENGTH: 57
<212> TYPE: PRT
<213> ORGANISM: Artificial
<220> FEATURE:
<223> OTHER INFORMATION: Mald1.0105 fragment

<400> SEQUENCE: 44

Glu Gly Ser Gln Tyr Gly Tyr Val Lys His Arg Ile Asp Ser Ile Asp
1               5                   10                  15

Glu Ala Ser Tyr Ser Tyr Ser Tyr Thr Leu Ile Glu Gly Asp Ala Leu
            20                  25                  30

Thr Asp Thr Ile Glu Lys Ile Ser Tyr Glu Thr Lys Leu Val Ala Cys
        35                  40                  45

Gly Ser Gly Ser Thr Ile Lys Ser Ile
    50                  55

<210> SEQ ID NO 45
<211> LENGTH: 57
<212> TYPE: PRT
<213> ORGANISM: Artificial
<220> FEATURE:
<223> OTHER INFORMATION: Mald1.0106 fragment

<400> SEQUENCE: 45

Glu Gly Ser Gln Tyr Gly Tyr Val Lys His Arg Ile Asp Ser Ile Asp
1               5                   10                  15

Glu Ala Ser Tyr Ser Tyr Ser Tyr Thr Leu Ile Glu Gly Asp Ala Leu
            20                  25                  30

Thr Asp Thr Ile Glu Asn Ile Ser Tyr Glu Thr Lys Leu Val Ala Cys
        35                  40                  45

Gly Ser Gly Ser Thr Ile Lys Ser Ile
    50                  55

<210> SEQ ID NO 46
<211> LENGTH: 57
<212> TYPE: PRT
<213> ORGANISM: Artificial
<220> FEATURE:
<223> OTHER INFORMATION: Mald1.0108 fragment

<400> SEQUENCE: 46

Glu Gly Ser Gln Tyr Gly Tyr Val Lys His Arg Ile Asp Ser Ile Asp
1               5                   10                  15

Glu Ala Ser Tyr Ser Tyr Ser Tyr Thr Leu Ile Glu Gly Asp Ala Leu
            20                  25                  30

Thr Asp Thr Ile Glu Lys Ile Ser Tyr Glu Thr Lys Leu Val Ala Cys
        35                  40                  45

Gly Ser Gly Ser Thr Ile Lys Ser Ile
    50                  55

<210> SEQ ID NO 47
<211> LENGTH: 57
<212> TYPE: PRT
<213> ORGANISM: Artificial
<220> FEATURE:
<223> OTHER INFORMATION: Mald1.0103 fragment
```

-continued

```
<400> SEQUENCE: 47

Glu Gly Ser Gln Tyr Gly Tyr Val Lys His Arg Ile Asp Ser Ile Asp
1               5                   10                  15

Glu Ala Ser Tyr Ser Tyr Ser Tyr Thr Leu Ile Glu Gly Asp Ala Leu
            20                  25                  30

Thr Asp Thr Ile Glu Lys Ile Ser Tyr Glu Thr Lys Leu Val Ala Cys
        35                  40                  45

Gly Ser Gly Ser Thr Ile Lys Ser Ile
    50                  55

<210> SEQ ID NO 48
<211> LENGTH: 57
<212> TYPE: PRT
<213> ORGANISM: Artificial
<220> FEATURE:
<223> OTHER INFORMATION: Mald1.0107 fragment

<400> SEQUENCE: 48

Glu Gly Ser Gln Tyr Gly Tyr Val Lys His Arg Ile Asp Ser Ile Asp
1               5                   10                  15

Glu Ala Ser Tyr Ser Tyr Ser Tyr Thr Leu Ile Glu Gly Asp Ala Leu
            20                  25                  30

Thr Asp Thr Ile Glu Lys Ile Ser Tyr Glu Thr Lys Leu Val Ala Cys
        35                  40                  45

Gly Ser Gly Ser Thr Ile Lys Ser Ile
    50                  55

<210> SEQ ID NO 49
<211> LENGTH: 57
<212> TYPE: PRT
<213> ORGANISM: Artificial
<220> FEATURE:
<223> OTHER INFORMATION: Mald1.0104 fragment

<400> SEQUENCE: 49

Glu Gly Ser Gln Tyr Gly Tyr Val Lys His Arg Ile Asp Ser Ile Asp
1               5                   10                  15

Glu Ala Ser Tyr Ser Tyr Ser Tyr Thr Leu Ile Glu Gly Asp Ala Leu
            20                  25                  30

Thr Asp Thr Ile Glu Lys Ile Ser Tyr Glu Thr Lys Leu Val Ala Cys
        35                  40                  45

Gly Ser Gly Ser Thr Ile Lys Ser Ile
    50                  55

<210> SEQ ID NO 50
<211> LENGTH: 57
<212> TYPE: PRT
<213> ORGANISM: Artificial
<220> FEATURE:
<223> OTHER INFORMATION: Pyrc1.0101 fragment

<400> SEQUENCE: 50

Glu Gly Ser Gln Tyr Gly Tyr Val Lys His Arg Val Asp Ser Ile Asp
1               5                   10                  15

Glu Ala Ser Tyr Ser Tyr Ala Tyr Thr Leu Ile Glu Gly Asp Ala Leu
            20                  25                  30

Thr Asp Thr Ile Glu Lys Ile Ser Tyr Glu Ala Lys Leu Val Ala Ser
        35                  40                  45

Gly Ser Gly Ser Thr Ile Lys Ser Ile
    50                  55
```

-continued

<210> SEQ ID NO 51
<211> LENGTH: 57
<212> TYPE: PRT
<213> ORGANISM: Artificial
<220> FEATURE:
<223> OTHER INFORMATION: Mald1.0201 fragment

<400> SEQUENCE: 51

Glu Gly Ser Gln Tyr Gly Tyr Val Lys His Lys Ile Asp Ser Val Asp
1               5                   10                  15

Glu Ala Asn Tyr Ser Tyr Ala Tyr Thr Leu Ile Glu Gly Asp Ala Leu
            20                  25                  30

Thr Asp Thr Ile Glu Lys Val Ser Tyr Glu Thr Lys Leu Val Ala Ser
        35                  40                  45

Gly Ser Gly Ser Ile Ile Lys Ser Ile
    50                  55

<210> SEQ ID NO 52
<211> LENGTH: 57
<212> TYPE: PRT
<213> ORGANISM: Artificial
<220> FEATURE:
<223> OTHER INFORMATION: Mald1.0202 fragment

<400> SEQUENCE: 52

Glu Gly Ser Gln Tyr Gly Tyr Val Lys His Lys Ile Asp Ser Val Asp
1               5                   10                  15

Glu Ala Asn Tyr Ser Tyr Ala Tyr Thr Leu Ile Glu Gly Asp Ala Leu
            20                  25                  30

Thr Asp Thr Ile Glu Lys Val Ser Tyr Glu Thr Lys Leu Val Ala Ser
        35                  40                  45

Gly Ser Gly Ser Ile Ile Lys Ser Ile
    50                  55

<210> SEQ ID NO 53
<211> LENGTH: 57
<212> TYPE: PRT
<213> ORGANISM: Artificial
<220> FEATURE:
<223> OTHER INFORMATION: Mald1.0203 fragment

<400> SEQUENCE: 53

Glu Gly Ser Gln Tyr Gly Tyr Val Lys His Lys Ile Asp Ser Val Asp
1               5                   10                  15

Glu Ala Asn Tyr Ser Tyr Ala Tyr Thr Leu Ile Glu Gly Asp Ala Leu
            20                  25                  30

Thr Asp Thr Ile Glu Lys Val Ser Tyr Glu Thr Lys Leu Val Ala Ser
        35                  40                  45

Gly Ser Gly Ser Ile Ile Lys Ser Ile
    50                  55

<210> SEQ ID NO 54
<211> LENGTH: 57
<212> TYPE: PRT
<213> ORGANISM: Artificial
<220> FEATURE:
<223> OTHER INFORMATION: Mald1.0207 fragment

<400> SEQUENCE: 54

Glu Gly Ser Gln Tyr Gly Tyr Val Lys His Lys Ile Asp Ser Val Asp
1               5                   10                  15

Glu Ala Asn Tyr Ser Tyr Ala Tyr Thr Leu Ile Glu Gly Asp Ala Leu
                20                  25                  30

Thr Asp Thr Ile Glu Lys Val Ser Tyr Glu Thr Lys Leu Val Ala Ser
            35                  40                  45

Gly Ser Gly Ser Ile Ile Lys Ser Ile
        50                  55

<210> SEQ ID NO 55
<211> LENGTH: 57
<212> TYPE: PRT
<213> ORGANISM: Artificial
<220> FEATURE:
<223> OTHER INFORMATION: Mald1.0205 fragment

<400> SEQUENCE: 55

Glu Gly Ser Gln Tyr Gly Tyr Val Lys His Lys Ile Asp Ser Val Asp
1               5                   10                  15

Glu Ala Asn Tyr Ser Tyr Ala Tyr Thr Leu Ile Glu Gly Asp Ala Leu
                20                  25                  30

Thr Asp Thr Ile Glu Lys Val Ser Tyr Glu Thr Lys Leu Val Ala Ser
            35                  40                  45

Gly Ser Gly Ser Ile Ile Lys Ser Ile
        50                  55

<210> SEQ ID NO 56
<211> LENGTH: 57
<212> TYPE: PRT
<213> ORGANISM: Artificial
<220> FEATURE:
<223> OTHER INFORMATION: Mald1.0204 fragment

<400> SEQUENCE: 56

Glu Gly Ser Gln Tyr Gly Tyr Val Lys His Lys Ile Asp Ser Val Asp
1               5                   10                  15

Glu Ala Asn Tyr Ser Tyr Ala Tyr Thr Leu Ile Glu Gly Asp Ala Leu
                20                  25                  30

Thr Asp Thr Ile Glu Lys Val Ser Tyr Glu Thr Lys Leu Met Ala Ser
            35                  40                  45

Gly Ser Gly Ser Ile Ile Lys Ser Ile
        50                  55

<210> SEQ ID NO 57
<211> LENGTH: 57
<212> TYPE: PRT
<213> ORGANISM: Artificial
<220> FEATURE:
<223> OTHER INFORMATION: Mald1.0206 fragment

<400> SEQUENCE: 57

Glu Gly Ser Gln Tyr Gly Tyr Val Lys His Lys Ile Asp Ser Val Asp
1               5                   10                  15

Glu Ala Asn Tyr Ser Tyr Ala Tyr Thr Leu Ile Glu Gly Asp Ala Leu
                20                  25                  30

Thr Asp Thr Ile Glu Lys Val Ser Tyr Glu Thr Lys Leu Val Ala Ser
            35                  40                  45

Gly Ser Gly Ser Ile Ile Lys Ser Ile
        50                  55

<210> SEQ ID NO 58
<211> LENGTH: 57

```
<212> TYPE: PRT
<213> ORGANISM: Artificial
<220> FEATURE:
<223> OTHER INFORMATION: Mald1.0208 fragment

<400> SEQUENCE: 58

Glu Gly Ser Gln Tyr Gly Tyr Val Lys His Lys Ile Asp Ser Val Asp
1               5                   10                  15

Glu Ala Asn Tyr Ser Tyr Ala Tyr Thr Leu Ile Glu Gly Asp Ala Leu
            20                  25                  30

Thr Asp Thr Ile Glu Lys Val Ser Tyr Glu Thr Lys Leu Val Ala Ser
        35                  40                  45

Gly Ser Gly Ser Ile Ile Lys Ser Ile
    50                  55

<210> SEQ ID NO 59
<211> LENGTH: 58
<212> TYPE: PRT
<213> ORGANISM: Artificial
<220> FEATURE:
<223> OTHER INFORMATION: Pruav1.0101 fragment

<400> SEQUENCE: 59

Glu Gly Ser Gln Tyr Gly Tyr Val Lys His Lys Ile Asp Ser Ile Asp
1               5                   10                  15

Lys Glu Asn Tyr Ser Tyr Ser Tyr Thr Leu Ile Glu Gly Asp Ala Leu
            20                  25                  30

Gly Asp Thr Leu Glu Lys Ile Ser Tyr Glu Thr L

```
Ser Glu Thr Ile Glu Lys Ile Ser Tyr Thr Lys Leu Val Ala Ala
        35                  40                  45

Gly Ser Gly Ser Val Ile Lys Ser Thr
    50                  55
```

<210> SEQ ID NO 62
<211> LENGTH: 57
<212> TYPE: PRT
<213> ORGANISM: Artificial
<220> FEATURE:
<223> OTHER INFORMATION: Mald1.0304 fragment

<400> SEQUENCE: 62

```
Glu Gly Ser Thr Tyr Ser Tyr Val Lys His Arg Ile Asp Gly Val Asp
1               5                   10                  15

Lys Glu Asn Phe Val Tyr Lys Tyr Ser Val Ile Glu Gly Asp Ala Ile
                20                  25                  30

Ser Glu Thr Ile Glu Lys Ile Ser Tyr Glu Thr Lys Leu Val Ala Ser
        35                  40                  45

Gly Ser Gly Ser Val Ile Lys Ser Thr
    50                  55
```

<210> SEQ ID NO 63
<211> LENGTH: 57
<212> TYPE: PRT
<213> ORGANISM: Artificial
<220> FEATURE:
<223> OTHER INFORMATION: Mald1.0303 fragment

<400> SEQUENCE: 63

```
Glu Gly Ser Thr Tyr Ser Tyr Val Lys His Lys Ile Asp Gly Val Asp
1               5                   10                  15

Lys Asp Asn Phe Val Tyr Gln Tyr Ser Val Ile Glu Gly Asp Ala Ile
                20                  25                  30

Ser Glu Thr Ile Glu Lys Ile Ser Tyr Glu Thr Lys Leu Val Ala Ser
        35                  40                  45

Gly Ser Gly Ser Val Ile Lys Ser Ile
    50                  55
```

<210> SEQ ID NO 64
<211> LENGTH: 57
<212> TYPE: PRT
<213> ORGANISM: Artificial
<220> FEATURE:
<223> OTHER INFORMATION: Mald1.0301 fragment

<400> SEQUENCE: 64

```
Glu Gly Ser Thr Tyr Ser Tyr Val Lys His Arg Ile Asp Gly Val Asp
1               5                   10                  15

Lys Glu Asn Phe Val Tyr Lys Tyr Ser Val Ile Glu Gly Asp Ala Ile
                20                  25                  30

Ser Glu Thr Ile Glu Lys Ile Ser Tyr Glu Thr Lys Leu Val Ala Ser
        35                  40                  45

Gly Ser Gly Ser Val Ile Lys Ser Thr
    50                  55
```

<210> SEQ ID NO 65
<211> LENGTH: 58
<212> TYPE: PRT
<213> ORGANISM: Artificial
<220> FEATURE:
<223> OTHER INFORMATION: Pruav1.0202 fragment

<400> SEQUENCE: 65

Glu Gly Ser His Tyr Ser Tyr Val Lys His Arg Ile Asp Gly Leu Asp
1               5                   10                  15

Lys Asp Asn Phe Val Tyr Ser Tyr Ser Leu Val Glu Gly Asp Ala Leu
            20                  25                  30

Ser Asp Lys Val Glu Lys Ile Ser Tyr Glu Ile Lys Leu Val Ala Ser
        35                  40                  45

Ala Asp Gly Gly Ser Ile Ile Lys Ser Thr
    50                  55

<210> SEQ ID NO 66
<211> LENGTH: 58
<212> TYPE: PRT
<213> ORGANISM: Artificial
<220> FEATURE:
<223> OTHER INFORMATION: Pruav1.0203 fragment

<400> SEQUENCE: 66

Glu Gly Ser His Tyr Ser Tyr Val Lys His Arg Ile Asp Gly Leu Asp
1               5                   10                  15

Lys Asp Asn Phe Val Tyr Ser Tyr Ser Leu Val Glu Gly Asp Ala Leu
            20                  25                  30

Ser Asp Lys Val Glu Lys Ile Ser Tyr Glu Ile Lys Leu Val Ala Ser
        35                  40                  45

Ala Asp Gly Gly Ser Ile Ile Lys Ser Thr
    50                  55

<210> SEQ ID NO 67
<211> LENGTH: 58
<212> TYPE: PRT
<213> ORGANISM: Artificial
<220> FEATURE:
<223> OTHER INFORMATION: Pruav1.0201 fragment

<400> SEQUENCE: 67

Glu Gly Ser His Tyr Ser Tyr Val Lys His Arg Ile Asp Gly Leu Asp
1               5                   10                  15

Lys Asp Asn Phe Val Tyr Asn Tyr Thr Leu Val Glu Gly Asp Ala Leu
            20                  25                  30

Ser Asp Lys Ile Glu Lys Ile Thr Tyr Glu Ile Lys Leu Val Ala Ser
        35                  40                  45

Ala Asp Gly Gly Ser Ile Ile Lys Ser Thr
    50                  55

<210> SEQ ID NO 68
<211> LENGTH: 57
<212> TYPE: PRT
<213> ORGANISM: Artificial
<220> FEATURE:
<223> OTHER INFORMATION: Rubi1.0101 fragment

<400> SEQUENCE: 68

Glu Gly Thr Glu His Ser Tyr Val Lys His Lys Ile Asp Gly Leu Asp
1               5                   10                  15

Lys Val Asn Phe Val Tyr Ser Tyr Ser Ile Thr Glu Gly Asp Ala Leu
            20                  25                  30

Gly Asp Lys Ile Glu Lys Ile Ser Tyr Glu Ile Lys Leu Val Ala Ser
        35                  40                  45

Gly Arg Gly Ser Ile Ile Lys Thr Thr

<210> SEQ ID NO 69
<211> LENGTH: 58
<212> TYPE: PRT
<213> ORGANISM: Artificial
<220> FEATURE:
<223> OTHER INFORMATION: Mald1.0402 fragment

<400> SEQUENCE: 69

Glu Gly Ser Gln Tyr Gly Tyr Val Lys Gln Arg Val Asn Gly Ile Asp
1               5                   10                  15

Lys Asp Asn Phe Thr Tyr Ser Tyr Ser Met Ile Glu Gly Asp Thr Leu
            20                  25                  30

Ser Asp Lys Leu Glu Lys Ile Thr Tyr Glu Thr Lys Leu Ile Ala Ser
        35                  40                  45

Pro Asp Gly Gly Ser Ile Ile Lys Thr Asn
    50                  55

<210> SEQ ID NO 70
<211> LENGTH: 58
<212> TYPE: PRT
<213> ORGANISM: Artificial
<220> FEATURE:
<223> OTHER INFORMATION: Mald1.0403 fragment

<400> SEQUENCE: 70

Glu Gly Ser Gln Tyr Gly Tyr Val Lys Gln Arg Val Asn Gly Ile Asp
1               5                   10                  15

Lys Asp Asn Phe Thr Tyr Ser Tyr Ser Met Ile Glu Gly Asp Thr Leu
            20                  25                  30

Ser Asp Lys Leu Glu Lys Ile Thr Tyr Glu Thr Lys Leu Ile Ala Ser
        35                  40                  45

Pro Asp Gly Gly Ser Ile Ile Lys Thr Thr
    50                  55

<210> SEQ ID NO 71
<211> LENGTH: 58
<212> TYPE: PRT
<213> ORGANISM: Artificial
<220> FEATURE:
<223> OTHER INFORMATION: Mald1.0401 fragment

<400> SEQUENCE: 71

Glu Gly Ser Gln Tyr Gly Tyr Val Lys Gln Arg Val Asn Gly Ile Asp
1               5                   10                  15

Lys Asp Asn Phe Thr Tyr Ser Tyr Ser Met Ile Glu Gly Asp Thr Leu
            20                  25                  30

Ser Asp Lys Leu Glu Lys Ile Thr Tyr Glu Thr Lys Leu Ile Ala Ser
        35                  40                  45

Pro Asp Gly Gly Ser Ile Ile Lys Thr Thr
    50                  55

<210> SEQ ID NO 72
<211> LENGTH: 58
<212> TYPE: PRT
<213> ORGANISM: Artificial
<220> FEATURE:
<223> OTHER INFORMATION: Pruar1.0101 fragment

<400> SEQUENCE: 72

Glu Gly Ser Gln Tyr Ala Tyr Val Lys His Arg Val Asp Gly Ile Asp

```
1               5                   10                  15
Lys Asp Asn Leu Ser Tyr Ser Tyr Thr Leu Ile Glu Gly Asp Ala Leu
                20                  25                  30

Ser Asp Val Ile Glu Asn Ile Ala Tyr Asp Ile Lys Leu Val Ala Ser
                35                  40                  45

Pro Asp Gly Gly Ser Ile Val Lys Thr Thr
                50                  55

<210> SEQ ID NO 73
<211> LENGTH: 59
<212> TYPE: PRT
<213> ORGANISM: Artificial
<220> FEATURE:
<223> OTHER INFORMATION: Coral.0401 fragment

<400> SEQUENCE: 73

Glu Gly Asn Glu Phe Lys Tyr Met Lys His Lys Val Glu Glu Ile Asp
1               5                   10                  15

His Ala Asn Phe Lys Tyr Cys Tyr Ser Ile Ile Glu Gly Gly Pro Leu
                20                  25                  30

Gly His Thr Leu Glu Lys Ile Ser Tyr Glu Ile Lys Met Ala Ala Ala
                35                  40                  45

Pro His Gly Gly Gly Ser Ile Leu Lys Ile Thr
                50                  55

<210> SEQ ID NO 74
<211> LENGTH: 59
<212> TYPE: PRT
<213> ORGANISM: Artificial
<220> FEATURE:
<223> OTHER INFORMATION: Coral.0404 fragment

<400> SEQUENCE: 74

Glu Gly Asn Glu Phe Lys Tyr Met Lys His Lys Val Glu Glu Ile Asp
1               5                   10                  15

His Ala Asn Phe Lys Tyr Cys Tyr Ser Ile Ile Glu Gly Gly Pro Leu
                20                  25                  30

Gly His Thr Leu Glu Lys Ile Pro Tyr Glu Ile Lys Met Ala Ala Ala
                35                  40                  45

Pro His Gly Gly Gly Ser Ile Leu Lys Ile Thr
                50                  55

<210> SEQ ID NO 75
<211> LENGTH: 59
<212> TYPE: PRT
<213> ORGANISM: Artificial
<220> FEATURE:
<223> OTHER INFORMATION: Coral.0402 fragment

<400> SEQUENCE: 75

Glu Gly Ser Glu Phe Lys Tyr Met Lys His Lys Val Glu Glu Ile Asp
1               5                   10                  15

His Ala Asn Phe Lys Tyr Cys Tyr Ser Ile Ile Glu Gly Gly Pro Leu
                20                  25                  30

Gly His Thr Leu Glu Lys Ile Ser Tyr Glu Ile Lys Met Ala Ala Ala
                35                  40                  45

Pro His Gly Gly Gly Ser Ile Leu Lys Ile Thr
                50                  55

<210> SEQ ID NO 76
```

-continued

```
<211> LENGTH: 59
<212> TYPE: PRT
<213> ORGANISM: Artificial
<220> FEATURE:
<223> OTHER INFORMATION: Cora1.0403 fragment

<400> SEQUENCE: 76

Glu Gly Ser Glu Phe Lys Tyr Met Lys His Lys Val Glu Glu Ile Asp
1               5                   10                  15

His Ala Asn Phe Lys Tyr Cys Tyr Ser Ile Ile Glu Gly Gly Pro Leu
            20                  25                  30

Gly His Thr Leu Glu Lys Ile Ser Tyr Glu Ile Lys Met Ala Ala Ala
        35                  40                  45

Pro His Gly Gly Gly Ser Ile Leu Lys Ile Thr
    50                  55

<210> SEQ ID NO 77
<211> LENGTH: 58
<212> TYPE: PRT
<213> ORGANISM: Artificial
<220> FEATURE:
<223> OTHER INFORMATION: Cora1.0301 fragment

<400> SEQUENCE: 77

Glu Gly Ser Pro Phe Asn Tyr Ile Lys Gln Lys Val Glu Glu Ile Asp
1               5                   10                  15

Gln Ala Asn Phe Ser Tyr Arg Tyr Ser Val Ile Glu Gly Asp Ala Leu
            20                  25                  30

Ser Asp Lys Leu Glu Lys Ile Asn Tyr Glu Ile Lys Ile Val Ala Ser
        35                  40                  45

Pro His Gly Gly Ser Ile Leu Lys Ser Ile
    50                  55

<210> SEQ ID NO 78
<211> LENGTH: 58
<212> TYPE: PRT
<213> ORGANISM: Artificial
<220> FEATURE:
<223> OTHER INFORMATION: Betv1d fragment

<400> SEQUENCE: 78

Glu Gly Phe Pro Phe Lys Tyr Val Lys Asp Arg Val Asp Glu Val Asp
1               5                   10                  15

His Thr Asn Phe Lys Tyr Asn Tyr Ser Val Ile Glu Gly Gly Pro Val
            20                  25                  30

Gly Asp Thr Leu Glu Lys Ile Ser Asn Glu Ile Lys Ile Val Ala Thr
        35                  40                  45

Pro Asp Gly Gly Cys Val Leu Lys Ile Ser
    50                  55

<210> SEQ ID NO 79
<211> LENGTH: 58
<212> TYPE: PRT
<213> ORGANISM: Artificial
<220> FEATURE:
<223> OTHER INFORMATION: Betv1l fragment

<400> SEQUENCE: 79

Glu Gly Phe Pro Phe Lys Tyr Val Lys Asp Arg Val Asp Glu Val Asp
1               5                   10                  15

His Thr Asn Phe Lys Tyr Asn Tyr Ser Val Ile Glu Gly Gly Pro Val
            20                  25                  30
```

```
Gly Asp Thr Leu Glu Lys Ile Ser Asn Glu Ile Lys Ile Val Ala Thr
        35                  40                  45

Pro Asp Gly Gly Cys Val Leu Lys Ile Ser
    50                  55

<210> SEQ ID NO 80
<211> LENGTH: 58
<212> TYPE: PRT
<213> ORGANISM: Artificial
<220> FEATURE:
<223> OTHER INFORMATION: Betv1a1-6 fragment

<400> SEQUENCE: 80

Glu Gly Phe Pro Phe Lys Tyr Val Lys Asp Arg Val Asp Glu Val Asp
1               5                   10                  15

His Thr Asn Phe Lys Tyr Asn Tyr Ser Val Ile Glu Gly Gly Pro Ile
            20                  25                  30

Gly Asp Thr Leu Glu Lys Ile Ser Asn Glu Ile Lys Ile Val Ala Thr
        35                  40                  45

Pro Asp Gly Gly Cys Val Leu Lys Ile Ser
    50                  55

<210> SEQ ID NO 81
<211> LENGTH: 58
<212> TYPE: PRT
<213> ORGANISM: Artificial
<220> FEATURE:
<223> OTHER INFORMATION: Betv1g fragment

<400> SEQUENCE: 81

Glu Gly Phe Pro Phe Lys Tyr Val Lys Asp Arg Val Asp Glu Val Asp
1               5                   10                  15

His Thr Asn Phe Lys Tyr Asn Tyr Ser Val Ile Glu Gly Gly Pro Val
            20                  25                  30

Gly Asp Thr Leu Glu Lys Ile Ser Asn Glu Ile Lys Ile Val Ala Thr
        35                  40                  45

Pro Asp Gly Gly Cys Val Leu Lys Ile Ser
    50                  55

<210> SEQ ID NO 82
<211> LENGTH: 58
<212> TYPE: PRT
<213> ORGANISM: Artificial
<220> FEATURE:
<223> OTHER INFORMATION: Betv1a fragment

<400> SEQUENCE: 82

Glu Gly Phe Pro Phe Lys Tyr Val Lys Asp Arg Val Asp Glu Val Asp
1               5                   10                  15

His Thr Asn Phe Lys Tyr Asn Tyr Ser Val Ile Glu Gly Gly Pro Ile
            20                  25                  30

Gly Asp Thr Leu Glu Lys Ile Ser Asn Glu Ile Lys Ile Val Ala Thr
        35                  40                  45

Pro Asp Gly Gly Ser Ile Leu Lys Ile Ser
    50                  55

<210> SEQ ID NO 83
<211> LENGTH: 58
<212> TYPE: PRT
<213> ORGANISM: Artificial
<220> FEATURE:
```

-continued

<223> OTHER INFORMATION: Betv1f fragment

<400> SEQUENCE: 83

Glu Gly Phe Pro Phe Lys Tyr Val Lys Asp Arg Val Asp Glu Val Asp
1               5                   10                  15

His Thr Asn Phe Lys Tyr Ser Tyr Ser Val Ile Glu Gly Gly Pro Val
            20                  25                  30

Gly Asp Thr Leu Glu Lys Ile Ser Asn Glu Ile Lys Ile Val Ala Thr
        35                  40                  45

Pro Asn Gly Gly Ser Ile Leu Lys Ile Asn
    50                  55

<210> SEQ ID NO 84
<211> LENGTH: 58
<212> TYPE: PRT
<213> ORGANISM: Artificial
<220> FEATURE:
<223> OTHER INFORMATION: Betv1j fragment

<400> SEQUENCE: 84

Glu Gly Phe Pro Phe Lys Tyr Val Lys Asp Arg Val Asp Glu Val Asp
1               5                   10                  15

His Thr Asn Phe Lys Tyr Ser Tyr Ser Val Ile Glu Gly Gly Pro Val
            20                  25                  30

Gly Asp Thr Leu Glu Lys Ile Ser Asn Glu Ile Lys Ile Val Ala Thr
        35                  40                  45

Pro Asn Gly Gly Ser Ile Leu Lys Ile Asn
    50                  55

<210> SEQ ID NO 85
<211> LENGTH: 58
<212> TYPE: PRT
<213> ORGANISM: Artificial
<220> FEATURE:
<223> OTHER INFORMATION: Betv1e fragment

<400> SEQUENCE: 85

Glu Gly Ile Pro Phe Lys Tyr Val Lys Gly Arg Val Asp Glu Val Asp
1               5                   10                  15

His Thr Asn Phe Lys Tyr Ser Tyr Ser Val Ile Glu Gly Gly Pro Val
            20                  25                  30

Gly Asp Thr Leu Glu Lys Ile Ser Asn Glu Ile Lys Ile Val Ala Thr
        35                  40                  45

Pro Asn Gly Gly Ser Ile Leu Lys Ile Asn
    50                  55

<210> SEQ ID NO 86
<211> LENGTH: 58
<212> TYPE: PRT
<213> ORGANISM: Artificial
<220> FEATURE:
<223> OTHER INFORMATION: Betv1b fragment

<400> SEQUENCE: 86

Glu Gly Ser Pro Phe Lys Tyr Val Lys Glu Arg Val Asp Glu Val Asp
1               5                   10                  15

His Ala Asn Phe Lys Tyr Ser Tyr Ser Met Ile Glu Gly Gly Ala Leu
            20                  25                  30

Gly Asp Thr Leu Glu Lys Ile Cys Asn Glu Ile Lys Ile Val Ala Thr
        35                  40                  45

-continued

```
Pro Asp Gly Gly Ser Ile Leu Lys Ile Ser
    50                  55

<210> SEQ ID NO 87
<211> LENGTH: 58
<212> TYPE: PRT
<213> ORGANISM: Artificial
<220> FEATURE:
<223> OTHER INFORMATION: Betv1c fragment

<400> SEQUENCE: 87

Glu Gly Ser Pro Phe Lys Tyr Val Lys Glu Arg Val Asp Glu Val Asp
1               5                   10                  15

His Ala Asn Phe Lys Tyr Ser Tyr Ser Met Ile Glu Gly Gly Ala Leu
            20                  25                  30

Gly Asp Thr Leu Glu Lys Ile Cys Asn Glu Ile Lys Ile Val Ala Thr
        35                  40                  45

Pro Asp Gly Gly Ser Ile Leu Lys Ile Ser
    50                  55

<210> SEQ ID NO 88
<211> LENGTH: 58
<212> TYPE: PRT
<213> ORGANISM: Artificial
<220> FEATURE:
<223> OTHER INFORMATION: Alng1 fragment

<400> SEQUENCE: 88

Glu Gly Ser Pro Phe Lys Tyr Val Lys Glu Arg Val Asp Glu Val Asp
1               5                   10                  15

Arg Val Asn Phe Lys Tyr Ser Phe Ser Val Ile Glu Gly Gly Ala Val
            20                  25                  30

Gly Asp Ala Leu Glu Lys Val Cys Asn Glu Ile Lys Ile Val Ala Ala
        35                  40                  45

Pro Asp Gly Gly Ser Ile Leu Lys Ile Ser
    50                  55

<210> SEQ ID NO 89
<211> LENGTH: 58
<212> TYPE: PRT
<213> ORGANISM: Artificial
<220> FEATURE:
<223> OTHER INFORMATION: Carb1.0301 fragment

<400> SEQUENCE: 89

Glu Gly Ser Pro Val Lys Tyr Val Lys Glu Arg Val Glu Glu Val Asp
1               5                   10                  15

His Thr Asn Phe Lys Tyr Ser Tyr Thr Val Ile Glu Gly Gly Phe Val
            20                  25                  30

Gly Asp Lys Val Glu Lys Ile Cys Asn Glu Ile Lys Ile Val Ala Ala
        35                  40                  45

Pro Asp Gly Gly Ser Ile Leu Lys Ile Thr
    50                  55

<210> SEQ ID NO 90
<211> LENGTH: 58
<212> TYPE: PRT
<213> ORGANISM: Artificial
<220> FEATURE:
<223> OTHER INFORMATION: Carb1.0302 fragment

<400> SEQUENCE: 90
```

-continued

Glu Gly Ser Pro Val Lys Tyr Val Lys Glu Arg Val Glu Glu Val Asp
1               5                   10                  15

His Thr Asn Phe Lys Tyr Ser Tyr Thr Val Ile Glu Gly Gly Pro Val
            20                  25                  30

Gly Asp Lys Val Glu Lys Ile Cys Asn Glu Ile Lys Ile Val Ala Ala
        35                  40                  45

Pro Asp Gly Gly Ser Ile Leu Lys Ile Thr
    50                  55

<210> SEQ ID NO 91
<211> LENGTH: 58
<212> TYPE: PRT
<213> ORGANISM: Artificial
<220> FEATURE:
<223> OTHER INFORMATION: Coral.0201 fragment

<400> SEQUENCE: 91

Glu Gly Ser Pro Phe Lys Tyr Val Lys Glu Arg Val Glu Glu Val Asp
1               5                   10                  15

His Thr Asn Phe Lys Tyr Ser Tyr Thr Val Ile Glu Gly Gly Pro Val
            20                  25                  30

Gly Asp Lys Val Glu Lys Ile Cys Asn Glu Ile Lys Ile Val Ala Ala
        35                  40                  45

Pro Asp Gly Gly Ser Ile Leu Lys Ile Ser
    50                  55

<210> SEQ ID NO 92
<211> LENGTH: 58
<212> TYPE: PRT
<213> ORGANISM: Artificial
<220> FEATURE:
<223> OTHER INFORMATION: Carb1.0103 fragment

<400> SEQUENCE: 92

Glu Gly Ser Pro Phe Lys Phe Val Lys Glu Arg Val Asp Glu Val Asp
1               5                   10                  15

Asn Ala Asn Phe Lys Tyr Asn Tyr Thr Val Ile Glu Gly Asp Val Leu
            20                  25                  30

Gly Asp Lys Leu Glu Lys Val Ser His Glu Leu Lys Ile Val Ala Ala
        35                  40                  45

Pro Gly Gly Gly Ser Ile Val Lys Ile Ser
    50                  55

<210> SEQ ID NO 93
<211> LENGTH: 58
<212> TYPE: PRT
<213> ORGANISM: Artificial
<220> FEATURE:
<223> OTHER INFORMATION: Carb1.0105 fragment

<400> SEQUENCE: 93

Glu Gly Ser Pro Phe Lys Phe Val Lys Glu Arg Val Asp Glu Val Asp
1               5                   10                  15

Asn Ala Asn Phe Lys Tyr Asn Tyr Thr Val Ile Glu Gly Asp Val Leu
            20                  25                  30

Gly Asp Lys Leu Glu Lys Val Ser His Glu Leu Lys Ile Val Ala Ala
        35                  40                  45

Pro Gly Gly Gly Ser Ile Val Lys Ile Ser
    50                  55

```
<210> SEQ ID NO 94
<211> LENGTH: 58
<212> TYPE: PRT
<213> ORGANISM: Artificial
<220> FEATURE:
<223> OTHER INFORMATION: Carb1.0104 fragment

<400> SEQUENCE: 94

Glu Gly Ser Pro Phe Lys Phe Val Lys Glu Arg Val Asp Glu Val Asp
1               5                   10                  15

Asn Ala Asn Phe Lys Tyr Asn Tyr Thr Val Ile Glu Gly Asp Val Leu
            20                  25                  30

Gly Asp Asn Leu Glu Lys Val Ser His Glu Leu Lys Ile Val Ala Ala
        35                  40                  45

Pro Gly Gly Gly Ser Ile Val Lys Ile Ser
    50                  55

<210> SEQ ID NO 95
<211> LENGTH: 58
<212> TYPE: PRT
<213> ORGANISM: Artificial
<220> FEATURE:
<223> OTHER INFORMATION: Carb1/3 fragment

<400> SEQUENCE: 95

Glu Gly Ser Pro Phe Lys Phe Val Lys Glu Arg Val Asp Glu Val Asp
1               5                   10                  15

Asn Ala Asn Phe Lys Tyr Asn Tyr Thr Val Ile Glu Gly Asp Val Leu
            20                  25                  30

Gly Asp Lys Leu Glu Lys Val Ser His Glu Leu Lys Ile Val Ala Ala
        35                  40                  45

Pro Gly Gly Gly Ser Ile Val Lys Ile Ser
    50                  55

<210> SEQ ID NO 96
<211> LENGTH: 58
<212> TYPE: PRT
<213> ORGANISM: Artificial
<220> FEATURE:
<223> OTHER INFORMATION: Carb1/1a fragment

<400> SEQUENCE: 96

Glu Gly Ile Pro Phe Lys Phe Val Lys Glu Arg Val Asp Glu Val Asp
1               5                   10                  15

Asn Ala Asn Phe Lys Tyr Asn Tyr Thr Val Ile Glu Gly Asp Val Leu
            20                  25                  30

Gly Asp Lys Leu Glu Lys Val Ser His Glu Leu Lys Ile Val Ala Ala
        35                  40                  45

Pro Gly Gly Gly Ser Ile Val Lys Ile Ser
    50                  55

<210> SEQ ID NO 97
<211> LENGTH: 58
<212> TYPE: PRT
<213> ORGANISM: Artificial
<220> FEATURE:
<223> OTHER INFORMATION: Carb1.0101 fragment

<400> SEQUENCE: 97

Glu Gly Ile Pro Phe Lys Phe Val Lys Glu Arg Val Asp Glu Val Asp
1               5                   10                  15

Asn Ala Asn Phe Lys Tyr Asn Tyr Thr Val Ile Glu Gly Asp Val Leu
```

```
                 20                  25                  30

Gly Asp Lys Leu Glu Lys Val Ser His Glu Leu Lys Ile Val Ala Ala
         35                  40                  45

Pro Gly Gly Gly Ser Ile Val Lys Ile Ser
     50                  55

<210> SEQ ID NO 98
<211> LENGTH: 58
<212> TYPE: PRT
<213> ORGANISM: Artificial
<220> FEATURE:
<223> OTHER INFORMATION: Carb1.0102 fragment

<400> SEQUENCE: 98

Glu Gly Ile Pro Phe Lys Phe Val Lys Glu Arg Val Asp Glu Val Asp
1               5                   10                  15

Asn Ala Asn Phe Lys Tyr Asn Tyr Thr Val Ile Glu Gly Asp Val Leu
             20                  25                  30

Gly Asp Lys Leu Glu Lys Val Ser His Glu Leu Lys Ile Val Ala Ala
         35                  40                  45

Pro Gly Gly Gly Ser Ile Val Lys Ile Ser
     50                  55

<210> SEQ ID NO 99
<211> LENGTH: 58
<212> TYPE: PRT
<213> ORGANISM: Artificial
<220> FEATURE:
<223> OTHER INFORMATION: Carb1/1b fragment

<400> SEQUENCE: 99

Glu Gly Ser Pro Phe Lys Phe Val Lys Glu Arg Val Asp Glu Val Asp
1               5                   10                  15

Asn Ala Asn Phe Lys Tyr Asn Tyr Thr Val Ile Glu Gly Asp Val Leu
             20                  25                  30

Gly Asp Lys Leu Glu Lys Val Ser His Glu Leu Lys Ile Val Ala Ala
         35                  40                  45

Pro Gly Gly Gly Ser Ile Val Lys Ile Ser
     50                  55

<210> SEQ ID NO 100
<211> LENGTH: 58
<212> TYPE: PRT
<213> ORGANISM: Artificial
<220> FEATURE:
<223> OTHER INFORMATION: Carb1/5 fragment

<400> SEQUENCE: 100

Glu Gly Ile Pro Phe Lys Phe Val Lys Glu Arg Val Asp Glu Val Asp
1               5                   10                  15

Asn Ala Asn Phe Lys Tyr Ser Tyr Thr Val Ile Glu Gly Asp Val Leu
             20                  25                  30

Gly Asp Lys Leu Glu Lys Val Ser His Glu Leu Lys Ile Val Ala Ala
         35                  40                  45

Pro Gly Gly Gly Ser Ile Val Lys Ile Ser
     50                  55

<210> SEQ ID NO 101
<211> LENGTH: 58
<212> TYPE: PRT
<213> ORGANISM: Artificial
```

```
<220> FEATURE:
<223> OTHER INFORMATION: Carb1/2 fragment

<400> SEQUENCE: 101

Glu Gly Ser Pro Phe Lys Phe Val Lys Glu Arg Val Asp Glu Val Asp
1               5                   10                  15

Asn Ala Asn Phe Lys Tyr Asn Tyr Thr Val Ile Glu Gly Asp Val Leu
            20                  25                  30

Gly Asp Lys Leu Glu Lys Val Ser His Glu Leu Lys Ile Val Ala Ala
        35                  40                  45

Pro Gly Gly Gly Ser Val Val Lys Ile Ser
    50                  55

<210> SEQ ID NO 102
<211> LENGTH: 58
<212> TYPE: PRT
<213> ORGANISM: Artificial
<220> FEATURE:
<223> OTHER INFORMATION: Carb1/4 fragment

<400> SEQUENCE: 102

Glu Gly Ser Pro Phe Lys Phe Val Lys Glu Arg Val Asp Glu Val Asp
1               5                   10                  15

Asn Ala Asn Phe Lys Tyr Asn Tyr Thr Val Ile Glu Gly Asp Val Leu
            20                  25                  30

Gly Asp Lys Leu Glu Lys Val Ser His Glu Leu Lys Ile Val Ala Ala
        35                  40                  45

Pro Gly Gly Gly Ser Ile Val Lys Ile Ser
    50                  55

<210> SEQ ID NO 103
<211> LENGTH: 58
<212> TYPE: PRT
<213> ORGANISM: Artificial
<220> FEATURE:
<223> OTHER INFORMATION: Carb1.0106a fragment

<400> SEQUENCE: 103

Glu Gly Ser Pro Phe Lys Phe Val Lys Glu Arg Val Asp Glu Val Asp
1               5                   10                  15

Asn Ala Asn Phe Lys Tyr Asn Tyr Thr Val Ile Glu Gly Asp Val Leu
            20                  25                  30

Gly Asp Lys Leu Glu Lys Val Ser His Glu Leu Lys Ile Val Ala Ala
        35                  40                  45

Pro Gly Gly Gly Ser Ile Val Lys Ile Ser
    50                  55

<210> SEQ ID NO 104
<211> LENGTH: 58
<212> TYPE: PRT
<213> ORGANISM: Artificial
<220> FEATURE:
<223> OTHER INFORMATION: Carb1.0106b fragment

<400> SEQUENCE: 104

Glu Gly Ser Pro Phe Lys Phe Val Lys Glu Arg Val Asp Glu Val Asp
1               5                   10                  15

Asn Ala Asn Phe Lys Tyr Asn Tyr Thr Val Ile Glu Gly Asp Val Leu
            20                  25                  30

Gly Asp Lys Leu Glu Lys Val Ser His Glu Leu Lys Ile Val Ala Ala
        35                  40                  45
```

```
Pro Gly Gly Gly Ser Ile Val Lys Ile Ser
    50                  55
```

<210> SEQ ID NO 105
<211> LENGTH: 58
<212> TYPE: PRT
<213> ORGANISM: Artificial
<220> FEATURE:
<223> OTHER INFORMATION: Carb1.0106c fragment

<400> SEQUENCE: 105

```
Glu Gly Ser Pro Phe Lys Phe Val Lys Glu Arg Val Asp Glu Val Asp
1               5                   10                  15

Asn Ala Asn Phe Lys Tyr Asn Tyr Thr Val Ile Glu Gly Asp Val Leu
            20                  25                  30

Gly Asp Lys Leu Glu Lys Val Ser His Glu Leu Lys Ile Val Ala Ala
        35                  40                  45

Pro Gly Gly Gly Ser Ile Val Lys Ile Ser
    50                  55
```

<210> SEQ ID NO 106
<211> LENGTH: 58
<212> TYPE: PRT
<213> ORGANISM: Artificial
<220> FEATURE:
<223> OTHER INFORMATION: Carb1.0106d fragment

<400> SEQUENCE: 106

```
Glu Gly Ser Pro Phe Lys Phe Val Lys Glu Arg Val Asp Glu Val Asp
1               5                   10                  15

Asn Ala Asn Phe Lys Tyr Asn Tyr Thr Val Ile Glu Gly Asp Val Leu
            20                  25                  30

Gly Asp Lys Leu Glu Lys Val Ser His Glu Leu Lys Ile Val Ala Ala
        35                  40                  45

Pro Gly Gly Gly Ser Ile Val Lys Ile Ser
    50                  55
```

<210> SEQ ID NO 107
<211> LENGTH: 58
<212> TYPE: PRT
<213> ORGANISM: Artificial
<220> FEATURE:
<223> OTHER INFORMATION: Carb1/1 fragment

<400> SEQUENCE: 107

```
Glu Gly Ser Pro Phe Lys Phe Val Lys Glu Arg Val Asp Glu Val Asp
1               5                   10                  15

Asn Ala Asn Phe Lys Tyr Asn Tyr Thr Val Ile Glu Gly Asp Val Leu
            20                  25                  30

Gly Asp Lys Leu Glu Lys Val Ser His Glu Leu Lys Ile Val Ala Ala
        35                  40                  45

Pro Gly Gly Gly Ser Ile Leu Lys Ile Ser
    50                  55
```

<210> SEQ ID NO 108
<211> LENGTH: 58
<212> TYPE: PRT
<213> ORGANISM: Artificial
<220> FEATURE:
<223> OTHER INFORMATION: Carb1.0107 fragment

<400> SEQUENCE: 108

-continued

Glu Gly Ser Pro Phe Lys Phe Val Lys Glu Arg Val Asp Glu Val Asp
1               5                   10                  15

Asn Ala Asn Phe Lys Phe Ser Tyr Thr Val Ile Glu Gly Asp Val Leu
            20                  25                  30

Gly Asp Lys Leu Glu Lys Val Ser Leu Glu Leu Lys Ile Val Ala Ala
        35                  40                  45

Pro Gly Gly Gly Ser Ile Leu Lys Ile Ser
    50                  55

<210> SEQ ID NO 109
<211> LENGTH: 58
<212> TYPE: PRT
<213> ORGANISM: Artificial
<220> FEATURE:
<223> OTHER INFORMATION: Carb1.0108 fragment

<400> SEQUENCE: 109

Glu Gly Ser Pro Phe Lys Phe Val Lys Glu Arg Val Asp Glu Val Asp
1               5                   10                  15

Asn Ala Asn Phe Lys Phe Ser Tyr Thr Val Ile Glu Gly Asp Val Leu
            20                  25                  30

Gly Asp Lys Leu Glu Lys Val Ser Leu Glu Leu Thr Ile Val Ala Ala
        35                  40                  45

Pro Gly Gly Gly Ser Ile Leu Lys Ile Ser
    50                  55

<210> SEQ ID NO 110
<211> LENGTH: 58
<212> TYPE: PRT
<213> ORGANISM: Artificial
<220> FEATURE:
<223> OTHER INFORMATION: Cora1/5 fragment

<400> SEQUENCE: 110

Glu Gly Ser Arg Tyr Lys Tyr Val Lys Glu Arg Val Asp Glu Val Asp
1               5                   10                  15

Asn Thr Asn Phe Thr Tyr Ser Tyr Thr Val Ile Glu Gly Asp Val Leu
            20                  25                  30

Gly Asp Lys Leu Glu Lys Val Cys His Glu Leu Lys Ile Val Ala Ala
        35                  40                  45

Pro Gly Gly Gly Ser Ile Leu Lys Ile Ser
    50                  55

<210> SEQ ID NO 111
<211> LENGTH: 58
<212> TYPE: PRT
<213> ORGANISM: Artificial
<220> FEATURE:
<223> OTHER INFORMATION: Cora1/11 fragment

<400> SEQUENCE: 111

Glu Gly Ser Arg Tyr Lys Tyr Val Lys Glu Arg Val Asp Glu Val Asp
1               5                   10                  15

Asn Thr Asn Phe Thr Tyr Ser Tyr Thr Val Ile Glu Gly Asp Val Leu
            20                  25                  30

Gly Asp Lys Leu Glu Lys Val Cys His Glu Leu Lys Ile Val Ala Ala
        35                  40                  45

Pro Gly Gly Gly Ser Ile Leu Lys Ile Ser
    50                  55

<210> SEQ ID NO 112
<211> LENGTH: 58
<212> TYPE: PRT
<213> ORGANISM: Artificial
<220> FEATURE:
<223> OTHER INFORMATION: Cora1/6 fragment

<400> SEQUENCE: 112

Glu Gly Ser Arg Tyr Lys Tyr Val Lys Glu Arg Val Asp Glu Val Asp
1               5                   10                  15

Asn Thr Asn Phe Lys Tyr Ser Tyr Thr Val Ile Glu Gly Asp Val Leu
            20                  25                  30

Gly Asp Lys Leu Glu Lys Val Cys Ser Glu Leu Lys Ile Val Ala Ala
        35                  40                  45

Pro Gly Gly Gly Ser Ile Leu Lys Ile Ser
    50                  55

<210> SEQ ID NO 113
<211> LENGTH: 58
<212> TYPE: PRT
<213> ORGANISM: Artificial
<220> FEATURE:
<223> OTHER INFORMATION: Cora1/16 fragment

<400> SEQUENCE: 113

Glu Gly Ser Arg Tyr Lys Tyr Val Lys Glu Arg Val Asp Glu Val Asp
1               5                   10                  15

Asn Thr Asn Phe Lys Tyr Ser Tyr Thr Val Ile Glu Gly Asp Val Leu
            20                  25                  30

Gly Asp Lys Leu Glu Lys Val Cys Ser Glu Leu Lys Ile Val Ala Ala
        35                  40                  45

Pro Gly Gly Gly Ser Thr Leu Lys Ile Ser
    50                  55

<210> SEQ ID NO 114
<211> LENGTH: 58
<212> TYPE: PRT
<213> ORGANISM: Artificial
<220> FEATURE:
<223> OTHER INFORMATION: Carb1/2or fragment

<400> SEQUENCE: 114

Glu Gly Ser Pro Val Lys Tyr Val Lys Glu Arg Val Glu Glu Ile Asp
1               5                   10                  15

His Thr Asn Phe Lys Tyr Asn Tyr Thr Val Ile Glu Gly Asp Val Leu
            20                  25                  30

Gly Asp Lys Leu Glu Lys Val Ser His Glu Leu Lys Ile Val Ala Ala
        35                  40                  45

Pro Gly Gly Gly Ser Ile Val Lys Ile Ser
    50                  55

<210> SEQ ID NO 115
<211> LENGTH: 58
<212> TYPE: PRT
<213> ORGANISM: Artificial
<220> FEATURE:
<223> OTHER INFORMATION: Carb1.0201 fragment

<400> SEQUENCE: 115

Glu Gly Ser Pro Val Lys Tyr Val Lys Glu Arg Val Glu Glu Ile Asp
1               5                   10                  15

His Thr Asn Phe Lys Tyr Asn Tyr Thr Val Ile Glu Gly Asp Val Leu
            20                  25                  30

Gly Asp Lys Leu Glu Lys Val Ser His Glu Leu Lys Ile Val Ala Ala
            35                  40                  45

Pro Gly Gly Gly Ser Ile Val Lys Ile Ser
    50                  55

<210> SEQ ID NO 116
<211> LENGTH: 58
<212> TYPE: PRT
<213> ORGANISM: Artificial
<220> FEATURE:
<223> OTHER INFORMATION: Glym4.0101 fragment

<400> SEQUENCE: 116

Glu Asp Gly Glu Thr Lys Phe Val Leu His Lys Ile Glu Ser Ile Asp
1               5                   10                  15

Glu Ala Asn Leu Gly Tyr Ser Tyr Ser Val Val Gly Gly Ala Ala Leu
            20                  25                  30

Pro Asp Thr Ala Glu Lys Ile Thr Phe Asp Ser Lys Leu Val Ala Gly
            35                  40                  45

Pro Asn Gly Gly Ser Ala Gly Lys Leu Thr
    50                  55

<210> SEQ ID NO 117
<211> LENGTH: 58
<212> TYPE: PRT
<213> ORGANISM: Artificial
<220> FEATURE:
<223> OTHER INFORMATION: Vigr1.0101 fragment

<400> SEQUENCE: 117

Glu Asp Gly Glu Thr Lys Phe Val Leu His Lys Ile Glu Ser Val Asp
1               5                   10                  15

Glu Ala Asn Leu Gly Tyr Ser Tyr Ser Ile Val Gly Gly Val Ala Leu
            20                  25                  30

Pro Asp Thr Ala Glu Lys Ile Thr Ile Asp Thr Lys Ile Ser Asp Gly
            35                  40                  45

Ala Asp Gly Gly Ser Leu Ile Lys Leu Thr
    50                  55

<210> SEQ ID NO 118
<211> LENGTH: 58
<212> TYPE: PRT
<213> ORGANISM: Artificial
<220> FEATURE:
<223> OTHER INFORMATION: Arah8.0101 fragment

<400> SEQUENCE: 118

Glu Asp Gly Glu Thr Lys Phe Ile Leu His Lys Val Glu Ser Ile Asp
1               5                   10                  15

Glu Ala Asn Tyr Ala Tyr Asn Tyr Ser Val Val Gly Gly Val Ala Leu
            20                  25                  30

Pro Pro Thr Ala Glu Lys Ile Thr Phe Glu Thr Lys Leu Val Glu Gly
            35                  40                  45

Pro Asn Gly Gly Ser Ile Gly Lys Leu Thr
    50                  55

<210> SEQ ID NO 119
<211> LENGTH: 59
<212> TYPE: PRT

<210> SEQ ID NO 120
<211> LENGTH: 160
<212> TYPE: PRT
<213> ORGANISM: Artificial
<220> FEATURE:
<223> OTHER INFORMATION: AspaoPR10 fragment

<400> SEQUENCE: 119

Asn Pro Ala Ile Pro Phe Ser Tyr Val Lys Glu Arg Leu Asp Phe Val
1               5                   10                  15

Asp His Asp Lys Phe Glu Val Lys Gln Thr Leu Val Glu Gly Gly
            20                  25                  30

Leu Gly Lys Met Phe Glu Cys Ala Thr Thr His Phe Lys Phe Glu Pro
        35                  40                  45

Ser Ser Asn Gly Gly Cys Leu Val Lys Val Thr
        50                  55

<210> SEQ ID NO 120
<211> LENGTH: 160
<212> TYPE: PRT
<213> ORGANISM: Castanea sativa

<400> SEQUENCE: 120

Met Gly Val Phe Thr His Glu Asn Glu Ile Thr Ser Ala Ile Pro Pro
1               5                   10                  15

Gly Arg Leu Phe Lys Ala Phe Val Leu Asp Ala Asp Asn Leu Ile Pro
            20                  25                  30

Lys Leu Ala Pro His Ala Ile Lys Ser Ala Glu Ile Ile Glu Gly Asn
        35                  40                  45

Gly Gly Pro Gly Thr Ile Lys Lys Ile Thr Phe Gly Glu Gly Ser Gln
    50                  55                  60

Phe Lys Tyr Val Lys His Arg Ile Asp Glu Ile Asp Gln Ala Asn Phe
65                  70                  75                  80

Thr Tyr Cys Tyr Ser Val Ile Glu Gly Asp Val Val Asn Glu Leu Leu
                85                  90                  95

Glu Lys Ile Ser Tyr Glu Ile Lys Ile Val Ala Ser Pro Asp Gly Gly
            100                 105                 110

Ser Ile Leu Lys Asn Thr Ser Lys Tyr His Thr Lys Gly Glu Gln Glu
        115                 120                 125

Ile Lys Glu Glu Lys Val Met Ala Gly Lys Glu Lys Ala Ala Gly Leu
    130                 135                 140

Phe Lys Ala Val Glu Ala Tyr Leu Leu Ala His Ser Asp Ala Tyr Asn
145                 150                 155                 160

<210> SEQ ID NO 121
<211> LENGTH: 159
<212> TYPE: PRT
<213> ORGANISM: Malus domestica

<400> SEQUENCE: 121

Met Gly Val Phe Thr Tyr Glu Ser Glu Phe Thr Ser Val Ile Pro Pro
1               5                   10                  15

Ala Arg Leu Phe Asn Ala Phe Val Leu Asp Ala Asp Asn Leu Ile Pro
            20                  25                  30

Lys Ile Ala Pro Gln Ala Val Lys Ser Ala Glu Ile Leu Glu Gly Asp
        35                  40                  45

Gly Gly Val Gly Thr Ile Lys Lys Ile Asn Phe Gly Glu Gly Ser Thr
    50                  55                  60

Tyr Ser Tyr Val Lys His Arg Ile Asp Gly Val Asp Lys Asp Asn Phe
65                  70                  75                  80

```
Val Tyr Lys Tyr Ser Val Ile Glu Gly Asp Ala Ile Ser Glu Thr Ile
                85                  90                  95
Glu Lys Ile Ser Tyr Glu Thr Lys Leu Val Ala Gly Ser Gly Ser
            100                 105                 110
Val Ile Lys Ser Thr Ser His Tyr His Thr Lys Gly Asp Val Glu Ile
            115                 120                 125
Lys Glu Glu His Val Lys Ala Gly Lys Glu Lys Ala Ser His Leu Phe
130                 135                 140
Lys Leu Ile Glu Asn Tyr Leu Leu Glu His Gln Asp Ala Tyr Asn
145                 150                 155
```

<210> SEQ ID NO 122
<211> LENGTH: 159
<212> TYPE: PRT
<213> ORGANISM: Malus domestica

<400> SEQUENCE: 122

```
Met Gly Val Phe Thr Tyr Glu Ser Glu Phe Thr Ser Val Ile Pro Pro
1               5                   10                  15
Ala Arg Leu Phe Asn Ala Phe Val Leu Asp Ala Asp Asn Leu Ile Pro
            20                  25                  30
Lys Ile Ala Pro Gln Ala Val Lys Ser Ala Glu Ile Leu Glu Gly Asp
        35                  40                  45
Gly Gly Val Gly Thr Ile Lys Lys Ile Asn Phe Gly Glu Gly Ser Thr
    50                  55                  60
Tyr Ser Tyr Val Lys His Arg Ile Asp Gly Val Asp Lys Glu Asn Phe
65                  70                  75                  80
Val Tyr Lys Tyr Ser Val Ile Glu Gly Asp Ala Ile Ser Glu Thr Ile
                85                  90                  95
Glu Lys Ile Ser Tyr Glu Thr Lys Leu Val Ala Ser Gly Ser Gly Ser
            100                 105                 110
Val Ile Lys Ser Thr Ser His Tyr His Thr Lys Gly Asp Val Glu Ile
            115                 120                 125
Lys Glu Glu His Val Lys Ala Gly Lys Glu Lys Ala Ser His Leu Phe
130                 135                 140
Lys Leu Ile Glu Asn Tyr Leu Leu Glu His Pro Asp Ala Tyr Asn
145                 150                 155
```

<210> SEQ ID NO 123
<211> LENGTH: 159
<212> TYPE: PRT
<213> ORGANISM: Malus domestica

<400> SEQUENCE: 123

```
Met Gly Val Phe Asn Tyr Glu Thr Glu Phe Thr Ser Val Ile Pro Pro
1               5                   10                  15
Ala Arg Leu Phe Asn Ala Phe Val Leu Asp Ala Asp Asn Leu Ile Pro
            20                  25                  30
Lys Ile Ala Pro Gln Ala Val Lys Ser Ala Glu Ile Leu Glu Gly Asp
        35                  40                  45
Gly Gly Val Gly Thr Ile Lys Lys Ile Asn Phe Gly Glu Gly Ser Thr
    50                  55                  60
Tyr Ser Tyr Val Lys His Arg Ile Asp Gly Val Asp Lys Glu Asn Phe
65                  70                  75                  80
Val Tyr Lys Tyr Ser Val Ile Glu Gly Asp Ala Ile Ser Glu Thr Ile
                85                  90                  95
```

```
Glu Lys Ile Ser Tyr Glu Thr Lys Leu Val Ala Ser Gly Ser Gly Ser
            100                 105                 110

Val Ile Lys Ser Thr Ser His Tyr His Thr Lys Ser Asp Val Glu Ile
        115                 120                 125

Lys Glu Glu His Val Lys Ala Gly Lys Glu Lys Ala Ser His Leu Phe
130                 135                 140

Lys Leu Ile Glu Asn Tyr Leu Leu Ala His Ser Asp Ala Tyr Asn
145                 150                 155
```

<210> SEQ ID NO 124
<211> LENGTH: 160
<212> TYPE: PRT
<213> ORGANISM: Malus domestica

<400> SEQUENCE: 124

```
Met Gly Val Phe Asn Tyr Glu Thr Glu Phe Thr Ser Val Ile Pro Ala
1               5                   10                  15

Pro Arg Leu Phe Lys Ala Phe Ile Leu Asp Gly Asp Asn Leu Ile Pro
            20                  25                  30

Lys Ile Ala Pro Gln Ala Ile Lys Ser Thr Lys Ile Ile Glu Gly Asp
        35                  40                  45

Gly Gly Val Gly Thr Ile Lys Lys Val Thr Phe Gly Glu Gly Ser Gln
    50                  55                  60

Tyr Gly Tyr Val Lys Gln Arg Val Asn Gly Ile Asp Lys Asp Asn Phe
65                  70                  75                  80

Thr Tyr Ser Tyr Ser Met Ile Glu Gly Asp Thr Leu Ser Asp Lys Leu
                85                  90                  95

Glu Lys Ile Thr Tyr Glu Thr Lys Leu Ile Ala Ser Pro Asp Gly Gly
            100                 105                 110

Ser Ile Ile Lys Thr Asn Ser His Tyr His Ala Lys Gly Asp Val Glu
        115                 120                 125

Ile Lys Glu Glu His Val Lys Ala Gly Lys Glu Lys Ala Ser Gly Leu
    130                 135                 140

Phe Lys Leu Leu Glu Ala Tyr Leu Leu Ala His Ser Asp Ala Tyr Asn
145                 150                 155                 160
```

<210> SEQ ID NO 125
<211> LENGTH: 160
<212> TYPE: PRT
<213> ORGANISM: Malus domestica

<400> SEQUENCE: 125

```
Met Gly Val Phe Asn Tyr Glu Thr Glu Phe Thr Ser Val Ile Pro Ala
1               5                   10                  15

Pro Arg Leu Phe Lys Ala Phe Ile Leu Asp Gly Asp Asn Leu Ile Pro
            20                  25                  30

Lys Ile Ala Pro Gln Ala Ile Lys Ser Thr Glu Ile Ile Glu Gly Asp
        35                  40                  45

Gly Gly Val Gly Thr Ile Lys Lys Val Thr Phe Gly Glu Gly Ser Gln
    50                  55                  60

Tyr Gly Tyr Val Lys Gln Arg Val Asn Gly Ile Asp Lys Asp Asn Phe
65                  70                  75                  80

Thr Tyr Ser Tyr Ser Met Ile Glu Gly Asp Thr Leu Ser Asp Lys Leu
                85                  90                  95

Glu Lys Ile Thr Tyr Glu Thr Lys Leu Ile Ala Ser Pro Asp Gly Gly
            100                 105                 110
```

```
Ser Ile Ile Lys Thr Thr Ser His Tyr Arg Ala Lys Gly Asp Val Glu
            115                 120                 125

Ile Lys Glu Glu His Val Lys Ala Gly Lys Lys Ala Ser Gly Leu
        130                 135                 140

Phe Lys Leu Leu Glu Ala Tyr Leu Leu Ala His Ser Asp Ala Tyr Asn
145                 150                 155                 160

<210> SEQ ID NO 126
<211> LENGTH: 160
<212> TYPE: PRT
<213> ORGANISM: Malus domestica

<400> SEQUENCE: 126

Met Gly Val Phe Asn Tyr Glu Thr Glu Thr Thr Ser Val Ile Pro Ala
1               5                   10                  15

Pro Arg Leu Phe Lys Ala Phe Ile Leu Asp Gly Asp Asn Leu Ile Pro
            20                  25                  30

Lys Ile Ala Pro Gln Ala Ile Lys Ser Thr Glu Ile Ile Glu Gly Asp
        35                  40                  45

Gly Gly Val Gly Thr Ile Lys Lys Val Thr Phe Gly Glu Gly Ser Gln
    50                  55                  60

Tyr Gly Tyr Val Lys Gln Arg Val Asn Gly Ile Asp Lys Asp Asn Phe
65                  70                  75                  80

Thr Tyr Ser Tyr Ser Met Ile Glu Gly Asp Thr Leu Ser Asp Lys Leu
                85                  90                  95

Glu Lys Ile Thr Tyr Glu Thr Lys Leu Ile Ala Ser Pro Asp Gly Gly
            100                 105                 110

Ser Ile Ile Lys Thr Thr Ser His Tyr His Ala Lys Gly Asp Val Glu
            115                 120                 125

Ile Lys Glu Glu His Val Lys Ala Gly Lys Glu Lys Ala Ser Gly Leu
        130                 135                 140

Phe Lys Leu Leu Glu Ala Tyr Leu Leu Ala His Ser Asp Ala Tyr Asn
145                 150                 155                 160

<210> SEQ ID NO 127
<211> LENGTH: 160
<212> TYPE: PRT
<213> ORGANISM: Prunus armeniaca

<400> SEQUENCE: 127

Met Gly Val Phe Thr Tyr Glu Thr Glu Phe Thr Ser Val Ile Pro Pro
1               5                   10                  15

Glu Lys Leu Phe Lys Ala Phe Ile Leu Asp Ala Asp Asn Leu Ile Pro
            20                  25                  30

Lys Val Ala Pro Thr Ala Val Lys Gly Thr Glu Ile Leu Glu Gly Asp
        35                  40                  45

Gly Gly Val Gly Thr Ile Lys Lys Val Thr Phe Gly Glu Gly Ser Gln
    50                  55                  60

Tyr Ala Tyr Val Lys His Arg Val Asp Gly Ile Asp Lys Asp Asn Leu
65                  70                  75                  80

Ser Tyr Ser Tyr Thr Leu Ile Glu Gly Asp Ala Leu Ser Asp Val Ile
                85                  90                  95

Glu Asn Ile Ala Tyr Asp Ile Lys Leu Val Ala Ser Pro Asp Gly Gly
            100                 105                 110

Ser Ile Val Lys Thr Thr Ser His Tyr His Thr Lys Gly Asp Val Glu
            115                 120                 125
```

```
Ile Lys Glu Glu Gln Val Lys Ala Gly Lys Glu Lys Ala Ala Gly Leu
    130                 135                 140
Phe Lys Leu Val Glu Ala Tyr Leu Leu Ala Asn Pro Asp Ala Tyr Asn
145                 150                 155                 160
```

<210> SEQ ID NO 128
<211> LENGTH: 161
<212> TYPE: PRT
<213> ORGANISM: Corylus avellana

<400> SEQUENCE: 128

```
Met Gly Val Phe Cys Tyr Glu Asp Glu Ala Thr Ser Val Ile Pro Pro
1               5                   10                  15
Ala Arg Leu Phe Lys Ser Phe Val Leu Asp Ala Asp Asn Leu Ile Pro
                20                  25                  30
Lys Val Ala Pro Gln His Phe Thr Ser Ala Glu Asn Leu Glu Gly Asn
            35                  40                  45
Gly Gly Pro Gly Thr Ile Lys Lys Ile Thr Phe Ala Glu Gly Asn Glu
        50                  55                  60
Phe Lys Tyr Met Lys His Lys Val Glu Glu Ile Asp His Ala Asn Phe
65                  70                  75                  80
Lys Tyr Cys Tyr Ser Ile Ile Glu Gly Gly Pro Leu Gly His Thr Leu
                85                  90                  95
Glu Lys Ile Ser Tyr Glu Ile Lys Met Ala Ala Ala Pro His Gly Gly
            100                 105                 110
Gly Ser Ile Leu Lys Ile Thr Ser Lys Tyr His Thr Lys Gly Asn Ala
        115                 120                 125
Ser Ile Asn Glu Glu Glu Ile Lys Ala Gly Lys Glu Lys Ala Ala Gly
    130                 135                 140
Leu Phe Lys Ala Val Glu Ala Tyr Leu Leu Ala His Pro Asp Ala Tyr
145                 150                 155                 160
Cys
```

<210> SEQ ID NO 129
<211> LENGTH: 161
<212> TYPE: PRT
<213> ORGANISM: Corylus avellana

<400> SEQUENCE: 129

```
Met Gly Val Phe Ser Tyr Glu Asp Glu Ala Thr Ser Val Ile Pro Pro
1               5                   10                  15
Ala Arg Leu Phe Lys Ser Phe Val Leu Asp Ala Asp Asn Leu Ile Pro
                20                  25                  30
Lys Val Ala Pro Gln His Phe Thr Ser Ala Glu Asn Leu Glu Gly Asn
            35                  40                  45
Gly Gly Pro Gly Thr Ile Lys Lys Ile Thr Phe Ala Glu Gly Asn Glu
        50                  55                  60
Phe Lys Tyr Met Lys His Lys Val Glu Glu Ile Asp His Ala Asn Phe
65                  70                  75                  80
Lys Tyr Cys Tyr Ser Ile Ile Glu Gly Gly Pro Leu Gly His Thr Leu
                85                  90                  95
Glu Lys Ile Pro Tyr Glu Ile Lys Met Ala Ala Ala Pro His Gly Gly
            100                 105                 110
Gly Ser Ile Leu Lys Ile Thr Ser Lys Tyr His Thr Lys Gly Asn Ala
        115                 120                 125
Ser Ile Asn Glu Glu Glu Ile Lys Ala Gly Lys Glu Lys Ala Ala Gly
    130                 135                 140
```

```
                130                 135                 140
Leu Phe Lys Ala Val Glu Ala Tyr Leu Leu Ala His Pro Asp Ala Tyr
145                 150                 155                 160

Cys

<210> SEQ ID NO 130
<211> LENGTH: 161
<212> TYPE: PRT
<213> ORGANISM: Corylus avellana

<400> SEQUENCE: 130

Met Gly Val Phe Ser Tyr Glu Asp Glu Ala Thr Ser Val Ile Pro Pro
1               5                   10                  15

Ala Arg Leu Phe Lys Ser Phe Val Leu Asp Ala Asp Asn Leu Ile Pro
                20                  25                  30

Lys Val Ala Pro Gln His Phe Thr Gly Ala Glu Asn Leu Glu Gly Asn
            35                  40                  45

Gly Gly Pro Gly Thr Ile Lys Lys Ile Thr Phe Ala Glu Gly Ser Glu
        50                  55                  60

Phe Lys Tyr Met Lys His Lys Val Glu Glu Ile Asp His Ala Asn Phe
65                  70                  75                  80

Lys Tyr Cys Tyr Ser Ile Ile Glu Gly Gly Pro Leu Gly His Thr Leu
                85                  90                  95

Glu Lys Ile Ser Tyr Glu Ile Lys Met Ala Ala Ala Pro His Gly Gly
                100                 105                 110

Gly Ser Ile Leu Lys Ile Thr Ser Lys Tyr His Thr Lys Gly Asn Ala
            115                 120                 125

Ser Ile Ser Glu Glu Glu Ile Lys Ala Gly Lys Glu Lys Ala Ala Gly
        130                 135                 140

Leu Phe Lys Ala Val Glu Ala Tyr Leu Leu Ala His Pro Asp Thr Tyr
145                 150                 155                 160

Cys

<210> SEQ ID NO 131
<211> LENGTH: 161
<212> TYPE: PRT
<213> ORGANISM: Corylus avellana

<400> SEQUENCE: 131

Met Gly Val Phe Cys Tyr Glu Asp Glu Ala Th

Ser Ile Ser Glu Glu Ile Lys Ala Gly Lys Glu Lys Ala Ala Gly
130                 135                 140

Leu Phe Lys Ala Val Glu Ala Tyr Leu Leu Ala His Pro Asp Thr Tyr
145                 150                 155                 160

Cys

<210> SEQ ID NO 132
<211> LENGTH: 160
<212> TYPE: PRT
<213> ORGANISM: Corylus avellana

<400> SEQUENCE: 132

Met Gly Val Phe Asn Tyr Glu Thr Glu Thr Thr Ser Val Ile Pro Pro
1               5                   10                  15

Ala Arg Leu Phe Lys Arg Phe Val Leu Asp Ser Asp Asn Leu Ile Pro
                20                  25                  30

Lys Val Ala Pro Lys Ala Ile Lys Ser Ile Glu Ile Ile Glu Gly Asn
            35                  40                  45

Gly Gly Pro Gly Thr Ile Lys Lys Ile Cys Phe Asp Glu Gly Ser Pro
        50                  55                  60

Phe Asn Tyr Ile Lys Gln Lys Val Glu Glu Ile Asp Gln Ala Asn Phe
65                  70                  75                  80

Ser Tyr Arg Tyr Ser Val Ile Glu Gly Asp Ala Leu Ser Asp Lys Leu
                85                  90                  95

Glu Lys Ile Asn Tyr Glu Ile Lys Ile Val Ala Ser Pro His Gly Gly
                100                 105                 110

Ser Ile Leu Lys Ser Ile Ser Lys Tyr His Thr Ile Gly Asp His Glu
            115                 120                 125

Leu Lys Asp Glu Gln Ile Lys Ala Gly Lys Glu Lys Ala Ser Gly Leu
        130                 135                 140

Phe Lys Ala Val Glu Gly Tyr Leu Leu Ala His Ser Asp Ala Tyr Asn
145                 150                 155                 160

<210> SEQ ID NO 133
<211> LENGTH: 160
<212> TYPE: PRT
<213> ORGANISM: Corylus avellana

<400> SEQUENCE: 133

Met Gly Val Phe Asn Tyr Glu Thr Glu Ser Thr Ser Val Ile Pro Ala
1               5                   10                  15

Ala Arg Leu Phe Lys Ala Phe Ile Leu Asp Gly Asn Asn Leu Ile Pro
                20                  25                  30

Lys Val Ala Pro Gln Ala Val Ser Ser Val Glu Asn Val Glu Gly Asn
            35                  40                  45

Gly Gly Pro Gly Thr Ile Lys Lys Ile Thr Phe Ser Glu Gly Ser Pro
        50                  55                  60

Phe Lys Tyr Val Lys Glu Arg Val Glu Glu Val Asp His Thr Asn Phe
65                  70                  75                  80

Lys Tyr Ser Tyr Thr Val Ile Glu Gly Gly Pro Val Gly Asp Lys Val
                85                  90                  95

Glu Lys Ile Cys Asn Glu Ile Lys Ile Val Ala Ala Pro Asp Gly Gly
                100                 105                 110

Ser Ile Leu Lys Ile Ser Asn Lys Tyr His Thr Lys Gly Asp His Glu
            115                 120                 125

Val Asp Ala Glu His Ile Lys Gly Gly Lys Glu Lys Val Glu Gly Leu

Phe Arg Ala Val Glu Ala Tyr Leu Leu Ala His Ser Asp Ala Tyr Asn
145                 150                 155                 160

<210> SEQ ID NO 134
<211> LENGTH: 160
<212> TYPE: PRT
<213> ORGANISM: Corylus avellana

<400> SEQUENCE: 134

Met Gly Val Phe Asn Tyr Glu Val Glu Thr Pro Ser Val Ile Pro Ala
1               5                   10                  15

Ala Arg Leu Phe Lys Ser Tyr Val Leu Asp Gly Asp Lys Leu Ile Pro
                20                  25                  30

Lys Val Ala Pro Gln Ala Ile Thr Ser Val Glu Asn Val Glu Gly Asn
            35                  40                  45

Gly Gly Pro Gly Thr Ile Lys Asn Ile Thr Phe Gly Glu Gly Ser Arg
        50                  55                  60

Tyr Lys Tyr Val Lys Glu Arg Val Asp Glu Val Asp Asn Thr Asn Phe
65                  70                  75                  80

Thr Tyr Ser Tyr Thr Val Ile Glu Gly Asp Val Leu Gly Asp Lys Leu
                85                  90                  95

Glu Lys Val Cys His Glu Leu Lys Ile Val Ala Ala Pro Gly Gly Gly
            100                 105                 110

Ser Ile Leu Lys Ile Ser Ser Lys Phe His Ala Lys Gly Asp His Glu
        115                 120                 125

Ile Asn Ala Glu Glu Met Lys Gly Ala Lys Glu Met Ala Glu Lys Leu
    130                 135                 140

Leu Arg Ala Val Glu Thr Tyr Leu Leu Ala His Ser Ala Glu Tyr Asn
145                 150                 155                 160

<210> SEQ ID NO 135
<211> LENGTH: 160
<212> TYPE: PRT
<213> ORGANISM: Corylus avellana

<400> SEQUENCE: 135

Met Gly Val Phe Asn Tyr Glu Ala Glu Thr Thr Ser Val Ile Pro Ala
1               5                   10                  15

Ala Arg Leu Phe Lys Ser Tyr Val Leu Asp Gly Asp Lys Leu Ile Pro
20 25 30

Lys Val Ala Pro Gln Ala Ile Thr Ser Val Glu Asn Val Glu Gly Asn
35 40 45

Gly Gly Pro Gly Thr Ile Lys Asn Ile Thr Phe Gly Glu Gly Ser Arg
50 55 60

Tyr Lys Tyr Val Lys Glu Arg Val Asp Glu Val Asp Asn Thr Asn Phe
65 70 75 80

Thr Tyr Ser Tyr Thr Val Ile Glu Gly Asp Val Leu Gly Asp Lys Leu
85 90 95

Glu Lys Val Cys His Glu Leu Lys Ile Val Ala Ala Pro Gly Gly Gly
100 105 110

Ser Ile Leu Lys Ile Ser Ser Lys Phe His Ala Lys Gly Asp His Glu
115 120 125

Ile Asn Ala Glu Glu Ile Lys Gly Ala Lys Glu Met Ala Glu Lys Leu
130 135 140

Leu Arg Ala Val Glu Thr Tyr Leu Leu Ala His Ser Ala Glu Tyr Asn

<210> SEQ ID NO 136
<211> LENGTH: 160
<212> TYPE: PRT
<213> ORGANISM: Corylus avellana

<400> SEQUENCE: 136

Met Gly Val Phe Asn Tyr Glu Val Glu Thr Pro Ser Val Ile Pro Ala
1               5                   10                  15

Ala Arg Leu Phe Lys Ser Tyr Val Leu Asp Gly Asp Lys Leu Ile Pro
            20                  25                  30

Lys Val Ala Pro Gln Ala Ile Thr Ser Val Glu Asn Val Glu Gly Asn
        35                  40                  45

Gly Gly Pro Gly Thr Ile Lys Asn Ile Thr Phe Gly Glu Gly Ser Arg
    50                  55                  60

Tyr Lys Tyr Val Lys Glu Arg Val Asp Glu Val Asp Asn Thr Asn Phe
65                  70                  75                  80

Lys Tyr Ser Tyr Thr Val Ile Glu Gly Asp Val Leu Gly Asp Lys Leu
                85                  90                  95

Glu Lys Val Cys Ser Glu Leu Lys Ile Val Ala Ala Pro Gly Gly Gly
            100                 105                 110

Ser Ile Leu Lys Ile Ser Ser Lys Phe His Ala Lys Gly Asp His Glu
        115                 120                 125

Ile Asn Ala Glu Glu Met Lys Gly Ala Lys Glu Met Ala Glu Lys Leu
    130                 135                 140

Leu Arg Ala Val Glu Thr Tyr Leu Leu Ala His Ser Ala Glu Tyr Asn
145                 150                 155                 160

<210> SEQ ID NO 137
<211> LENGTH: 160
<212> TYPE: PRT
<213> ORGANISM: Corylus avellana

<400> SEQUENCE: 137

Met Gly Val Phe Asn Tyr Glu Val Glu Thr Pro Ser Val Ile Ser Ala
1               5                   10                  15

Ala Arg Leu Phe Lys Ser Tyr Val Leu Asp Gly Asp Lys Leu Ile Pro
            20                  25                  30

Lys Val Ala Pro Gln Ala Ile Thr Ser Val Glu Asn Val Gly Gly Asn
        35                  40                  45

Gly Gly Pro Gly Thr Ile Lys Asn Ile Thr Phe Gly Glu Gly Ser Arg
    50                  55                  60

Tyr Lys Tyr Val Lys Glu Arg Val Asp Glu Val Asp Asn Thr Asn Phe
65                  70                  75                  80

Lys Tyr Ser Tyr Thr Val Ile Glu Gly Asp Val Leu Gly Asp Lys Leu
                85                  90                  95

Glu Lys Val Cys Ser Glu Leu Lys Ile Val Ala Ala Pro Gly Gly Gly
            100                 105                 110

Ser Thr Leu Lys Ile Ser Ser Lys Phe His Ala Lys Gly Asp His Glu
        115                 120                 125

Ile Asn Ala Glu Glu Met Lys Gly Ala Lys Glu Met Ala Glu Lys Leu
    130                 135                 140

Leu Arg Ala Val Glu Thr Tyr Leu Leu Ala His Ser Ala Glu Tyr Asn
145                 150                 155                 160

```
<210> SEQ ID NO 138
<211> LENGTH: 160
<212> TYPE: PRT
<213> ORGANISM: Betula pendula

<400> SEQUENCE: 138

Met Gly Val Phe Asn Tyr Glu Ile Glu Thr Thr Ser Val Ile Pro Ala
1               5                   10                  15

Ala Arg Leu Phe Lys Ala Phe Ile Leu Asp Gly Asp Asn Leu Val Pro
                20                  25                  30

Lys Val Ala Pro Gln Ala Ile Ser Ser Val Glu Asn Ile Glu Gly Asn
            35                  40                  45

Gly Gly Pro Gly Thr Ile Lys Lys Ile Asn Phe Pro Glu Gly Phe Pro
        50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Val Gly Asp Thr Leu
                85                  90                  95

Glu Lys Ile Ser Asn Glu Ile Lys Ile Val Ala Thr Pro Asp Gly Gly
                100                 105                 110

Cys Val Leu Lys Ile Ser Asn Lys Tyr His Thr Lys Gly Asn His Glu
            115                 120                 125

Val Lys Ala Glu Gln Val Lys Ala Ser Lys Glu Met Gly Glu Thr Leu
        130                 135                 140

Leu Arg Ala Val Glu Ser Tyr Leu Leu Ala His Ser Asp Ala Tyr Asn
145                 150                 155                 160

<210> SEQ ID NO 139
<211> LENGTH: 160
<212> TYPE: PRT
<213> ORGANISM: Betula pendula

<400> SEQUENCE: 139

Met Gly Val Phe Asn Tyr Gl

-continued

<213> ORGANISM: Betula pendula

<400> SEQUENCE: 140

Met Gly Val Phe Asn Tyr Glu Ser Glu Thr Thr Ser Val Ile Pro Ala
1               5                   10                  15

Ala Arg Leu Phe Lys Ala Phe Ile Leu Glu Gly Asp Asn Leu Ile Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Asn Phe Pro Glu Gly Phe Pro
    50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Val Gly Asp Thr Leu
                85                  90                  95

Glu Lys Ile Ser Asn Glu Ile Lys Ile Val Ala Thr Pro Asp Gly Gly
            100                 105                 110

Cys Val Leu Lys Ile Ser Asn Lys Tyr His Thr Lys Gly Asn His Glu
        115                 120                 125

Val Lys Ala Glu Gln Val Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160

<210> SEQ ID NO 141
<211> LENGTH: 160
<212> TYPE: PRT
<213> ORGANISM: Betula pendula

<400> SEQUENCE: 141

Met Gly Val Phe Asn Tyr Glu Ile Glu Ala Thr Ser Val Ile Pro Ala
1               5                   10                  15

Ala Arg Leu Phe Lys Ala Phe Ile Leu Asp Gly Asp Asn Leu Phe Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Ser Phe Pro Glu Gly Phe Pro
    50                  55                  60

Phe Lys Tyr Val Lys Asp Arg Val Asp Glu Val Asp His Thr Asn Phe
65                  70                  75                  80

Lys Tyr Ser Tyr Ser Val Ile Glu Gly Gly Pro Val Gly Asp Thr Leu
                85                  90                  95

Glu Lys Ile Ser Asn Glu Ile Lys Ile Val Ala Thr Pro Asn Gly Gly
            100                 105                 110

Ser Ile Leu Lys Ile Asn Asn Lys Tyr His Thr Lys Gly Asp His Glu
        115                 120                 125

Val Lys Ala Glu Gln Ile Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160

<210> SEQ ID NO 142
<211> LENGTH: 160
<212> TYPE: PRT
<213> ORGANISM: Betula pendula

<400> SEQUENCE: 142

```
Met Gly Val Phe Asn Tyr Glu Thr Glu Ala Thr Ser Val Ile Pro Ala
1               5                   10                  15

Ala Arg Leu Phe Lys Ala Phe Ile Leu Asp Gly Asp Asn Leu Phe Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Ser Phe Pro Glu Gly Phe Pro
    50                  55                  60

Phe Lys Tyr Val Lys Asp Arg Val Asp Glu Val Asp His Thr Asn Phe
65                  70                  75                  80

Lys Tyr Ser Tyr Ser Val Ile Glu Gly Gly Pro Val Gly Asp Thr Leu
                85                  90                  95

Glu Lys Ile Ser Asn Glu Ile Lys Ile Val Ala Thr Pro Asn Gly Gly
            100                 105                 110

Ser Ile Leu Lys Ile Asn Asn Lys Tyr His Thr Lys Gly Asp His Glu
        115                 120                 125

Val Lys Ala Glu Gln Ile Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160

<210> SEQ ID NO 143
<211> LENGTH: 160
<212> TYPE: PRT
<213> ORGANISM: Betula pendula

<400> SEQUENCE: 143

Met Gly Val Phe Asn Tyr Glu Thr Glu Ala Thr Ser Val Ile Pro Ala
1               5                   10                  15

Ala Arg Leu Phe Lys Ala Phe Ile Leu Asp Gly Asp Asn Leu Phe Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Ser Phe Pro Glu Gly Ile Pro
    50                  55                  60

Phe Lys Tyr Val Lys Gly Arg Val Asp Glu Val Asp His Thr Asn Phe
65                  70                  75                  80

Lys Tyr Ser Tyr Ser Val Ile Glu Gly Gly Pro Val Gly Asp Thr Leu
                85                  90                  95

Glu Lys Ile Ser Asn Glu Ile Lys Ile Val Ala Thr Pro Asn Gly Gly
            100                 105                 110

Ser Ile Leu Lys Ile Asn Asn Lys Tyr His Thr Lys Gly Asp His Glu
        115                 120                 125

Val Lys Ala Glu Gln Ile Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160

<210> SEQ ID NO 144
<211> LENGTH: 160
<212> TYPE: PRT
<213> ORGANISM: Betula pendula

<400> SEQUENCE: 144

Met Gly Val Phe Asn Tyr Glu Thr Glu Thr Thr Ser Val Ile Pro Ala
1               5                   10                  15
```

```
Ala Arg Leu Phe Lys Ala Phe Ile Leu Glu Gly Asp Thr Leu Ile Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Thr Phe Pro Glu Gly Ser Pro
    50                  55                  60

Phe Lys Tyr Val Lys Glu Arg Val Asp Glu Val Asp His Ala Asn Phe
65                  70                  75                  80

Lys Tyr Ser Tyr Ser Met Ile Glu Gly Ala Leu Gly Asp Thr Leu
                85                  90                  95

Glu Lys Ile Cys Asn Glu Ile Lys Ile Val Ala Thr Pro Asp Gly Gly
                100                 105                 110

Ser Ile Leu Lys Ile Ser Asn Lys Tyr His Thr Lys Gly Asp His Glu
            115                 120                 125

Met Lys Ala Glu His Met Lys Ala Ile Lys Glu Lys Gly Glu Ala Leu
        130                 135                 140

Leu Arg Ala Val Glu Ser Tyr Leu Leu Ala His Ser Asp Ala Tyr Asn
145                 150                 155                 160

<210> SEQ ID NO 145
<211> LENGTH: 160
<212> TYPE: PRT
<213> ORGANISM: Betula pendula

<400> SEQUENCE: 145

Met Gly Val Phe Asn Tyr Glu Ser Glu Thr Thr Ser Val Ile Pro Ala
1               5                   10                  15

Ala Arg Leu Phe Lys Ala Phe Ile Leu Glu Gly Asp Thr Leu Ile Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Thr Phe Pro Glu Gly Ser Pro
    50                  55                  60

Phe Lys Tyr Val Lys Glu Arg Val Asp Glu Val Asp His Ala Asn Phe
65                  70                  75                  80

Lys Tyr Ser Tyr Ser Met Ile Glu Gly Ala Leu Gly Asp Thr Leu
                85                  90                  95

Glu Lys Ile Cys Asn Glu Ile Lys Ile Val Ala Thr Pro Asp Gly Gly
                100                 105                 110

Ser Ile Leu Lys Ile Ser Asn Lys Tyr His Thr Lys Gly Asp Gln Glu
            115                 120                 125

Met Lys Ala Glu His Met Lys Ala Ile Lys Glu Lys Gly Glu Ala Leu
        130                 135                 140

Leu Arg Ala Val Glu Ser Tyr Leu Leu Ala His Ser Asp Ala Tyr Asn
145                 150                 155                 160

<210> SEQ ID NO 146
<211> LENGTH: 160
<212> TYPE: PRT
<213> ORGANISM: Betula pendula

<400> SEQUENCE: 146

Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Phe Pro
            20                  25                  30
```

```
Lys Val Ala Pro Gln Ala Ile Ser Ser Val Glu Asn Ile Glu Gly Asn
            35                  40                  45

Gly Gly Pro Gly Thr Ile Lys Lys Ile Ser Phe Pro Glu Gly Phe Pro
 50                  55                  60

Phe Lys Tyr Val Lys Asp Arg Val Asp Glu Val Asp His Thr Asn Phe
 65                  70                  75                  80

Lys Tyr Asn Tyr Ser Val Ile Glu Gly Gly Pro Ile Gly Asp Thr Leu
                 85                  90                  95

Glu Lys Ile Ser Asn Glu Ile Lys Ile Val Ala Thr Pro Asp Gly Gly
            100                 105                 110

Ser Ile Leu Lys Ile Ser Asn Lys Tyr His Thr Lys Gly Asp His Glu
            115                 120                 125

Val Lys Ala Glu Gln Val Lys Ala Ser Lys Glu Met Gly Glu Thr Leu
        130                 135                 140

Leu Arg Ala Val Glu Ser Tyr Leu Leu Ala His Ser Asp Ala Tyr Asn
145                 150                 155                 160

<210> SEQ ID NO 147
<211> LENGTH: 160
<212> TYPE: PRT
<213> ORGANISM: Betula pendula

<400> SEQUENCE: 147

Met Gly Val Phe Asn Tyr Glu Ser Glu Thr Thr Ser Val Ile Pro Ala
 1               5                  10                  15

Ala Arg Leu Phe Lys Ala Phe Ile Leu Glu Gly Asp Thr Leu Ile Pro
            20                  25                  30

Lys Val Ala Pro Gln Ala Ile Ser Ser Val Glu Asn Ile Glu Gly Asn
            35                  40                  45

Gly Gly Pro Gly Thr Ile Lys Lys Ile Thr Phe Pro Glu Gly Ser Pro
 50                  55                  60

Phe Lys Tyr Val Lys Glu Arg Val Asp Glu Val Asp His Ala Asn Phe
 65                  70                  75                  80

Lys Tyr Ser Tyr Ser Met Ile Glu Gly Gly Ala Leu Gly Asp Thr Leu
                 85                  90                  95

Glu Lys Ile Cys Asn Glu Ile Lys Ile Val Ala Thr Pro Asp Gly Gly
            100                 105                 110

Ser Ile Leu Lys Ile Ser Asn Lys Tyr His Thr Lys Gly Asp His Glu
            115                 120                 125

Met Lys Ala Glu His Met Lys Ala Ile Lys Glu Lys Gly Glu Ala Leu
        130                 135                 140

Leu Arg Ala Val Glu Ser Tyr Leu Leu Ala His Ser Asp Ala Tyr Asn
145                 150                 155                 160

<210> SEQ ID NO 148
<211> LENGTH: 160
<212> TYPE: PRT
<213> ORGANISM: Betula pendula

<400> SEQUENCE: 148

Met Gly Val Phe Asp Tyr Glu Gly Glu Thr Thr

Gly Gly Pro Gly Thr Ile Lys Lys Ile Thr Phe Pro Glu Gly Ser Pro
50                  55                  60

Phe Lys Tyr Val Lys Glu Arg Val Asp Glu Val Asp His Val Asn Phe
65                  70                  75                  80

Lys Tyr Ser Tyr Ser Val Ile Glu Gly Gly Ala Val Gly Asp Thr Leu
                85                  90                  95

Glu Lys Ile Cys Asn Glu Ile Lys Ile Val Pro Ala Pro Gly Gly Gly
                100                 105                 110

Ser Ile Leu Lys Ile Ser Asn Lys Tyr His Thr Lys Gly Asn His Glu
                115                 120                 125

Met Lys Ala Glu Gln Ile Lys Ala Ser Lys Glu Lys Ala Glu Ala Leu
                130                 135                 140

Phe Arg Ala Val Glu Ser Tyr Leu Leu Ala His Ser Asp Ala Tyr Asn
145                 150                 155                 160

<210> SEQ ID NO 149
<211> LENGTH: 159
<212> TYPE: PRT
<213> ORGANISM: Betula pendula

<400> SEQUENCE: 149

Gly Val Phe Asp Tyr Glu Gly Glu Thr Thr Ser Val Ile Pro Ala Ala
1               5                   10                  15

Arg Leu Phe Lys Ala Phe Ile Leu Asp Gly Asp Asn Leu Ile Pro Lys
                20                  25                  30

Val Ala Pro Gln Ala Val Ser Cys Val Glu Asn Ile Glu Gly Asn Gly
                35                  40                  45

Gly Pro Gly Thr Ile Lys Lys Ile Thr Phe Pro Glu Gly Ser Pro Phe
50                  55                  60

Lys Tyr Val Lys Glu Arg Val Asp Glu Val Asp Arg Val Asn Phe Lys
65                  70                  75                  80

Tyr Ser Tyr Ser Val Ile Glu Gly Gly Ala Val Gly Asp Thr Leu Glu
                85                  90                  95

Lys Ile Cys Asn Glu Ile Lys Ile Val Pro Ala Pro Gly Gly Gly Ser
                100                 105                 110

Ile Leu Lys Ile Ser Asn Lys Tyr His Thr Lys Gly Asn His Glu Met
                115                 120                 125

Lys Ala Glu Gln Ile Lys Ala Ser Lys Glu Lys Ala Glu Ala Leu Phe
                130                 135                 140

Arg Ala Val Glu Ser Tyr Leu Leu Ala His Ser Asp Ala Tyr Asn
145                 150                 155

<210> SEQ ID NO 150
<211> LENGTH: 160
<212> TYPE: PRT
<213> ORGANISM: Betula pendula

<400> SEQUENCE: 150

Met Gly Val Phe Asn Tyr Glu Asp Glu Ala Thr Ser Val Ile Ala Pro
1               5                   10                  15

Ala Arg Leu Phe Lys Ser Phe Val Leu Asp Ala Asp Asn Leu Ile Pro
                20                  25                  30

Lys Val Ala Pro Glu Asn Val Ser Ser Ala Glu Asn Ile Glu Gly Asn
                35                  40                  45

Gly Gly Pro Gly Thr Ile Lys Lys Ile Thr Phe Pro Glu Gly Ser His
50                  55                  60

```
Phe Lys Tyr Met Lys His Arg Val Asp Glu Ile Asp His Ala Asn Phe
 65                  70                  75                  80

Lys Tyr Cys Tyr Ser Ile Ile Glu Gly Gly Pro Leu Gly Asp Thr Leu
                 85                  90                  95

Glu Lys Ile Ser Tyr Glu Ile Lys Ile Val Ala Ala Pro Gly Gly Gly
            100                 105                 110

Ser Ile Leu Lys Ile Thr Ser Lys Tyr His Thr Lys Gly Asp Ile Ser
            115                 120                 125

Leu Asn Glu Glu Ile Lys Ala Gly Lys Lys Gly Ala Gly Leu
            130                 135                 140

Phe Lys Ala Val Glu Asn Tyr Leu Val Ala His Pro Asn Ala Tyr Asn
145                 150                 155                 160

<210> SEQ ID NO 151
<211> LENGTH: 160
<212> TYPE: PRT
<213> ORGANISM: Betula pendula

<400> SEQUENCE: 151

Met Gly Val Phe Asn Tyr Glu Ser Glu Thr Thr Ser Val Ile Pro Ala
  1               5                  10                  15

Ala Arg Leu Phe Lys Ala Phe Ile Leu Asp Gly Asp Asn Leu Ile Pro
                 20                  25                  30

Lys Val Ala Pro Gln Ala Ile Ser Val Glu Asn Ile Glu Gly Asn
             35                  40                  45

Gly Gly Pro Gly Thr Ile Lys Lys Ile Thr Phe Pro Glu Gly Ser Pro
 50                  55                  60

Phe Lys Tyr Val Lys Glu Arg Val Asp Glu Val Asp His Ala Asn Phe
 65                  70                  75                  80

Lys Tyr Ser Tyr Ser Met Ile Glu Gly Gly Ala Leu Gly Asp Thr Leu
                 85                  90                  95

Glu Lys Ile Cys Asn Glu Ile Lys Ile Val Ala Thr Pro Asp Gly Gly
            100                 105                 110

Ser Ile Leu Lys Ile Ser Asn Lys Tyr His Thr Lys Gly Asp His Glu
            115                 120                 125

Met Lys Ala Glu His Met Lys Ala Ile Lys Glu Lys Gly Glu Ala Leu
            130                 135                 140

Leu Arg Ala Val Glu Ser Tyr Leu Leu Ala His Ser Asp Ala Tyr Asn
145                 150                 155                 160

<210> SEQ ID NO 152
<211> LENGTH: 160
<212> TYPE: PRT
<213> ORGANISM: Betula pendula

<400

```
Lys Tyr Asn Tyr Ser Val Ile Glu Gly Gly Pro Ile Gly Asp Thr Leu
                85                  90                  95

Glu Lys Ile Ser Asn Glu Ile Lys Ile Val Ala Thr Pro Asp Gly Gly
            100                 105                 110

Ser Ile Leu Lys Ile Ser Asn Lys Tyr His Thr Lys Gly Asp His Glu
        115                 120                 125

Val Lys Ala Glu Gln Val Lys Ala Ser Lys Glu Met Gly Glu Thr Leu
130                 135                 140

Leu Arg Ala Val Glu Ser Tyr Leu Leu Ala His Ser Asp Ala Tyr Asn
145                 150                 155                 160

<210> SEQ ID NO 153
<211> LENGTH: 160
<212> TYPE: PRT
<213> ORGANISM: Betula pendula

<400> SEQUENCE: 153

Met Gly Val Phe Asn Tyr Glu Thr Glu Thr Pro Ser Val Ile Pro Ala
1               5                   10                  15

Ala Arg Leu Phe Lys Ala Phe Ile Leu Asp Gly Asp Lys Leu Leu Pro
            20                  25                  30

Lys Val Ala Pro Glu Ala Val Ser Ser Val Glu Asn Ile Glu Gly Asn
        35                  40                  45

Gly Gly Pro Gly Thr Ile Lys Lys Ile Thr Phe Pro Glu Gly Ser Pro
    50                  55                  60

Phe Lys Tyr Val Lys Glu Arg Val Asp Glu Val Asp Arg Val Asn Phe
65                  70                  75                  80

Lys Tyr Ser Phe Ser Val Ile Glu Gly Gly Ala Val Gly Asp Ala Leu
                85                  90                  95

Glu Lys Val Cys Asn Glu Ile Lys Ile Val Ala Ala Pro Asp Gly Gly
            100                 105                 110

Ser Ile Leu Lys Ile Ser Asn Lys Phe His Thr Lys Gly Asp His Glu
        115                 120                 125

Ile Asn Ala Glu Gln Ile Lys Ile Glu Lys Glu Lys Ala Glu Gly Leu
130                 135                 140

Leu Lys Ala Val Glu Ser Tyr His Leu Ala His Ser Asp Ala Tyr Asn
145                 150                 155                 160

<210> SEQ ID NO 154
<211> LENGTH: 160
<212> TYPE: PRT
<213> ORGANISM: Betula pendula

<400> SEQUENCE: 154

Met Gly Val Phe Asn Tyr Glu Thr Glu Ala Thr Ser Val Ile Pro Ala
1               5                   10                  15

Ala Arg Le

```
Glu Lys Ile Ser Asn Glu Ile Lys Ile Val Ala Thr Pro Asp Gly Gly
            100                 105                 110

Ser Ile Leu Lys Ile Ser Asn Lys Tyr His Thr Lys Gly Asp His Glu
            115                 120                 125

Val Lys Ala Glu Gln Ile Lys Ala Ser Lys Glu Met Gly Glu Thr Leu
    130                 135                 140

Leu Arg Ala Val Glu Arg Tyr Leu Leu Ala His Ser Asp Ala Tyr Asn
145                 150                 155                 160

<210> SEQ ID NO 155
<211> LENGTH: 160
<212> TYPE: PRT
<213> ORGANISM: Betula pendula

<400> SEQUENCE: 155

Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Ile Pro
                20                  25                  30

Lys Val Ala Pro Gln Ala Ile Ser Ser Val Glu Asn Ile Glu Gly Asn
            35                  40                  45

Gly Gly Pro Gly Thr Ile Lys Lys Ile Thr Phe Pro Glu Gly Ser Pro
    50                  55                  60

Phe Lys Tyr Val Lys Glu Arg Val Asp Glu Val Asp His Ala Asn Phe
65                  70                  75                  80

Lys Tyr Ser Tyr Ser Met Ile Glu Gly Gly Ala Leu Gly Asp Thr Leu
                85                  90                  95

Glu Lys Ile Cys Asn Glu Ile Lys Leu Val Ala Thr Pro Asp Gly Gly
            100                 105                 110

Ser Ile Leu Lys Ile Ser Asn Lys Tyr His Thr Lys Gly Asp His Glu
            115                 120                 125

Met Lys Ala Glu His Met Lys Ala Ile Lys Glu Lys Ala Glu Ala Leu
    130                 135                 140

Leu Arg Ala Val Glu Ser Tyr Leu Leu Ala His Ser Asp Ala Tyr Asn
145                 150                 155                 160

<210> SEQ ID NO 156
<211> LENGTH: 160
<212> TYPE: PRT
<213> ORGANISM: Betula pendula

<400> SEQUENCE: 156

Met Gly Val Phe Asn Tyr Glu Thr Glu Thr Thr Ser Val Ile Pro Ala
1               5                   10                  15

Ala Arg Leu Phe Lys Ala Phe Ile

Ser Ile Leu Lys Ile Ser Asn Lys Tyr His Thr Lys Gly Asp His Glu
        115                 120                 125

Met Lys Ala Glu His Met Lys Ala Ile Lys Glu Lys Gly Glu Ala Leu
    130                 135                 140

Leu Arg Ala Val Glu Ser Tyr Leu Leu Ala His Ser Asp Ala Tyr Asn
145                 150                 155                 160

<210> SEQ ID NO 157
<211> LENGTH: 160
<212> TYPE: PRT
<213> ORGANISM: Betula pendula

<400> SEQUENCE: 157

Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Ile Pro
                20                  25                  30

Lys Val Ala Pro Gln Ala Ile Ser Ser Val Glu Asn Ile Glu Gly Asn
            35                  40                  45

Gly Gly Pro Gly Thr Ile Lys Lys Ile Thr Phe Pro Glu Gly Ser Pro
        50                  55                  60

Phe Lys Tyr Val Lys Glu Arg Val Asp Glu Val Asp His Ala Asn Phe
65                  70                  75                  80

Lys Tyr Ser Tyr Ser Met Ile Glu Gly Gly Ala Leu Gly Asp Thr Leu
                85                  90                  95

Glu Lys Ile Cys Asn Glu Ile Lys Ile Val Ala Thr Pro Asp Gly Gly
            100                 105                 110

Ser Ile Leu Lys Ile Ser Asn Lys Tyr His Thr Lys Gly Asp His Glu
        115                 120                 125

Met Lys Ala Glu His Met Lys Ala Ile Lys Glu Lys Gly Glu Ala Leu
    130                 135                 140

Leu Arg Ala Val Glu Ser Tyr Leu Leu Ala His Ser Asp Ala Tyr Asn
145                 150                 155                 160

<210> SEQ ID NO 158
<211> LENGTH: 160
<212> TYPE: PRT
<213> ORGANISM: Betula pendula

<400> SEQUENCE: 158

Met Gly Val Phe Asn Tyr Glu Thr Ala Thr Ser Val Ile Pro Ala
1               5                   10                  15

Ala Arg Leu Phe Lys Ala Ser Ile Leu Asp Gly Asp Asn Leu Phe Pro
                20                  25                  30

Lys Val Ala Pro Gln Ala Ile Ser Ser Val Glu Asn Ile Glu Gly Asn
            35                  40                  45

Gly Gly Pro Gly Thr Ile Lys Lys Ile Ser Phe Pro Glu Gly Ser Pro
        50                  55                  60

Phe Lys Tyr Val Lys Glu Arg Val Asp Glu Val Asp Arg Val Asn Phe
65                  70                  75                  80

Lys Tyr Ser Phe Ser Val Ile Glu Gly Gly Ala Val Gly Asp Ala Leu
                85                  90                  95

Glu Lys Val Cys Asn Glu Ile Lys Ile Val Ala Ala Pro Asp Gly Gly
            100                 105                 110

Ser Ile Leu Lys Ile Ser Asn Lys Phe His Thr Lys Gly Asp His Glu
        115                 120                 125

Ile Asn Ala Glu Gln Ile Lys Ile Glu Lys Glu Lys Ala Val Gly Leu
    130                     135                   140

Leu Lys Ala Val Glu Ser Tyr Leu Leu Ala His Ser Asp Ala Tyr Asn
145                   150                   155                   160

<210> SEQ ID NO 159
<211> LENGTH: 160
<212> TYPE: PRT
<213> ORGANISM: Betula pendula

<400> SEQUENCE: 159

Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Phe Pro
            20                   25                   30

Lys Val Ala Pro Gln Ala Ile Ser Ser Val Glu Asn Ile Glu Gly Asn
        35                 40                   45

Gly Gly Pro Gly Thr Ile Lys Lys Ile Ser Phe Pro Glu Gly Phe Pro
     50                   55                   60

Phe Lys Tyr Val Lys Asp Arg Val Asp Glu Val Ala His Lys Asn Phe
65                 70                   75                   80

Lys Tyr Ser Tyr Ser Val Ile Glu Gly Gly Pro Ile Gly Asp Thr Leu
            85                   90                   95

Glu Lys Ile Ser Asn Glu Ile Lys Ile Val Ala Thr Pro Asp Gly Arg
              100                105               110

Ser Ile Leu Lys Ile Ser Asn Lys Tyr His Thr Lys Gly Asp His Glu
        115                120                125

Val Lys Ala Glu Gln Ile Lys Ala Ser Lys Glu Met Gly Glu Thr Leu
            130                  135               140

Leu Arg Ala Val Glu Ser Tyr Leu Leu Ala His Ser Asp Ala Tyr Asn
145                   150                   155                   160

<210> SEQ ID NO 160
<211> LENGTH: 160
<212> TYPE: PRT
<213> ORGANISM: Betula pendula

<400> SEQUENCE: 160

Met Gly Val Phe Asn Tyr Glu Thr Glu Thr Thr Ser Val Ile Pro Ala
1               5                   10                  15

Ala Arg Leu Phe Lys Ala Phe Phe Leu Asp Gly Asp Asn Leu Phe Pro
            20                   25                   30

Lys Val Ala Pro Gln Ala Ile Ser Ser Val Glu Asn Ile Glu Gly Asn
        35                 40                   45

Gly Gly Pro Gly Thr Ile Lys Lys Ile Ser Phe Pro Glu Gly Phe Pro
     50                   55                   60

Phe Arg Tyr Val Lys Asp Arg Val Asp Glu Val Asp His Thr Asn Phe
65                 70                   75                   80

Lys Tyr Ser Tyr Ser Val Ile Glu Gly Gly Pro Val Gly Asp Thr Leu
            85                   90                   95

Glu Lys Ile Ser Asn Glu Ile Lys Ile Val Ala Thr Pro Asp Gly Gly
              100                105               110

Ser Ile Leu Lys Ile Ser Asn Lys Tyr His Thr Lys Gly Asp His Glu
        115                120                125

Val Lys Glu Glu Gln Ile Lys Ala Ser Lys Glu Met Gly Glu Thr Leu
            130                  135               140

Leu Arg Ala Val Glu Ser Tyr Leu Leu Ala His Ser Asp Ala Tyr Asn
145                 150                 155                 160

<210> SEQ ID NO 161
<211> LENGTH: 160
<212> TYPE: PRT
<213> ORGANISM: Betula pendula

<400> SEQUENCE: 161

Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Phe Pro
                20                  25                  30

Lys Val Ala Pro Gln Ala Ile Ser Ser Val Glu Asn Ile Glu Gly Asn
            35                  40                  45

Gly Gly Pro Gly Thr Ile Lys Lys Ile Ser Phe Pro Glu Gly Phe Pro
        50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Val Gly Asp Thr Leu
                85                  90                  95

Glu Lys Ile Ser Asn Glu Ile Lys Ile Val Ala Thr Pro Asp Gly Gly
            100                 105                 110

Cys Val Leu Lys Ile Ser Asn Lys Tyr His Thr Lys Gly Asn His Glu
        115                 120                 125

Val Lys Ala Glu Gln Val Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160

<210> SEQ ID NO 162
<211> LENGTH: 160
<212> TYPE: PRT
<213> ORGANISM: Betula pendula

<400> SEQUENCE: 162

Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Phe Pro
                20                  25                  30

Lys Val Ala Pro Gln Ala Ile Ser Ser Val Glu Asn Ile Glu Gly Asn
            35                  40                  45

Gly Gly Pro Gly Thr Ile Lys Lys Ile Ser Phe Pro Glu Gly Phe Pro
        50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Val Gly Asp Thr Leu
                85                  90                  95

Glu Lys Ile Ser Asn Glu Ile Lys Ile Val Ala Thr Pro Asp Gly Gly
            100                 105                 110

Ser Ile Leu Lys Ile Ser Asn Lys Tyr His Thr Lys Gly Asp His Glu
        115                 120                 125

Val Lys Ala Glu Gln Val Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160

<210> SEQ ID NO 163
<211> LENGTH: 160
<212> TYPE: PRT
<213> ORGANISM: Betula pendula

<400> SEQUENCE: 163

Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Phe Pro
                20                  25                  30

Lys Val Ala Pro Gln Ala Ile Ser Ser Val Glu Asn Ile Glu Gly Asn
            35                  40                  45

Gly Gly Pro Gly Thr Ile Lys Lys Ile Ser Phe Pro Glu Gly Phe Pro
        50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Ile Gly Asp Ile Leu
                85                  90                  95

Glu Lys Ile Ser Asn Glu Ile Lys Ile Val Ala Thr Pro Asp Gly Gly
            100                 105                 110

Cys Val Leu Lys Ile Ser Asn Lys Tyr His Thr Lys Gly Asn His Glu
        115                 120                 125

Val Lys Ala Glu Gln Val Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160

<210> SEQ ID NO 164
<211> LENGTH: 160
<212> TYPE: PRT
<213> ORGANISM: Betula pendula

<400> SEQUENCE: 164

Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Phe Pro
                20                  25                  30

Lys Val Ala Pro Gln Ala Ile Ser Ser Val Glu Asn Ile Glu Gly Asn
            35                  40                  45

Gly Gly Pro Gly Thr Ile Lys Lys Ile Ser Phe Pro Gly Gly Leu Pro
        50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Ile Gly Asp Thr Leu
                85                  90                  95

Glu Lys Ile Ser Asn Glu Ile Lys Ile Val Ala Thr Pro Asp Gly Gly
            100                 105                 110

Cys Val Leu Lys Ile Ser Asn Lys Tyr His Thr Lys Gly Asn His Glu
        115                 120                 125

Val Lys Ala Glu Gln Val Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160

<210> SEQ ID NO 165

```
<211> LENGTH: 160
<212> TYPE: PRT
<213> ORGANISM: Betula pendula

<400> SEQUENCE: 165

Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Val Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Ser Phe Pro Glu Gly Phe Pro
50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Met Gly Asp Thr Leu
                85                  90                  95

Glu Lys Ile Ser Asn Glu Ile Lys Ile Val Ala Thr Pro Asp Gly Gly
            100                 105                 110

Ser Ile Leu Lys Ile Ser Asn Lys Tyr His Thr Lys Gly Asp His Glu
        115                 120                 125

Val Lys Ala Glu Gln Val Lys Ala Ser Lys Glu Met Gly Glu Thr Leu
130                 135                 140

Leu Arg Ala Val Glu Ser Tyr Leu Leu Ala His Ser Asp Ala Tyr Asn
145                 150                 155                 160

<210> SEQ ID NO 166
<211> LENGTH: 160
<212> TYPE: PRT
<213> ORGANISM: Betula pendula

<400> SEQUENCE: 166

Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Phe Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Ser Phe Pro Glu Gly Phe Pro
50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Ile Gly Asp Thr Leu
                85                  90                  95

Glu Lys Ile Ser Asn Glu Ile Lys Ile Val Ala Thr Pro Asp Gly Gly
            100                 105                 110

Ser Ile Leu Lys Ile Ser Asn Lys Tyr His Thr Lys Gly Asp His Glu
        115                 120                 125

Val Lys Ala Glu Gln Val Lys Ala Ser Lys Glu Met Arg Glu Thr Leu
130                 135                 140

Leu Arg Ala Val Glu Ser Tyr Leu Leu Ala His Ser Asp Ala Tyr Asn
145                 150                 155                 160

<210> SEQ ID NO 167
<211> LENGTH: 160
<212> TYPE: PRT
<213> ORGANISM: Alnus glutinosa
```

```
<400> SEQUENCE: 167

Met Gly Val Phe Asn Tyr Glu Ala Glu Thr Pro Ser Val Ile Pro Ala
1               5                   10                  15

Ala Arg Leu Phe Lys Ala Phe Ile Leu Asp Gly Asp Lys Leu Leu Pro
            20                  25                  30

Lys Val Ala Pro Glu Ala Val Ser Ser Val Glu Asn Ile Glu Gly Asn
        35                  40                  45

Gly Gly Pro Gly Thr Ile Lys Lys Ile Thr Phe Pro Glu Gly Ser Pro
    50                  55                  60

Phe Lys Tyr Val Lys Glu Arg Val Asp Glu Val Asp Arg Val Asn Phe
65                  70                  75                  80

Lys Tyr Ser Phe Ser Val Ile Glu Gly Gly Ala Val Gly Asp Ala Leu
                85                  90                  95

Glu Lys Val Cys Asn Glu Ile Lys Ile Val Ala Ala Pro Asp Gly Gly
            100                 105                 110

Ser Ile Leu Lys Ile Ser Asn Lys Phe His Thr Lys Gly Asp His Glu
        115                 120                 125

Ile Asn Ala Glu Gln Ile Lys Ile Glu Lys Lys Ala Val Gly Leu
130                 135                 140

Leu Lys Ala Val Glu Ser Tyr Leu Leu Ala His Ser Asp Ala Tyr Asn
145                 150                 155                 160

<210> SEQ ID NO 168
<211> LENGTH: 161
<212> TYPE: PRT
<213> ORGANISM: Carpinus betulus

<400> SEQUENCE: 168

Met Gly Val Phe Asn Tyr Glu Ala Glu Thr Thr Ser Val Ile Pro Ala
1               5                   10                  15

Ala Arg Leu Phe Lys Ala Phe Ile Leu Asp Gly Asn Lys Leu Ile Pro
            20                  25                  30

Lys Val Ser Pro Gln Ala Val Ser Ser Val Glu Asn Val Glu Gly Asn
        35                  40                  45

Gly Gly Pro Gly Thr Ile Lys Lys Ile Thr Phe Ser Glu Gly Ser Pro
    50                  55                  60

Val Lys Tyr Val Lys Glu Arg Val Glu Glu Val Asp His Thr Asn Phe
65                  70                  75                  80

Lys Tyr Ser Tyr Thr Val Ile Glu Gly Gly Phe Val Gly Asp Lys Val
                85                  90                  95

Glu Lys Ile Cys Asn Glu Ile Lys Ile Val Ala Ala Pro Asp Gly Gly
            100                 105                 110

Ser Ile Leu Lys Ile Thr Ser Lys Tyr His Thr Lys Gly Asp His Glu
        115                 120                 125

Val Pro Ala Glu His Ile Lys Gly Gly Lys Glu Arg Val Glu Gly Leu
130                 135                 140

Leu Lys Pro Val Glu Ala Tyr Leu Leu Ala His Thr Ala Glu Tyr Asn
145                 150                 155                 160

Asn

<210> SEQ ID NO 169
<211> LENGTH: 161
<212> TYPE: PRT
<213> ORGANISM: Carpinus betulus
```

-continued

<400> SEQUENCE: 169

Met Gly Val Phe Asn Tyr Glu Ala Glu Thr Thr Ser Val Ile Pro Ala
1               5                   10                  15

Ala Arg Leu Phe Lys Ala Phe Ile Leu Asp Gly Asn Asn Leu Ile Pro
            20                  25                  30

Lys Val Ala Pro Gln Ala Val Ser Val Glu Asn Val Glu Gly Asn
        35                  40                  45

Gly Gly Pro Gly Thr Ile Lys Lys Ile Thr Phe Ser Glu Gly Ser Pro
    50                  55                  60

Val Lys Tyr Val Lys Glu Arg Val Glu Val Asp His Thr Asn Phe
65                  70                  75                  80

Lys Tyr Ser Tyr Thr Val Ile Glu Gly Gly Pro Val Gly Asp Lys Val
                85                  90                  95

Glu Lys Ile Cys Asn Glu Ile Lys Ile Val Ala Ala Pro Asp Gly Gly
            100                 105                 110

Ser Ile Leu Lys Ile Thr Ser Lys Tyr His Thr Lys Gly Asp His Glu
        115                 120                 125

Val Pro Ala Glu His Ile Lys Gly Gly Lys Glu Arg Val Glu Gly Leu
    130                 135                 140

Leu Lys Pro Val Glu Ala Tyr Leu Leu Ala His Thr Ala Glu Tyr Asn
145                 150                 155                 160

Asn

<210> SEQ ID NO 170
<211> LENGTH: 160
<212> TYPE: PRT
<213> ORGANISM: Carpinus betulus

<400> SEQUENCE: 170

Met Gly Val Phe Asn Tyr Glu Ala Glu Thr Pro Ser Val Ile Pro Ala
1               5                   10                  15

Ala Arg Leu Phe Lys Ser Tyr Val Leu Asp Gly Asp Lys Leu Ile Pro
            20                  25                  30

Lys Val Ala Pro Gln Ala Ile Ser Ser Val Glu Asn Val Gly Gly Asn
        35                  40                  45

Gly Gly Pro Gly Thr Ile Lys Asn Ile Thr Phe Ala Glu Gly Ser Pro
    50                  55                  60

Phe Lys Phe Val Lys Glu Arg Val Asp Glu Val Asp Asn Ala Asn Phe
65                  70                  75                  80

Lys Tyr Asn Tyr Thr Val Ile Glu Gly Asp Val Leu Gly Asp Lys Leu
                85                  90                  95

Glu Lys Val Ser His Glu Leu Lys Ile Val Ala Ala Pro Gly Gly Gly
            100                 105                 110

Ser Ile Val Lys Ile Ser Ser Lys Phe His Ala Lys Gly Asp His Glu
        115                 120                 125

Val Asn Ala Glu Lys Met Lys Gly Ala Lys Glu Met Ala Glu Lys Leu
    130                 135                 140

Leu Arg Ala Val Glu Ser Tyr Leu Leu Ala His Thr Asp Glu Tyr Asn
145                 150                 155                 160

<210> SEQ ID NO 171
<211> LENGTH: 160
<212> TYPE: PRT
<213> ORGANISM: Carpinus betulus

<400> SEQUENCE: 171

-continued

```
Met Gly Val Phe Asn Tyr Glu Ala Glu Thr Pro Ser Val Ile Pro Ala
1               5                   10                  15

Ala Arg Leu Phe Lys Ser Tyr Val Leu Asp Phe Asp Lys Leu Ile Pro
            20                  25                  30

Lys Val Ala Pro Gln Ala Ile Ser Ser Val Glu Asn Val Gly Gly Asn
        35                  40                  45

Gly Gly Pro Gly Thr Ile Lys Asn Ile Thr Phe Ala Glu Gly Ser Pro
    50                  55                  60

Phe Lys Phe Val Lys Glu Arg Val Asp Glu Val Asp Asn Ala Asn Phe
65                  70                  75                  80

Lys Tyr Asn Tyr Thr Val Ile Glu Gly Asp Val Leu Gly Asp Lys Leu
                85                  90                  95

Glu Lys Val Ser His Glu Leu Lys Ile Val Ala Ala Pro Gly Gly Gly
            100                 105                 110

Ser Ile Val Lys Ile Ser Ser Lys Phe His Ala Lys Gly Asp His Glu
        115                 120                 125

Val Asn Ala Glu Lys Met Lys Gly Ala Lys Glu Met Ala Glu Lys Leu
    130                 135                 140

Leu Arg Ala Val Glu Ser Tyr Leu Leu Ala His Thr Asp Glu Tyr Asn
145                 150                 155                 160

<210> SEQ ID NO 172
<211> LENGTH: 160
<212> TYPE: PRT
<213> ORGANISM: Carpinus betulus

<400> SEQUENCE: 172

Met Gly Val Phe Asn Tyr Glu Ala Glu Thr Pro Ser Val Ile Pro Ala
1               5                   10                  15

Ala Arg Leu Phe Lys Ser Tyr Val Leu Asp Gly Asp Lys Leu Ile Pro
            20                  25                  30

Lys Val Ala Pro Gln Ala Ile Ser Ser Val Glu Asn Val Gly Gly Asn
        35                  40                  45

Gly Gly Pro Gly Thr Ile Lys Asn Ile Thr Phe Ala Glu Gly Ser Pro
    50                  55                  60

Phe Lys Phe Val Lys Glu Arg Val Asp Glu Val Asp Asn Ala Asn Phe
65                  70                  75                  80

Lys Tyr Asn Tyr Thr Val Ile Glu Gly Asp Val Leu Gly Asp Asn Leu
                85                  90                  95

Glu Lys Val Ser His Glu Leu Lys Ile Val Ala Ala Pro Gly Gly Gly
            100                 105                 110

Ser Ile Val Lys Ile Ser Ser Lys Phe His Ala Lys Gly Asp His Glu
        115                 120                 125

Val Asn Ala Glu Glu Met Lys Gly Ala Lys Glu Met Ala Glu Lys Leu
    130                 135                 140

Leu Arg Ala Val Glu Ser Tyr Leu Leu Ala His Thr Asp Glu Tyr Asn
145                 150                 155                 160

<210> SEQ ID NO 173
<211> LENGTH: 159
<212> TYPE: PRT
<213> ORGANISM: Carpinus betulus

<400> SEQUENCE: 173

Gly Val Phe Asn Tyr Glu Ala Glu Thr Pro Ser Val Ile Pro Ala Ala
1               5                   10                  15
```

```
Arg Leu Phe Lys Ser Tyr Val Leu Asp Gly Asp Lys Leu Ile Pro Lys
             20                  25                  30

Val Ala Pro Gln Val Ile Ser Ser Val Glu Asn Val Gly Gly Asn Gly
         35                  40                  45

Gly Pro Gly Thr Ile Lys Asn Ile Thr Phe Ala Glu Gly Ile Pro Phe
     50                  55                  60

Lys Phe Val Lys Glu Arg Val Asp Glu Val Asp Asn Ala Asn Phe Lys
65                  70                  75                  80

Tyr Asn Tyr Thr Val Ile Glu Gly Asp Val Leu Gly Asp Lys Leu Glu
                 85                  90                  95

Lys Val Ser His Glu Leu Lys Ile Val Ala Ala Pro Gly Gly Gly Ser
             100                 105                 110

Ile Val Lys Ile Ser Ser Lys Phe His Ala Lys Gly Tyr His Glu Val
         115                 120                 125

Asn Ala Glu Lys Met Lys Gly Ala Lys Glu Met Ala Glu Lys Leu Leu
     130                 135                 140

Arg Ala Val Glu Ser Tyr Leu Leu Ala His Thr Ala Glu Tyr Asn
145                 150                 155

<210> SEQ ID NO 174
<211> LENGTH: 159
<212> TYPE: PRT
<213> ORGANISM: Carpinus betulus

<400> SEQUENCE: 174

Gly Val Phe Asn Tyr Glu Ala Glu Thr Pro Ser Val Ile Pro Ala Ala
1               5                   10                  15

Arg Leu Phe Lys Ser Tyr Val Leu Asp Gly Asp Lys Leu Ile Pro Lys
             20                  25                  30

Val Ala Pro Gln Ala Ile Ser Ser Val Glu Asn Val Gly Gly Asn Gly
         35                  40                  45

Gly Pro Gly Thr Ile Lys Asn Ile Thr Phe Ala Glu Gly Ser Pro Phe
     50                  55                  60

Lys Phe Val Lys Glu Arg Val Asp Glu Val Asp Asn Ala Asn Phe Lys
65                  70                  75                  80

Tyr Asn Tyr Thr Val Ile Glu Gly Asp Val Leu Gly Asp Lys Leu Glu
                 85                  90                  95

Lys Val Ser His Glu Leu Lys Ile Val Ala Ala Pro Gly Gly Gly Ser
             100                 105                 110

Ile Val Lys Ile Ser Ser Lys Phe His Ala Lys Gly Tyr His Glu Val
         115                 120                 125

Asn Ala Glu Glu Met Lys Gly Ala Lys Glu Met Ala Glu Lys Leu Leu
     130                 135                 140

Arg Ala Val Glu Ser Tyr Leu Leu Ala His Thr Ala Glu Tyr Asn
145                 150                 155

<210> SEQ ID NO 175
<211> LENGTH: 160
<212> TYPE: PRT
<213> ORGANISM: Carpinus betulus

<400> SEQUENCE: 175

Met Gly Val Phe Asn Tyr Glu Ala Glu Thr Pro Ser Val Ile Pro Ala
1               5                   10                  15

Ala Arg Leu Phe Lys Ser Tyr Val Leu Asp Phe Asp Lys Leu Ile Pro
             20                  25                  30
```

```
Lys Val Ala Pro Gln Ala Ile Ser Ser Val Glu Asn Val Gly Gly Asn
            35                  40                  45

Gly Gly Pro Gly Thr Ile Lys Asn Ile Thr Phe Ala Glu Gly Ser Pro
        50                  55                  60

Phe Lys Phe Val Lys Glu Arg Val Asp Glu Val Asp Asn Ala Asn Phe
 65                 70                  75                  80

Lys Tyr Asn Tyr Thr Val Ile Glu Gly Asp Val Leu Gly Asp Lys Leu
                85                  90                  95

Glu Lys Val Ser His Glu Leu Lys Ile Val Ala Ala Pro Gly Gly Gly
            100                 105                 110

Ser Ile Val Lys Ile Ser Ser Lys Phe His Ala Lys Gly Asp His Glu
        115                 120                 125

Val Asn Ala Glu Glu Met Lys Gly Ala Lys Glu Met Ala Glu Lys Leu
    130                 135                 140

Leu Arg Ala Val Glu Ser Tyr Leu Leu Ala His Thr Ala Glu Tyr Asn
145                 150                 155                 160

<210> SEQ ID NO 176
<211> LENGTH: 160
<212> TYPE: PRT
<213> ORGANISM: Carpinus betulus

<400> SEQUENCE: 176

Met Gly Val Phe Asn Tyr Glu Ala Glu Thr Pro Ser Val Ile Pro Ala
 1               5                  10                  15

Ala Arg Leu Phe Lys Ser Tyr Val Leu Asp Phe Asp Lys Leu Ile Pro
            20                  25                  30

Lys Val Ala Pro Gln Ala Ile Ser Ser Val Glu Asn Val Gly Gly Asn
            35                  40                  45

Gly Gly Pro Gly Thr Ile Lys Asn Ile Thr Phe Ala Glu Gly Ser Pro
        50                  55                  60

Phe Lys Phe Val Lys Glu Arg Val Asp Glu Val Asp Asn Ala Asn Phe
 65                 70                  75                  80

Lys Tyr Asn Tyr Thr Val Ile Glu Gly Asp Val Leu Gly Asp Lys Leu
                85                  90                  95

Glu Lys Val Ser His Glu Leu Lys Ile Val Ala Ala Pro Gly Gly Gly
            100                 105                 110

Ser Ile Val Lys Ile Ser Ser Lys Phe His Ala Lys Gly Asp His Glu
        115                 120                 125

Val Asn Ala Glu Glu Met Lys Gly Ala Lys Glu Met Ala Glu Lys Leu
    130                 135                 140

Leu Arg Ala Val Glu Ser Tyr Leu Leu Ala His Thr Ala Glu Tyr Asn
145                 150                 155                 160

<210> SEQ ID NO 177
<211> LENGTH: 160
<212> TYPE: PRT
<213> ORGANISM: Carpinus betulus

<400> SEQUENCE: 177

Met Gly Val Phe Asn Tyr Glu Ala Glu Thr Pro Ser Val Ile Pro Ala
 1               5                  10                  15

Ala Arg Leu Phe Lys Ser Tyr Val Leu Asp Phe Asp Lys Leu Ile Pro
            20                  25                  30

Lys Val Ala Pro Gln Ala Ile Ser Ser Val Glu Asn Val Gly Gly Asn
            35                  40                  45
```

```
Gly Gly Pro Gly Thr Ile Lys Asn Ile Thr Phe Ala Glu Gly Ser Pro
 50                  55                  60

Phe Lys Phe Val Lys Glu Arg Val Asp Glu Val Asp Asn Ala Asn Phe
 65                  70                  75                  80

Lys Tyr Asn Tyr Thr Val Ile Glu Gly Asp Val Leu Gly Asp Lys Leu
                 85                  90                  95

Glu Lys Val Ser His Glu Leu Lys Ile Val Ala Ala Pro Gly Gly Gly
                100                 105                 110

Ser Ile Val Lys Ile Ser Ser Lys Phe His Ala Lys Gly Asp His Glu
                115                 120                 125

Val Asn Ala Glu Glu Met Lys Gly Ala Lys Glu Met Ala Glu Lys Leu
                130                 135                 140

Leu Arg Ala Val Glu Ser Tyr Leu Leu Ala His Thr Ala Glu Tyr Asn
145                 150                 155                 160

<210> SEQ ID NO 178
<211> LENGTH: 160
<212> TYPE: PRT
<213> ORGANISM: Carpinus betulus

<400> SEQUENCE: 178

Met Gly Val Phe Asn Tyr Glu Ala Glu Thr Pro Ser Val Ile Pro Ala
 1               5                  10                  15

Ala Arg Leu Phe Lys Ser Tyr Val Leu Asp Phe Asp Lys Leu Ile Pro
                 20                  25                  30

Lys Val Ala Pro Gln Ala Ile Ser Ser Val Glu Asn Val Gly Gly Asn
                 35                  40                  45

Gly Gly Pro Gly Thr Ile Lys Asn Ile Thr Phe Ala Glu Gly Ser Pro
 50                  55                  60

Phe Lys Phe Val Lys Glu Arg Val Asp Glu Val Asp Asn Ala Asn Phe
 65                  70                  75                  80

Lys Tyr Asn Tyr Thr Val Ile Glu Gly Asp Val Leu Gly Asp Lys Leu
                 85                  90                  95

Glu Lys Val Ser His Glu Leu Lys Ile Val Ala Ala Pro Gly Gly Gly
                100                 105                 110

Ser Ile Val Lys Ile Ser Ser Lys Phe His Ala Lys Gly Asp His Glu
                115                 120                 125

Val Asn Ala Glu Glu Met Lys Gly Ala Lys Glu Met Ala Glu Lys Leu
                130                 135                 140

Leu Arg Ala Val Glu Ser Tyr Leu Leu Ala His Thr Ala Glu Tyr Asn
145                 150                 155                 160

<210> SEQ ID NO 179
<211> LENGTH: 160
<212> TYPE: PRT
<213> ORGANISM: Carpinus betulus

<400> SEQUENCE: 179

Met Gly Val Phe Asn Tyr Glu Ala Glu Thr Pro Ser Val Ile Pro Ala
 1               5                  10                  15

Ala Arg Leu Phe Lys Ser Tyr Val Leu Asp Phe Asp Lys Leu Ile Pro
                 20                  25                  30

Lys Val Ala Pro Gln Ala Ile Ser Ser Val Glu Asn Val Gly Gly Asn
                 35                  40                  45

Gly Gly Pro Gly Thr Ile Lys Asn Ile Thr Phe Ala Glu Gly Ser Pro
 50                  55                  60
```

```
Phe Lys Phe Val Lys Glu Arg Val Asp Glu Val Asp Asn Ala Asn Phe
 65                  70                  75                  80

Lys Phe Ser Tyr Thr Val Ile Glu Gly Asp Val Leu Gly Asp Lys Leu
                 85                  90                  95

Glu Lys Val Ser Leu Glu Leu Lys Ile Val Ala Ala Pro Gly Gly Gly
            100                 105                 110

Ser Ile Leu Lys Ile Ser Gly Lys Phe His Ala Lys Gly Asp His Glu
            115                 120                 125

Val Asn Ala Glu Glu Met Lys Gly Ala Lys Glu Met Ala Glu Lys Leu
        130                 135                 140

Leu Arg Ala Val Glu Ser Tyr Leu Leu Ala His Thr Ala Glu Tyr Asn
145                 150                 155                 160

<210> SEQ ID NO 180
<211> LENGTH: 160
<212> TYPE: PRT
<213> ORGANISM: Carpinus betulus

<400> SEQUENCE: 180

Met Gly Val Phe Asn Tyr Glu Ala Glu Thr Pro Ser Val Ile Pro Ala
1                5                  10                  15

Ala Arg Leu Phe Lys Ser Tyr Val Leu Asp Phe Asp Lys Leu Ile Pro
                 20                  25                  30

Lys Val Ala Pro Gln Ala Ile Ser Val Glu Asn Val Gly Gly Asn
             35                  40                  45

Gly Gly Pro Gly Thr Ile Lys Asn Ile Thr Phe Ala Glu Gly Ser Pro
         50                  55                  60

Phe Lys Phe Val Lys Glu Arg Val Asp Glu Val Asp Asn Ala Asn Phe
 65                  70                  75                  80

Lys Phe Ser Tyr Thr Val Ile Glu Gly Asp Val Leu Gly Asp Lys Leu
                 85                  90                  95

Glu Lys Val Ser Leu Glu Leu Lys Ile Val Ala Ala Pro Gly Gly Gly
            100                 105                 110

Ser Ile Leu Lys Ile Ser Gly Lys Phe His Ala Lys Gly Asp His Glu
            115                 120                 125

Val Asn Ala Glu Glu Met Lys Gly Ala Lys Glu Met Ala Glu Lys Leu
        130                 135                 140

Leu Arg Ala Val Glu Ser Tyr Leu Leu Ala His Thr Ala Glu Tyr Asn
145                 150                 155                 160

<210> SEQ ID NO 181
<211> LENGTH: 159
<212> TYPE: PRT
<213> ORGANISM: Carpinus betulus

<400> SEQUENCE: 181

Gly Val Phe Asn Tyr Glu Ala Glu Thr Thr Ser Val Ile Pro Ala Ala
1                5                  10                  15

Arg Leu Phe Lys Ala Phe Ile Leu Asp Gly Asn Lys Leu Ile Pro Lys
                 20                  25                  30

Val Ser Pro Gln Ala Val Ser Val Glu Asn Val Glu Gly Asn Gly
             35                  40                  45

Gly Pro Gly Thr Ile Lys Lys Ile Thr Phe Ser Glu Gly Ser Pro Val
         50                  55                  60

Lys Tyr Val Lys Glu Arg Val Glu Glu Ile Asp His Thr Asn Phe Lys
 65                  70                  75                  80
```

Tyr Asn Tyr Thr Val Ile Glu Gly Asp Val Leu Gly Asp Lys Leu Glu
                85                  90                  95

Lys Val Ser His Glu Leu Lys Ile Val Ala Ala Pro Gly Gly Gly Ser
            100                 105                 110

Ile Val Lys Ile Ser Ser Lys Phe His Ala Lys Gly Tyr His Glu Val
        115                 120                 125

Asn Ala Glu Glu Met Lys Gly Ala Lys Glu Met Ala Glu Lys Leu Leu
    130                 135                 140

Arg Ala Val Glu Ser Tyr Leu Leu Ala His Thr Ala Glu Tyr Asn
145                 150                 155

<210> SEQ ID NO 182
<211> LENGTH: 160
<212> TYPE: PRT
<213> ORGANISM: Carpinus betulus

<400> SEQUENCE: 182

Met Gly Val Phe Asn Tyr Glu Ala Glu Thr Pro Ser Val Met Pro Ala
1               5                   10                  15

Ala Arg Leu Phe Lys Ser Tyr Val Leu Asp Phe Asp Lys Leu Ile Pro
            20                  25                  30

Lys Val Ala Pro Gln Ala Ile Ser Ser Val Glu Asn Val Gly Gly Asn
        35                  40                  45

Gly Gly Pro Gly Thr Ile Lys Asn Ile Thr Phe Ala Glu Gly Ser Pro
    50                  55                  60

Phe Lys Phe Val Lys Glu Arg Val Asp Glu Val Asp Asn Ala Asn Phe
65                  70                  75                  80

Lys Phe Ser Tyr Thr Val Ile Glu Gly Asp Val Leu Gly Asp Lys Leu
                85                  90                  95

Glu Lys Val Ser Leu Glu Leu Thr Ile Val Ala Ala Pro Gly Gly Gly
            100                 105                 110

Ser Ile Leu Lys Ile Ser Gly Lys Phe His Ala Lys Gly Asp His Glu
        115                 120                 125

Val Asn Ala Glu Glu Met Lys Gly Ala Lys Glu Met Ala Glu Lys Leu
    130                 135                 140

Leu Arg Ala Val Glu Ser Tyr Leu Leu Ala His Thr Ala Glu Tyr Asn
145                 150                 155                 160

<210> SEQ ID NO 183
<211> LENGTH: 160
<212> TYPE: PRT
<213> ORGANISM: Betula platyphylla var. japonica

<400> SEQUENCE: 183

Met Gly Val Phe Asn Tyr Glu Thr Glu Thr Ser Val Ile Pro Ala
1               5                   10                  15

Ala Arg Leu Phe Lys Ala Phe Ile Leu Asp Gly Asp Lys Leu Val Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Asn Phe Pro Glu Gly Phe Pro
    50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Val Gly Asp Thr Leu
                85                  90                  95

```
Glu Lys Ile Ser Asn Glu Ile Lys Ile Val Ala Thr Pro Asp Gly Gly
                100                 105                 110

Cys Val Leu Lys Ile Ser Asn Lys Tyr His Thr Lys Gly Asn His Glu
            115                 120                 125

Val Lys Ala Glu Gln Val Lys Ala Ser Lys Glu Met Gly Glu Thr Leu
        130                 135                 140

Leu Arg Ala Val Glu Ser Tyr Leu Leu Ser His Ser Asp Ala Tyr Asn
145                 150                 155                 160

<210> SEQ ID NO 184
<211> LENGTH: 160
<212> TYPE: PRT
<213> ORGANISM: Betula platyphylla var. japonica

<400> SEQUENCE: 184

Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Phe Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Ser Phe Pro Glu Gly Phe Pro
    50                  55                  60

Phe Lys Tyr Val Lys Asp Gly Val Asp Glu Val Asp His Thr Asn Phe
65                  70                  75                  80

Lys Tyr Asn Tyr Ser Val Ile Glu Gly Gly Pro Val Gly Asp Thr Leu
                85                  90                  95

Glu Lys Ile Ser Asn Glu Ile Lys Ile Val Ala Thr Pro Asp Gly Gly
                100                 105                 110

Cys Val Leu Lys Ile Ser Asn Lys Tyr His Thr Lys Gly Asn His Glu
            115                 120                 125

Val Lys Ala Glu Gln Val Lys Ala Ser Lys Glu Met Gly Glu Thr Leu
        130                 135                 140

Leu Arg Ala Val Glu Ser Tyr Leu Leu Ser His Ser Asp Ala Tyr Asn
145                 150                 155                 160

<210> SEQ ID NO 185
<211> LENGTH: 160
<212> TYPE: PRT
<213> ORGANISM: Betula platyphylla var. japonica

<400> SEQUENCE: 185

Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Phe Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Ser Phe Pro Glu Gly Phe Pro
    50                  55                  60

Phe Glu Tyr Val Lys Asp Arg Val Asp Glu Val Asp His Thr Asn Phe
65                  70                  75                  80

Lys Tyr Asn Tyr Ser Val Ile Glu Gly Gly Pro Val Gly Asp Thr Leu
                85                  90                  95

Glu Lys Ile Ser Asn Glu Ile Lys Ile Val Ala Thr Pro Asp Gly Gly
                100                 105                 110
```

```
Cys Val Leu Lys Ile Ser Asn Lys Tyr His Thr Lys Gly Asn His Glu
        115                 120                 125

Val Lys Ala Glu Gln Val Lys Ala Ser Lys Glu Met Gly Glu Thr Leu
        130                 135                 140

Leu Arg Ala Val Glu Ser Tyr Leu Leu Ser His Ser Asp Ala Tyr Asn
145                 150                 155                 160

<210> SEQ ID NO 186
<211> LENGTH: 160
<212> TYPE: PRT
<213> ORGANISM: Fagus sylvatica

<400> SEQUENCE: 186

Met Gly Val Phe Thr Tyr Glu Ser Glu Asn Thr Ser Val Ile Pro Pro
1               5                   10                  15

Ala Arg Leu Phe Lys Ala Phe Val Leu Asp Ala Asp Asn Leu Ile Pro
            20                  25                  30

Lys Val Ala Pro Gln Ser Ile Lys Ser Thr Glu Thr Leu Glu Gly Asp
        35                  40                  45

Gly Gly Pro Gly Thr Ile Lys Lys Ile Thr Phe Gly Glu Gly Ser Gln
    50                  55                  60

Phe Lys Tyr Val Lys His Arg Ile Asp Glu Val Asp Gln Ala Asn Phe
65                  70                  75                  80

Ser Tyr Gly Tyr Ser Val Ile Glu Gly Asp Val Val Ser Gly Ile Ile
                85                  90                  95

Glu Lys Ile Ser Tyr Glu Ile Lys Ile Val Ala Ser Pro Asp Gly Gly
            100                 105                 110

Ser Leu Leu Lys Ser Thr Ser Lys Tyr His Ile Lys Gly Asn His Glu
        115                 120                 125

Ile Lys Glu Glu Val Lys Ala Gly Lys Glu Lys Ala Ala Gly Leu
        130                 135                 140

Phe Lys Ala Val Glu Ala Tyr Leu Leu Ala His Pro Asp Ala Tyr Asn
145                 150                 155                 160

<210> SEQ ID NO 187
<211> LENGTH: 159
<212> TYPE: PRT
<213> ORGANISM: Malus domestica

<400> SEQUENCE: 187

Met Gly Val Tyr Thr Phe Glu Asn Glu Phe Thr Ser Glu Ile Pro Pro
1               5                   10                  15

Ser Arg Leu Phe Lys Ala Phe Val Leu Asp Ala Asp Asn Leu Ile Pro
            20                  25                  30

Lys Ile Ala Pro Gln Ala Ile Lys Gln Ala Glu Ile Leu Glu Gly Asn
        35                  40                  45

Gly Gly Pro Gly Thr Ile Lys Lys Ile Thr Phe Gly Glu Gly Ser Gln
    50                  55                  60

Tyr Gly Tyr Val Lys His Arg Ile Asp Ser Ile Asp Glu Ala Ser Tyr
65                  70                  75                  80

Ser Tyr Ser Tyr Thr Leu Ile Glu Gly Asp Ala Leu Thr Asp Thr Ile
                85                  90                  95

Glu Lys Ile Ser Tyr Glu Thr Lys Leu Val Ala Cys Gly Ser Gly Ser
            100                 105                 110

Thr Ile Lys Ser Ile Ser His Tyr His Thr Lys Gly Asn Ile Glu Ile
        115                 120                 125
```

```
Lys Glu Glu His Val Lys Val Gly Lys Glu Lys Ala His Gly Leu Phe
            130                 135                 140

Lys Leu Ile Glu Ser Tyr Leu Lys Asp His Pro Asp Ala Tyr Asn
145                 150                 155
```

<210> SEQ ID NO 188
<211> LENGTH: 159
<212> TYPE: PRT
<213> ORGANISM: Malus domestica

<400> SEQUENCE: 188

```
Met Gly Val Tyr Thr Phe Glu Asn Glu Phe Thr Ser Glu Ile Pro Pro
1               5                   10                  15

Ser Arg Leu Phe Lys Ala Phe Val Leu Asp Ala Asp Asn Leu Ile Pro
                20                  25                  30

Lys Ile Ala Pro Gln Ala Ile Lys Gln Ala Glu Ile Leu Glu Gly Asn
            35                  40                  45

Gly Gly Pro Gly Thr Ile Lys Lys Ile Thr Phe Gly Glu Gly Ser Gln
        50                  55                  60

Tyr Gly Tyr Val Lys His Arg Ile Asp Ser Ile Asp Glu Ala Ser Tyr
65                  70                  75                  80

Ser Tyr Ser Tyr Thr Leu Ile Glu Gly Asp Ala Leu Thr Asp Thr Ile
                85                  90                  95

Glu Lys Ile Ser Tyr Glu Thr Lys Leu Val Ala Cys Gly Ser Gly Ala
            100                 105                 110

Thr Ile Lys Ser Ile Ser His Tyr His Pro Lys Gly Asn Ile Glu Ile
        115                 120                 125

Lys Glu Glu His Val Lys Val Gly Lys Glu Lys Gly His Gly Leu Phe
    130                 135                 140

Lys Leu Ile Glu Ser Tyr Leu Lys Gly His Pro Asp Ala Tyr Asn
145                 150                 155
```

<210> SEQ ID NO 189
<211> LENGTH: 159
<212> TYPE: PRT
<213> ORGANISM: Malus domestica

<400> SEQUENCE: 189

```
Met Gly Val Tyr Thr Phe Glu Asn Glu Phe Thr Ser Glu Ile Pro Pro
1               5                   10                  15

Ser Arg Leu Phe Lys Ala Phe Val Leu Asp Ala Asp Asn Leu Ile Pro
                20                  25                  30

Lys Ile Ala Pro Gln Ala Ile Lys Gln Ala Glu Ile Leu Glu Gly Asn
            35                  40                  45

Gly Gly Pro Gly Thr Ile Lys Lys Ile Thr Phe Gly Glu Gly Ser Gln
        50                  55                  60

Tyr Gly Tyr Val Lys His Arg Ile Asp Ser Ile Asp Glu Ala Ser Tyr
65                  70                  75                  80

Ser Tyr Ser Tyr Thr Leu Ile Glu Gly Asp Ala Leu Thr Asp Thr Ile
                85                  90                  95

Glu Lys Ile Ser Tyr Glu Thr Lys Leu Val Ala Cys Gly Ser Gly Ser
            100                 105                 110

Thr Ile Lys Ser Ile Ser His Tyr His Thr Lys Gly Asn Ile Glu Ile
        115                 120                 125

Lys Glu Glu His Val Lys Ala Gly Lys Glu Lys Ala His Gly Leu Phe
    130                 135                 140
```

```
Lys Leu Ile Glu Ser Tyr Leu Lys Gly His Pro Asp Ala Tyr Asn
145                 150                 155
```

<210> SEQ ID NO 190
<211> LENGTH: 159
<212> TYPE: PRT
<213> ORGANISM: Malus domestica

<400> SEQUENCE: 190

```
Met Gly Val Tyr Thr Phe Glu Asn Glu Tyr Thr Ser Glu Ile Pro Pro
1               5                   10                  15

Pro Arg Leu Phe Lys Ala Phe Val Leu Asp Ala Asp Asn Leu Ile Pro
                20                  25                  30

Lys Ile Ala Pro Gln Ala Ile Lys Gln Ala Glu Ile Leu Glu Gly Asn
            35                  40                  45

Gly Gly Pro Gly Thr Ile Lys Lys Ile Thr Phe Gly Glu Gly Ser Gln
        50                  55                  60

Tyr Gly Tyr Val Lys His Arg Ile Asp Ser Ile Asp Glu Ala Ser Tyr
65                  70                  75                  80

Ser Tyr Ser Tyr Thr Leu Ile Glu Gly Asp Ala Leu Thr Asp Thr Ile
                85                  90                  95

Glu Lys Ile Ser Tyr Glu Thr Lys Leu Val Ala Cys Gly Ser Gly Ser
                100                 105                 110

Thr Ile Lys Ser Ile Ser His Tyr His Thr Lys Gly Asn Ile Glu Ile
            115                 120                 125

Lys Glu Glu His Val Lys Ala Gly Lys Glu Lys Ala His Gly Leu Phe
        130                 135                 140

Lys Leu Ile Glu Ser Tyr Leu Lys Asp His Pro Asp Ala Tyr Asn
145                 150                 155
```

<210> SEQ ID NO 191
<211> LENGTH: 159
<212> TYPE: PRT
<213> ORGANISM: Malus domestica

<400> SEQUENCE: 191

```
Met Gly Val Cys Thr Phe Glu Asn Glu Phe Thr Ser Glu Ile Pro Pro
1               5                   10                  15

Ser Arg Leu Phe Lys Ala Phe Val Leu Asp Ala Asp Asn Leu Ile Pro
                20                  25                  30

Lys Ile Ala Pro Gln Ala Ile Lys Gln Ala Glu Ile Leu Glu Gly Asn
            35                  40                  45

Gly Gly Pro Gly Thr Ile Lys Lys Ile Thr Phe Gly Glu Gly Ser Gln
        50                  55                  60

Tyr Gly Tyr Val Lys His Arg Ile Asp Ser Ile Asp Glu Ala Ser Tyr
65                  70                  75                  80

Ser Tyr Ser Tyr Thr Leu Ile Glu Gly Asp Ala Leu Thr Asp Thr Ile
                85                  90                  95

Glu Lys Ile Ser Tyr Glu Thr Lys Leu Val Ala Cys Gly Ser Gly Ser
                100                 105                 110

Thr Ile Lys Ser Ile Ser His Tyr His Thr Lys Gly Asn Ile Glu Ile
            115                 120                 125

Lys Glu Glu His Val Lys Ala Gly Lys Glu Lys Ala His Gly Leu Phe
        130                 135                 140

Lys Leu Ile Glu Ser Tyr Leu Lys Asp His Pro Asp Ala Tyr Asn
145                 150                 155
```

<210> SEQ ID NO 192
<211> LENGTH: 159
<212> TYPE: PRT
<213> ORGANISM: Malus domestica

<400> SEQUENCE: 192

Met Gly Val Tyr Thr Phe Glu Asn Glu Phe Thr Ser Glu Ile Pro Pro
1               5                   10                  15

Ser Arg Leu Phe Lys Ala Phe Val Leu Asp Ala Asp Asn Leu Ile Pro
                20                  25                  30

Lys Ile Ala Pro Gln Ala Ile Lys Gln Ala Glu Ile Leu Glu Gly Asn
            35                  40                  45

Gly Gly Pro Gly Thr Ile Lys Lys Ile Thr Phe Gly Glu Gly Ser Gln
        50                  55                  60

Tyr Gly Tyr Val Lys His Arg Ile Asp Ser Ile Asp Glu Ala Ser Tyr
65                  70                  75                  80

Ser Tyr Ser Tyr Thr Leu Ile Glu Gly Asp Ala Leu Thr Asp Thr Ile
                85                  90                  95

Glu Asn Ile Ser Tyr Glu Thr Lys Leu Val Ala Cys Gly Ser Gly Ser
            100                 105                 110

Thr Ile Lys Ser Ile Ser His Tyr His Thr Lys Gly Asn Ile Glu Ile
        115                 120                 125

Lys Glu Glu His Val Lys Ala Gly Lys Glu Lys Ala His Gly Leu Phe
    130                 135                 140

Lys Leu Ile Glu Ser Tyr Leu Lys Asp His Pro Asp Ala Tyr Asn
145                 150                 155

<210> SEQ ID NO 193
<211> LENGTH: 159
<212> TYPE: PRT
<213> ORGANISM: Malus domestica

<400> SEQUENCE: 193

Met Gly Val Tyr Thr Phe Glu Asn Glu Tyr Thr Ser Glu Ile Pro Pro
1               5                   10                  15

Ser Arg Leu Phe Lys Ala Phe Val Leu Asp Ala Asp Asn Leu Ile Pro
                20                  25                  30

Lys Ile Ala Pro Gln Ala Ile Lys Gln Ala Glu Ile Leu Glu Gly Asn
            35                  40                  45

Gly Gly Pro Gly Thr Ile Lys Lys Ile Thr Phe Gly Glu Gly Ser Gln
        50                  55                  60

Tyr Gly Tyr Val Lys His Arg Ile Asp Ser Ile Asp Glu Ala Ser Tyr
65                  70                  75                  80

Ser Tyr Ser Tyr Thr Leu Ile Glu Gly Asp Ala Leu Thr Asp Thr Ile
                85                  90                  95

Glu Lys Ile Ser Tyr Glu Thr Lys Leu Val Ala Cys Gly Ser Gly Ser
            100                 105                 110

Thr Ile Lys Ser Ile Ser His Tyr His Thr Lys Gly Asn Ile Glu Ile
        115                 120                 125

Lys Glu Glu His Val Lys Ala Gly Lys Ala Lys Ala His Gly Leu Phe
    130                 135                 140

Lys Leu Ile Glu Ser Tyr Leu Lys Gly His Pro Asp Ala Tyr Asn
145                 150                 155

<210> SEQ ID NO 194

<211> LENGTH: 159
<212> TYPE: PRT
<213> ORGANISM: Malus domestica

<400> SEQUENCE: 194

```
Met Gly Val Tyr Thr Phe Glu Asn Glu Phe Thr Ser Glu Ile Pro Pro
1               5                   10                  15
Ser Arg Leu Phe Lys Ala Phe Val Leu Asp Ala Asp Asn Leu Ile Pro
            20                  25                  30
Lys Ile Ala Pro Gln Ala Ile Lys Gln Ala Glu Ile Leu Glu Gly Asn
        35                  40                  45
Gly Gly Pro Gly Thr Ile Lys Lys Ile Thr Phe Gly Glu Gly Ser Gln
    50                  55                  60
Tyr Gly Tyr Val Lys His Arg Ile Asp Ser Ile Asp Glu Ala Ser Tyr
65                  70                  75                  80
Ser Tyr Ser Tyr Thr Leu Ile Glu Gly Asp Ala Leu Thr Asp Thr Ile
                85                  90                  95
Glu Lys Ile Ser Tyr Glu Thr Lys Leu Val Ala Cys Gly Ser Gly Ser
            100                 105                 110
Thr Ile Lys Ser Ile Ser His Tyr His Thr Lys Gly Asn Ile Glu Ile
        115                 120                 125
Lys Glu Glu His Val Lys Ala Gly Lys Glu Lys Ala His Gly Leu Phe
    130                 135                 140
Lys Leu Ile Glu Ser Tyr Leu Lys Asp His Pro Asp Ala Tyr Asn
145                 150                 155
```

<210> SEQ ID NO 195
<211> LENGTH: 159
<212> TYPE: PRT
<213> ORGANISM: Malus domestica

<400> SEQUENCE: 195

```
Met Gly Val Cys Thr Phe Glu Asn Glu Phe Thr Ser Glu Ile Pro Pro
1               5                   10                  15
Ser Arg Leu Phe Lys Ala Phe Val Leu Asp Ala Asp Asn Leu Ile Pro
            20                  25                  30
Lys Ile Ala Pro Gln Ala Ile Lys Gln Ala Glu Ile Leu Glu Gly Asn
        35                  40                  45
Gly Gly Pro Gly Thr Ile Lys Lys Ile Thr Phe Gly Glu Gly Ser Gln
    50                  55                  60
Tyr Gly Tyr Val Lys His Arg Ile Asp Ser Ile Asp Glu Ala Ser Tyr
65                  70                  75                  80
Ser Tyr Ser Tyr Thr Leu Ile Glu Gly Asp Ala Leu Thr Asp Thr Ile
                85                  90                  95
Glu Lys Ile Ser Tyr Glu Thr Lys Leu Val Ala Cys Gly Ser Gly Ser
            100                 105                 110
Thr Ile Lys Ser Ile Ser His Tyr His Thr Lys Gly Asn Ile Glu Ile
        115                 120                 125
Lys Glu Glu His Val Lys Val Gly Lys Glu Lys Ala His Gly Leu Phe
    130                 135                 140
Lys Leu Ile Glu Ser Tyr Leu Lys Asp His Pro Asp Ala Tyr Asn
145                 150                 155
```

<210> SEQ ID NO 196
<211> LENGTH: 159
<212> TYPE: PRT
<213> ORGANISM: Malus domestica

<400> SEQUENCE: 196

| Met | Gly | Val | Tyr | Thr | Phe | Glu | Asn | Glu | Tyr | Thr | Ser | Glu | Ile | Pro | Pro |
| 1 | | | | 5 | | | | | 10 | | | | | 15 | |

| Pro | Arg | Leu | Phe | Lys | Ala | Phe | Val | Leu | Asp | Ala | Asp | Asn | Leu | Ile | Pro |
| | | | | 20 | | | | | 25 | | | | | 30 | |

| Lys | Ile | Ala | Pro | Gln | Ala | Ile | Lys | His | Ala | Glu | Ile | Leu | Glu | Gly | Asp |
| | | | 35 | | | | | 40 | | | | | 45 | | |

| Gly | Gly | Pro | Gly | Thr | Ile | Lys | Lys | Ile | Thr | Phe | Gly | Glu | Gly | Ser | Gln |
| | 50 | | | | | 55 | | | | | 60 | | | | |

| Tyr | Gly | Tyr | Val | Lys | His | Lys | Ile | Asp | Ser | Val | Asp | Glu | Ala | Asn | Tyr |
| 65 | | | | | 70 | | | | | 75 | | | | | 80 |

| Ser | Tyr | Ala | Tyr | Thr | Leu | Ile | Glu | Gly | Asp | Ala | Leu | Thr | Asp | Thr | Ile |
| | | | | 85 | | | | | 90 | | | | | 95 | |

| Glu | Lys | Val | Ser | Tyr | Glu | Thr | Lys | Leu | Val | Ala | Ser | Gly | Ser | Gly | Ser |
| | | | | 100 | | | | | 105 | | | | | 110 | |

| Ile | Ile | Lys | Ser | Ile | Ser | His | Tyr | His | Thr | Lys | Gly | Asp | Val | Glu | Ile |
| | | | | 115 | | | | | 120 | | | | | 125 | |

| Lys | Glu | Glu | His | Val | Lys | Ala | Gly | Lys | Glu | Lys | Ala | His | Gly | Leu | Phe |
| | | | 130 | | | | | 135 | | | | | 140 | | |

| Lys | Leu | Ile | Glu | Ser | Tyr | Leu | Lys | Gly | His | Pro | Asp | Ala | Tyr | Asn |
| 145 | | | | | 150 | | | | | 155 | | | | |

<210> SEQ ID NO 197
<211> LENGTH: 159
<212> TYPE: PRT
<213> ORGANISM: Malus domestica

<400> SEQUENCE: 197

| Met | Gly | Val | Tyr | Thr | Phe | Glu | Asn | Glu | Tyr | Thr | Ser | Glu | Ile | Pro | Pro |
| 1 | | | | 5 | | | | | 10 | | | | | 15 | |

| Pro | Arg | Leu | Phe | Lys | Ala | Phe | Val | Leu | Asp | Ala | Asp | Asn | Leu | Ile | Pro |
| | | | | 20 | | | | | 25 | | | | | 30 | |

| Lys | Ile | Ala | Pro | Gln | Ala | Ile | Lys | His | Ala | Glu | Ile | Leu | Glu | Gly | Asp |
| | | | 35 | | | | | 40 | | | | | 45 | | |

| Gly | Gly | Pro | Gly | Thr | Ile | Lys | Lys | Ile | Thr | Phe | Gly | Glu | Gly | Ser | Gln |
| | 50 | | | | | 55 | | | | | 60 | | | | |

| Tyr | Gly | Tyr | Val | Lys | His | Lys | Ile | Asp | Ser | Val | Asp | Glu | Ala | Asn | Tyr |
| 65 | | | | | 70 | | | | | 75 | | | | | 80 |

| Ser | Tyr | Ala | Tyr | Thr | Leu | Ile | Glu | Gly | Asp | Ala | Leu | Thr | Asp | Thr | Ile |
| | | | | 85 | | | | | 90 | | | | | 95 | |

| Glu | Lys | Val | Ser | Tyr | Glu | Thr | Lys | Leu | Val | Ala | Ser | Gly | Ser | Gly | Ser |
| | | | | 100 | | | | | 105 | | | | | 110 | |

| Ile | Ile | Lys | Ser | Ile | Ser | His | Tyr | His | Thr | Lys | Gly | Asp | Val | Glu | Ile |
| | | | | 115 | | | | | 120 | | | | | 125 | |

| Lys | Glu | Glu | His | Val | Lys | Ala | Gly | Lys | Glu | Lys | Ala | His | Gly | Leu | Phe |
| | | | 130 | | | | | 135 | | | | | 140 | | |

| Lys | Leu | Ile | Glu | Ser | Tyr | Leu | Lys | Gly | His | Pro | Asp | Ala | Tyr | Asn |
| 145 | | | | | 150 | | | | | 155 | | | | |

<210> SEQ ID NO 198
<211> LENGTH: 159
<212> TYPE: PRT
<213> ORGANISM: Malus domestica

<400> SEQUENCE: 198

Met Gly Val Tyr Thr Phe Glu Asn Glu Tyr Thr Ser Glu Ile Pro Pro
1               5                   10                  15

Pro Arg Leu Phe Lys Ala Phe Val Leu Asp Ala Asp Asn Leu Ile Pro
                20                  25                  30

Lys Ile Ala Pro Gln Ala Ile Lys His Ala Glu Ile Leu Glu Gly Asp
            35                  40                  45

Gly Gly Pro Gly Thr Ile Lys Lys Ile Thr Phe Gly Glu Gly Ser Gln
        50                  55                  60

Tyr Gly Tyr Val Lys His Lys Ile Asp Ser Val Asp Glu Ala Asn Tyr
65                  70                  75                  80

Ser Tyr Ala Tyr Thr Leu Ile Glu Gly Asp Ala Leu Thr Asp Thr Ile
                85                  90                  95

Glu Lys Val Ser Tyr Glu Thr Lys Leu Val Ala Ser Gly Ser Gly Ser
            100                 105                 110

Ile Ile Lys Ser Ile Ser His Tyr His Thr Lys Gly Asp Val Glu Ile
        115                 120                 125

Lys Glu Glu His Val Lys Ala Gly Lys Glu Lys Ala His Gly Leu Phe
    130                 135                 140

Lys Leu Ile Glu Ser His Leu Lys Gly His Pro Asp Ala Tyr Asn
145                 150                 155

<210> SEQ ID NO 199
<211> LENGTH: 159
<212> TYPE: PRT
<213> ORGANISM: Malus domestica

<400> SEQUENCE: 199

Met Gly Val Tyr Thr Phe Glu Asn Glu Tyr Thr Ser Glu Ile Pro Pro
1               5                   10                  15

Pro Arg Leu Phe Lys Ala Phe Val Leu Asp Ala Asp Asn Leu Ile Pro
                20                  25                  30

Lys Ile Ala Pro Gln Ala Ile Lys His Ala Glu Ile Leu Glu Gly Asp
            35                  40                  45

Gly Gly Pro Gly Thr Ile Lys Lys Ile Thr Phe Gly Glu Gly Ser Gln
        50                  55                  60

Tyr Gly Tyr Val Lys His Lys Ile Asp Ser Val Asp Glu Ala Asn Tyr
65                  70                  75                  80

Ser Tyr Ala Tyr Thr Leu Ile Glu Gly Asp Ala Leu Thr Asp Thr Ile
                85                  90                  95

Glu Lys Val Ser Tyr Glu Thr Lys Leu Met Ala Ser Gly Ser Gly Ser
            100                 105                 110

Ile Ile Lys Ser Ile Ser His Tyr His Thr Lys Gly Asp Val Glu Ile
        115                 120                 125

Lys Glu Glu His Val Lys Ala Gly Lys Glu Lys Ala His Gly Leu Phe
    130                 135                 140

Lys Leu Ile Glu Ser Tyr Leu Lys Gly His Pro Asp Ala Tyr Asn
145                 150                 155

<210> SEQ ID NO 200
<211> LENGTH: 159
<212> TYPE: PRT
<213> ORGANISM: Malus domestica

<400> SEQUENCE: 200

Met Gly Val Tyr Thr Phe Glu Asn Glu Tyr Thr Ser Glu Ile Pro Pro
1               5                   10                  15

```
Pro Arg Leu Phe Lys Ala Phe Val Leu Asp Ala Asp Asn Leu Ile Pro
             20                  25                  30

Lys Ile Ala Pro Gln Ala Ile Lys His Ala Glu Ile Leu Glu Gly Asp
         35                  40                  45

Gly Gly Pro Gly Thr Ile Lys Lys Ile Thr Phe Gly Glu Gly Ser Gln
     50                  55                  60

Tyr Gly Tyr Val Lys His Lys Ile Asp Ser Val Asp Glu Ala Asn Tyr
 65                  70                  75                  80

Ser Tyr Ala Tyr Thr Leu Ile Glu Gly Asp Ala Leu Thr Asp Thr Ile
                 85                  90                  95

Glu Lys Val Ser Tyr Glu Thr Lys Leu Val Ala Ser Gly Ser Gly Ser
                100                 105                 110

Ile Ile Lys Ser Ile Ser His Tyr His Thr Lys Gly Asp Val Glu Ile
                115                 120                 125

Lys Glu Glu His Val Met Ala Gly Lys Glu Lys Ala His Gly Leu Phe
            130                 135                 140

Lys Leu Ile Glu Ser Tyr Leu Lys Gly His Pro Asp Ala Tyr Asn
145                 150                 155

<210> SEQ ID NO 201
<211> LENGTH: 159
<212> TYPE: PRT
<213> ORGANISM: Malus domestica

<400> SEQUENCE: 201

Met Gly Val Tyr Thr Phe Glu Asn Glu Tyr Thr Ser Glu Ile Pro Pro
 1               5                  10                  15

Pro Arg Leu Phe Lys Gly Phe Val Leu Asp Ala Asp Asn Leu Ile Pro
             20                  25                  30

Lys Ile Ala Pro Gln Ala Ile Lys His Ala Glu Ile Leu Glu Gly Asp
         35                  40                  45

Gly Gly Pro Gly Thr Ile Lys Lys Ile Thr Phe Gly Glu Gly Ser Gln
     50                  55                  60

Tyr Gly Tyr Val Lys His Lys Ile Asp Ser Val Asp Glu Ala Asn Tyr
 65                  70                  75                  80

Ser Tyr Ala Tyr Thr Leu Ile Glu Gly Asp Ala Leu Thr Asp Thr Ile
                 85                  90                  95

Glu Lys Val Ser Tyr Glu Thr Lys Leu Val Ala Ser Gly Ser Gly Ser
                100                 105                 110

Ile Ile Lys Ser Ile Ser His Tyr His Thr Lys Gly Asp Val Glu Ile
                115                 120                 125

Lys Glu Glu His Val Lys Ala Gly Lys Glu Lys Ala His Gly Leu Phe
            130                 135                 140

Lys Leu Ile Glu Ser Tyr Leu Lys Gly His Pro Asp Ala Tyr Asn
145                 150                 155

<210> SEQ ID NO 202
<211> LENGTH: 159
<212> TYPE: PRT
<213> ORGANISM: Malus domestica

<400> SEQUENCE: 202

Met Gly Val Tyr Thr Phe Glu Asn Glu Tyr Thr Ser Glu Ile Pro Pro
 1               5                  10                  15

Pro Arg Leu Phe Lys Ala Phe Val Leu Asp Ala Asp Asn Leu Ile Pro
             20                  25                  30
```

```
Lys Ile Ala Pro Gln Ala Ile Lys His Ala Glu Ile Leu Glu Gly Asp
            35                  40                  45

Gly Gly Pro Gly Thr Thr Lys Lys Ile Thr Phe Gly Glu Gly Ser Gln
 50                  55                  60

Tyr Gly Tyr Val Lys His Lys Ile Asp Ser Val Asp Glu Ala Asn Tyr
 65                  70                  75                  80

Ser Tyr Ala Tyr Thr Leu Ile Glu Gly Asp Ala Leu Thr Asp Thr Ile
                85                  90                  95

Glu Lys Val Ser Tyr Glu Thr Lys Leu Val Ala Ser Gly Ser Gly Ser
            100                 105                 110

Ile Ile Lys Ser Ile Ser His Tyr His Thr Lys Gly Asp Val Glu Ile
            115                 120                 125

Lys Glu Glu His Val Lys Ala Gly Lys Glu Lys Ala His Gly Leu Phe
130                 135                 140

Lys Leu Ile Glu Ser Tyr Leu Lys Gly His Pro Asp Ala Tyr Asn
145                 150                 155
```

<210> SEQ ID NO 203
<211> LENGTH: 158
<212> TYPE: PRT
<213> ORGANISM: Malus domestica

<400> SEQUENCE: 203

```
Gly Val Tyr Thr Tyr Glu Asn Glu Tyr Thr Ser Glu Ile Pro Pro Pro
 1               5                  10                  15

Arg Leu Phe Lys Ala Phe Val Leu Asp Ala Asp Asn Leu Ile Pro Lys
            20                  25                  30

Ile Ala Pro Gln Ala Ile Lys His Ala Glu Ile Leu Glu Gly Asp Gly
            35                  40                  45

Gly Pro Gly Thr Ile Lys Lys Ile Thr Phe Gly Glu Gly Ser Gln Tyr
 50                  55                  60

Gly Tyr Val Lys His Lys Ile Asp Ser Val Asp Glu Ala Asn Tyr Ser
 65                  70                  75                  80

Tyr Ala Tyr Thr Leu Ile Glu Gly Asp Ala Leu Thr Asp Thr Ile Glu
                85                  90                  95

Lys Val Ser Tyr Glu Thr Lys Leu Val Ala Ser Gly Ser Gly Ser Ile
            100                 105                 110

Ile Lys Ser Ile Ser His Tyr His Thr Lys Gly Asp Val Glu Ile Met
            115                 120                 125

Glu Glu His Val Lys Ala Gly Lys Glu Lys Ala His Gly Leu Phe Lys
130                 135                 140

Leu Ile Glu Ser Tyr Leu Lys Asp His Pro Asp Ala Tyr Asn
145                 150                 155
```

<210> SEQ ID NO 204
<211> LENGTH: 159
<212> TYPE: PRT
<213> ORGANISM: Malus domestica

<400> SEQUENCE: 204

```
Met Gly Val Phe Thr Tyr Glu Phe Glu Phe Thr Ser Val Ile Pro Pro
 1               5                  10                  15

Ala Arg Leu Tyr Asn Ala Phe Val Leu Asp Ala Asp Asn Leu Ile Pro
            20                  25                  30

Lys Ile Ala Pro Gln Ala Val Lys Ser Thr Glu Ile Leu Glu Gly Asp
            35                  40                  45
```

-continued

```
Gly Gly Val Gly Thr Ile Lys Lys Ile Asn Phe Gly Glu Gly Ser Thr
    50                  55                  60
Tyr Ser Tyr Val Lys His Lys Ile Asp Gly Val Asp Lys Asp Asn Phe
65                  70                  75                  80
Val Tyr Gln Tyr Ser Val Ile Glu Gly Asp Ala Ile Ser Glu Thr Ile
                85                  90                  95
Glu Lys Ile Ser Tyr Glu Thr Lys Leu Val Ala Ser Gly Ser Gly Ser
            100                 105                 110
Val Ile Lys Ser Ile Ser His Tyr His Thr Lys Gly Asp Val Glu Ile
        115                 120                 125
Lys Glu Glu His Val Lys Ala Gly Lys Glu Lys Ala Ser His Leu Phe
    130                 135                 140
Lys Leu Ile Glu Asn Tyr Leu Leu Glu His His Asp Ala Tyr Asn
145                 150                 155
```